(12) United States Patent
Parham et al.

(10) Patent No.: US 9,780,311 B2
(45) Date of Patent: Oct. 3, 2017

(54) COMPOUNDS FOR ELECTRONIC DEVICES

(75) Inventors: Amir Hossain Parham, Frankfurt am Main (DE); Christof Pflumm, Darmstadt (DE); Anja Jatsch, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 800 days.

(21) Appl. No.: 14/235,511

(22) PCT Filed: Jul. 3, 2012

(86) PCT No.: PCT/EP2012/002797
§ 371 (c)(1),
(2), (4) Date: Jan. 28, 2014

(87) PCT Pub. No.: WO2013/017189
PCT Pub. Date: Feb. 7, 2013

(65) Prior Publication Data
US 2014/0225040 A1    Aug. 14, 2014

(30) Foreign Application Priority Data

Jul. 29, 2011   (EP) .................................. 11006267

(51) Int. Cl.
| | | |
|---|---|---|
| *B32B 9/00* | (2006.01) |
| *B32B 19/00* | (2006.01) |
| *H01L 51/00* | (2006.01) |
| *C07D 307/94* | (2006.01) |
| *C07D 221/20* | (2006.01) |
| *C07D 401/04* | (2006.01) |
| *C07D 403/04* | (2006.01) |
| *C07D 403/14* | (2006.01) |
| *C07D 405/04* | (2006.01) |
| *C07D 409/04* | (2006.01) |
| *C07D 413/04* | (2006.01) |
| *C07D 417/04* | (2006.01) |
| *C07D 471/10* | (2006.01) |
| *C07D 471/20* | (2006.01) |
| *C07D 487/10* | (2006.01) |
| *C07D 265/34* | (2006.01) |
| *C07D 279/14* | (2006.01) |
| *C07D 209/96* | (2006.01) |
| *C07F 9/6568* | (2006.01) |
| *H01L 51/50* | (2006.01) |

(52) U.S. Cl.
CPC ........ *H01L 51/0072* (2013.01); *C07D 209/96* (2013.01); *C07D 221/20* (2013.01); *C07D 265/34* (2013.01); *C07D 279/14* (2013.01); *C07D 307/94* (2013.01); *C07D 401/04* (2013.01); *C07D 403/04* (2013.01); *C07D 403/14* (2013.01); *C07D 405/04* (2013.01); *C07D 409/04* (2013.01); *C07D 413/04* (2013.01); *C07D 417/04* (2013.01); *C07D 471/10* (2013.01); *C07D 471/20* (2013.01); *C07D 487/10* (2013.01); *C07F 9/65685* (2013.01); *H01L 51/0036* (2013.01); *H01L 51/0039* (2013.01); *H01L 51/0067* (2013.01); *H01L 51/0071* (2013.01); *H01L 51/0073* (2013.01); *H01L 51/0074* (2013.01); *H01L 51/0051* (2013.01); *H01L 51/0059* (2013.01); *H01L 51/0085* (2013.01); *H01L 51/0087* (2013.01); *H01L 51/5016* (2013.01); *H01L 2224/13394* (2013.01); *H01L 2924/12044* (2013.01); *Y02E 10/549* (2013.01)

(58) Field of Classification Search
USPC .......................................................... 257/40
See application file for complete search history.

(56) References Cited

U.S. PATENT DOCUMENTS

| | | | |
|---|---|---|---|
| 2007/0051944 A1* | 3/2007 | Vestweber | ........... C07D 239/26 257/40 |
| 2012/0068170 A1 | 3/2012 | Pflumm et al. | |
| 2012/0211701 A1* | 8/2012 | Spreitzer | ................. C07B 59/00 252/301.16 |

FOREIGN PATENT DOCUMENTS

| | | |
|---|---|---|
| CN | 1706839 A | 12/2005 |
| JP | 2002326965 A | 11/2002 |
| JP | 2008525533 A | 7/2008 |
| JP | 2009266927 A | 11/2009 |
| JP | 2010202599 A | 9/2010 |
| JP | 2012126673 A | 7/2012 |
| KR | 20100003624 A | 1/2010 |
| KR | 20100028471 A | 3/2010 |
| KR | 20100065218 A | 6/2010 |
| KR | 20100112903 A | 10/2010 |
| KR | 10-2009-059601 * | 1/2011 |
| KR | 20110002156 U | 3/2011 |
| KR | 20110068330 A | 6/2011 |
| WO | WO-2010136109 A1 | 12/2010 |

OTHER PUBLICATIONS

Machine translation of BAE (KR 10-2011-0002156).*
International Search Report for PCT/EP2012/002797 mailed Oct. 10, 2012.
Soon Ok Jeon et al., "Red phosphorescent organic light-emitting diodes . . . ", Materials Chemistry and Physics, 2011, vol. 127, pp. 300-304.

* cited by examiner

*Primary Examiner* — Austin Murata

(57) ABSTRACT

The present invention relates to compounds for use in electronic devices, preferably organic electroluminescent devices. The invention furthermore relates to processes for the preparation of these compounds and to electronic devices comprising these compounds, preferably in a function as matrix materials and/or as electron-transport materials.

20 Claims, No Drawings

COMPOUNDS FOR ELECTRONIC DEVICES

CROSS-REFERENCE TO RELATED APPLICATIONS

This application is a national stage application (under 35 U.S.C. §371) of PCT/EP2012/002797, filed Jul. 3, 2012, which claims benefit of European Application No. 11006267.6, filed Jul. 29, 2011, both of which are incorporated herein by reference in their entirety.

The present invention relates to compounds for use in electronic devices, preferably organic electroluminescent devices. The invention furthermore relates to processes for the preparation of these compounds and to electronic devices comprising the said compounds, preferably in a function as matrix materials and/or as electron-transport materials.

The development of novel functional compounds for use in electronic devices is currently the subject of intensive research. The aim here is the development and investigation of compounds which have hitherto not been employed in electronic devices and the development of compounds which facilitate an improved property profile of the devices.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

The structure of the above-mentioned organic electroluminescent devices (OLEDs) is known to the person skilled in the art and is described, inter alia, in U.S. Pat. No. 4,539,507, U.S. Pat. No. 5,151,629, EP 0676461 and WO 1998/27136.

Further improvements are still necessary regarding the performance data of the organic electroluminescent devices, in particular with a view to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices. In addition, it is desirable that the compounds for use as functional materials in electronic devices have high thermal stability and a high glass-transition temperature and can be sublimed without decomposition.

In the area of electronic devices comprising organic materials, there is a need for matrix materials, in particular for matrix materials for phosphorescent emitters, which simultaneously result in good efficiency, a long lifetime and low operating voltage of the electronic devices. The properties of the matrix materials, in particular, are frequently limiting for the lifetime and the efficiency of the organic electroluminescent device. In the case of matrix materials for phosphorescent emitters, it is desirable for these to have a high $T_1$ level (triplet level). This is particularly relevant in the case of matrix materials for blue-emitting phosphorescent emitters.

Furthermore, the provision of novel electron-transport materials is desirable, since the properties of the electron-transport material, in particular, also have a significant influence on the above-mentioned properties of the organic electroluminescent device. In particular, there is a need for electron-transport materials which simultaneously result in good efficiency, a long lifetime and low operating voltage.

In accordance with the prior art, carbazole derivatives, for example bis(carbazolyl)biphenyl, are frequently used as matrix materials for phosphorescent emitters. Ketones (WO 2004/093207), phosphine oxides, sulfones (WO 2005/003253), triazine compounds, such as triazinylspirobifluorene (cf. WO 2010/015306), and metal complexes, for example BAlq or zinc(II) bis[2-(2-benzothiazole)phenolate], are likewise used in this function.

The prior art likewise discloses the use of indenocarbazole derivatives as matrix materials which contain a spirobifluorene unit instead of the indenyl unit and which furthermore carry an electron-deficient heteroaryl group, for example a triazine group, on the carbazole unit (WO 2010/136109).

However, there continues to be a need for novel compounds for use as functional materials for electronic devices. In particular, there is a need for compounds for use as matrix materials or as electron-transport materials in organic electroluminescent devices. Again in particular, there is a need for compounds with which an improvement in the performance data of the electronic device can be achieved.

The present invention is thus based on the technical object of providing compounds which are suitable for use in electronic devices, such as, for example, OLEDs, and which can be employed, in particular, as matrix materials for phosphorescent emitters and/or as electron-transport materials.

The compounds in accordance with the present invention are characterised in that at least one electron-deficient group, preferably an electron-deficient heteroaryl group, is bonded to one half of the spirobifluorene skeleton, while a condensed-on heteroaryl group, preferably a condensed-on indole group, is present on the other half, which is not conjugated with the first-mentioned half. In an alternative embodiment, the compounds according to the invention are characterised in that one half of the spirobifluorene skeleton contains an electron-deficient bridge, preferably a keto bridge C=O, in its skeleton, while a condensed-on heteroaryl group, preferably a condensed-on indole group, is present on the other half, which is not conjugated with the first-mentioned half.

The invention relates to a compound of a formula (I) or (II)

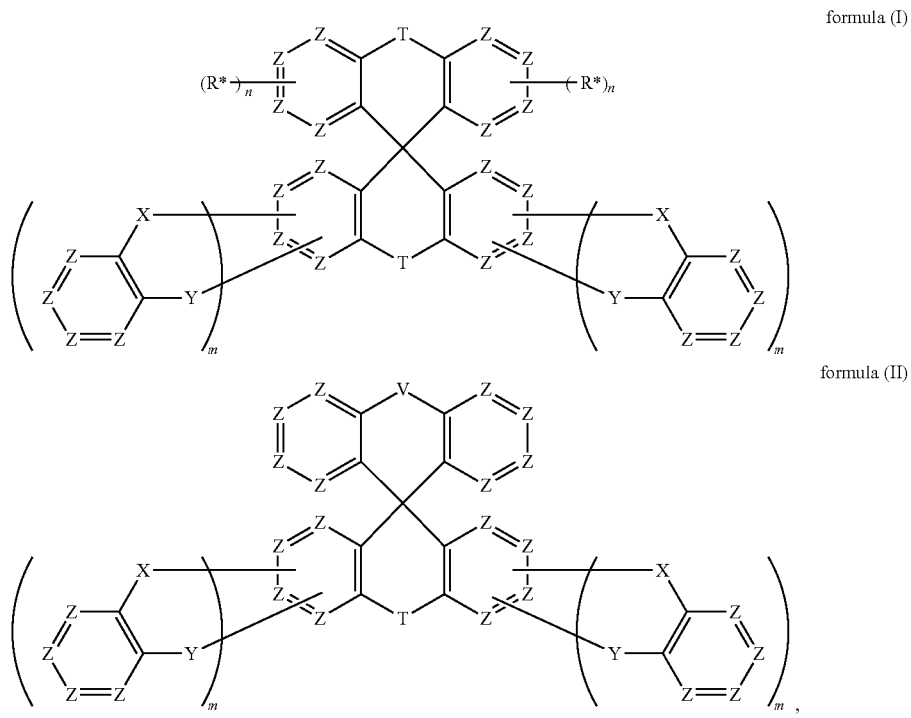

formula (I)

formula (II)

where the following applies to the symbols and indices occurring:

R* is on each occurrence, identically or differently, a heteroaryl group having 5 to 14 aromatic ring atoms or a keto group or a phosphorus oxide group or a sulfur oxide group, each of which are bonded directly or via a group L and which may be substituted by one or more radicals $R^2$, or —CN;

L is on each occurrence, identically or differently, a divalent group of the formula —$(Ar^1)_k$—, where $Ar^1$, represents on each occurrence, identically or differently, an arylene or heteroarylene group having 5 to 10 aromatic ring atoms, which may be substituted by one or more radicals $R^2$; and k is selected on each occurrence, identically or differently, from 1, 2, 3, 4 or 5;

X, Y are selected on each occurrence, identically or differently, from a single bond, $C(R^1)_2$, $NR^1$, $PR^1$, $P(O)R^1$, O, S, SO and $SO_2$, where cases in which neither of the two groups X and Y of a ring is selected from $NR^1$, $PR^1$, $P(O)R^1$, O, S, SO and $SO_2$ are excluded;

V is selected from a single bond, CO, CS, $P(O)R^1$, SO and $SO_2$, where V may only be a single bond if at least one of the groups Z in the rings bonded to V is equal to N;

T is selected on each occurrence, identically or differently, from a single bond, $C(R^1)_2$, CO, CS, $Si(R^1)_2$, $NR^1$, $PR^1$, $P(O)R^1$, O, S, SO and $SO_2$;

Z is selected on each occurrence, identically or differently, from $CR^1$ and N if no group is bonded to Z and is equal to C if a group is bonded to Z;

$R^1$ is on each occurrence, identically or differently, H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups may be replaced by —$R^2C=CR^2$—, —C≡C—, $Si(R^2)_2$, C=O, C=S, $C=NR^2$, —C(=O)O—, —C(=O)$NR^2$—, $NR^2$, $P(=O)(R^2)$, —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which may be substituted by one or more radicals $R^2$, where two or more radicals $R^1$ may be linked to one another and may form a ring;

$R^2$ is on each occurrence, identically or differently, H, D, F, Cl, Br, I, $B(OR^3)_2$, CHO, $C(=O)R^3$, $CR^3=C(R^3)_2$, CN, $C(=O)OR^3C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by —$R^3C=CR^3$—, —C≡C—, $Si(R^3)_2$, C=O, C=S, $C=NR^3$, —C(=O)O—, —C(=O)$NR^3$—, $NR^3$, $P(=O)(R^3)$, —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form a ring;

$R^3$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^3$ here may be linked to one another and may form a ring;

m is on each occurrence, identically or differently, 0 or 1, where both indices m in a formula cannot be equal to 0;

n is on each occurrence, identically or differently, 0 or 1, where both indices n in a formula cannot be equal to 0, and where the groups X and Y are each bonded in adjacent positions to the six-membered ring of the spirobifluorene derivative.

For the purposes of the present application, the following numbering of the positions on the modified spirobifluorene skeleton is used:

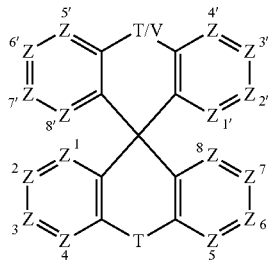

A heteroaryl group having 5 to 14 aromatic ring atoms as embodiment of R* is for the purposes of the present application preferably taken to mean an electron-deficient heteroaryl group having the said number of aromatic ring atoms. Particular preference is given to an electron-deficient heteroaryl group having 5 to 10 aromatic ring atoms. Very particular preference is given to pyridine, pyrimidine, pyridazine, pyrazine, triazine and benzimidazole.

The term "electron-deficient heteroaryl group" is taken to mean, in particular, a heteroaryl group including at least one heteroaromatic six-membered ring having one or more nitrogen atoms or at least one heteroaromatic five-membered ring having two or more nitrogen atoms.

A keto group for the purposes of the present application is taken to mean a group of the following formula (K)

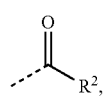

formula (K)

where the dashed bond represents the bonding position of the keto group and $R^2$ is defined as above. $R^2$ in this connection is preferably selected from an aryl or heteroaryl group having 5 to 14 aromatic ring atoms, which may be substituted by one or more radicals $R^3$. $R^2$ is particularly preferably selected from an aryl or heteroaryl group having 5 to 10 aromatic ring atoms, which may be substituted by one or more radicals $R^3$.

A phosphorus oxide group for the purposes of the present application is preferably taken to mean a group of the following formula (P)

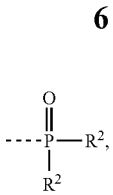

formula (P)

where the dashed bond represents the bonding site of the phosphorus oxide group and $R^2$ is as defined above. $R^2$ in this connection is preferably selected from an aryl or heteroaryl group having 5 to 14 aromatic ring atoms, which may be substituted by one or more radicals $R^3$. $R^2$ is particularly preferably selected from an aryl or heteroaryl group having 5 to 10 aromatic ring atoms, which may be substituted by one or more radicals $R^3$.

A sulfur oxide group for the purposes of the present application is taken to mean a group of the following formula (S)

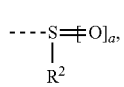

formula (S)

where the dashed bond represents the bonding site of the sulfur oxide group, a can be equal to 1 or 2, and $R^2$ is as defined above. $R^2$ in this connection is preferably selected from an aryl or heteroaryl group having 5 to 14 aromatic ring atoms, which may be substituted by one or more radicals $R^3$. $R^2$ is particularly preferably selected from an aryl or heteroaryl group having 5 to 10 aromatic ring atoms, which may be substituted by one or more radicals $R^3$.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms in, which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, nbutylthio, i-butylthio, s-butylthio, t-butylthio, n-pentylthio, s-pentylthio, nhexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present description, intended to be taken to mean, inter alia, that the two radicals are linked to one another by a chemical bond. This is illustrated by the following scheme:

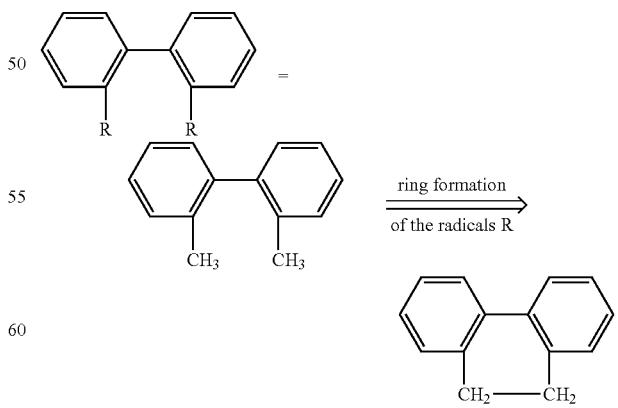

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

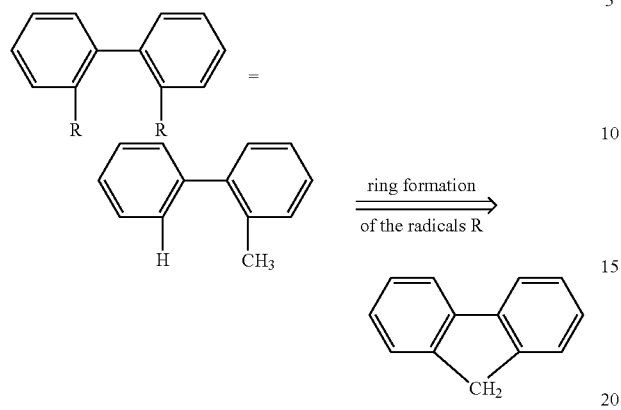

In accordance with a preferred embodiment, the compound according to the invention contains no condensed aryl groups having more than 18 aromatic ring atoms, particularly preferably no condensed aryl groups having more than 16 aromatic ring atoms, very particularly preferably no condensed aryl groups having more than 14 aromatic ring atoms, and again more preferably no condensed aryl groups having more than 10 aromatic ring atoms.

Furthermore preferably, no heteroaryl group having 6 aromatic ring atoms is bonded to the groups X and Y. Particularly preferably, no heteroaryl group, no keto group, no phosphorus oxide group and no sulfur oxide group is bonded to the groups X and Y.

In accordance with a preferred embodiment, the radical R* represents a group —CN or a group of the formula (K), (P) or (S), as described above, or a group of the formulae (H-1) to (H-10) shown below

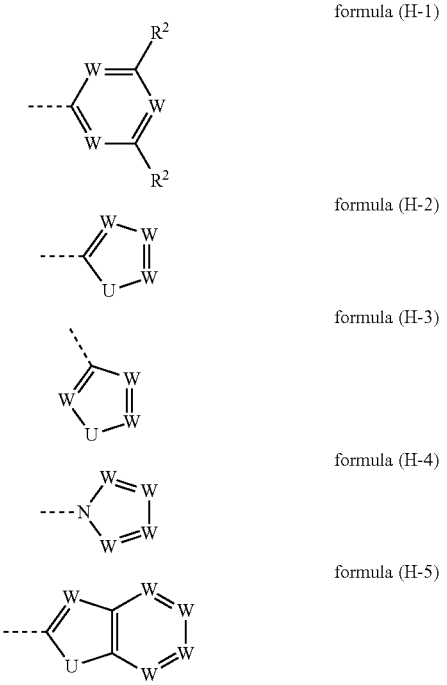

formula (H-1)

formula (H-2)

formula (H-3)

formula (H-4)

formula (H-5)

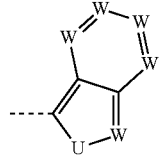

formula (H-6)

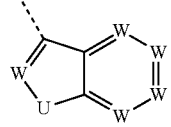

formula (H-7)

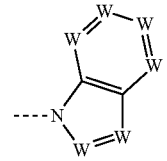

formula (H-8)

formula (H-9)

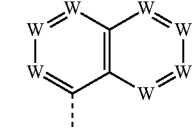

formula (H-10)

where the dashed bond marks the bonding position, $R^2$ is as defined above and

W represents on each occurrence, identically or differently, $CR^2$ or N, and

U represents $NR^2$, O or S, and where at least one group W per formula is equal to N.

R* is very particularly preferably selected from pyridine, pyrimidine, pyridazine, pyrazine, triazine and benzimidazole, each of which may be substituted by one or more radicals $R^2$.

In accordance with a preferred embodiment of the invention, no group L is present.

If a group L of the formula —$(Ar^1)_k$— is present, $Ar^1$ is preferably phenylene or a heteroarylene group having 5 to 10 aromatic ring atoms, where the said groups may each be substituted by one or more radicals $R^2$. $AR^1$ is particularly preferably ortho-, meta- or para-phenylene, each of which may be substituted by one or more radicals $R^2$. Furthermore preferably, the index k in the formula —$(Ar^1)_k$— is preferably equal to 1, 2 or 3, particularly preferably equal to 1 or 2 and very particularly preferably equal to 1.

It is furthermore preferred for the group R* to be bonded to the modified spirobifluorene skeleton in position 2' or in position 7'.

The groups X and Y are preferably selected, identically or differently, from a single bond, $C(R^1)_2$, $NR^1$, O and S, where cases in which neither of the two groups X and Y of a ring is selected from $NR^1$, O and S are excluded.

Preferred combinations of groups X and Y in a ring are shown in the following table:

| | X | Y |
|---|---|---|
| X-Y-1 | Single bond | NR$^1$ |
| X-Y-2 | Single bond | O |
| X-Y-3 | Single bond | S |
| X-Y-4 | C(R$^1$)$_2$ | NR$^1$ |
| X-Y-5 | C(R$^1$)$_2$ | O |
| X-Y-6 | C(R$^1$)$_2$ | S |
| X-Y-7 | NR$^1$ | Single bond |
| X-Y-8 | O | Single bond |
| X-Y-9 | S | Single bond |
| X-Y-10 | NR$^1$ | C(R$^1$)$_2$ |
| X-Y-11 | O | C(R$^1$)$_2$ |
| X-Y-12 | S | C(R$^1$)$_2$ |

It is furthermore preferred for precisely one of the two groups X and Y of a ring to represent a single bond, giving a five-membered ring.

It is particularly preferred for one of the two groups X and Y in a ring to represent a single bond and for the other of the two groups X and Y to represent a group NR$^1$.

It is furthermore preferred for the groups X and Y to be bonded to the modified spirobifluorene skeleton in positions 2 and 3 and/or in positions 6 and 7.

In accordance with a preferred embodiment, the group V is furthermore equal to CO.

In accordance with a preferred embodiment, the group T is furthermore selected on each occurrence, identically or differently, from a single bond, C(R$^1$)$_2$, O and S, particularly preferably from a single bond and C(R$^1$)$_2$. In accordance with a very particularly preferred embodiment, T represents a single bond.

It is furthermore preferred for no, one, two or three groups Z per aromatic six-membered ring to be equal to N, where not more than two adjacent groups Z are simultaneously equal to N. Particularly preferably not more than one group Z per aromatic six-membered ring is equal to N, very particularly preferably no group Z is equal to N.

It is furthermore preferred for R$^1$ to be selected on each occurrence, identically or differently, from H, D, F, CN, Si(R$^2$)$_3$, N(R$^2$)$_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals R$^2$ and where one or more CH$_2$ groups in the above-mentioned groups may be replaced by —C≡C—, —R$^2$C═CR$^2$—, Si(R$^2$)$_2$, C═O, C═NR$^2$, —NR$^2$—, —O—, —S—, —C(═O)O— or —C(═O)NR$^2$—, or an aromatic or heteroaromatic ring system having 5 to 18 aromatic ring atoms, which may in each case be substituted by one or more radicals R$^2$, where two or more radicals R$^1$ may be linked to one another and may form a ring.

It is furthermore preferred for R$^2$ to be selected on each occurrence, identically or differently, from H, D, F, CN, Si(R$^3$)$_3$, N(R$^3$)$_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals R$^3$ and where one or more CH$_2$ groups in the above-mentioned groups may be replaced by —C≡C—, —R$^3$C═CR$^3$—, Si(R$^3$)$_2$, C═O, C═NR$^3$, —NR$^3$—, —O—, —S—, —C(═O)O— or —C(═O)NR$^3$—, or an aromatic or heteroaromatic ring system having 5 to 18 aromatic ring atoms, which may in each case be substituted by one or more radicals R$^3$, where two or more radicals R$^2$ may be linked to one another and may form a ring.

In accordance with a preferred embodiment, one of the two indices m per formula is equal to 1 and the other is equal to 0.

In accordance with a further preferred embodiment, one of the two indices n per formula is equal to 1 and the other is equal to 0.

Preferred embodiments of the compound of the formula (I) conform to one of the following formulae (I-1) to (I-12)

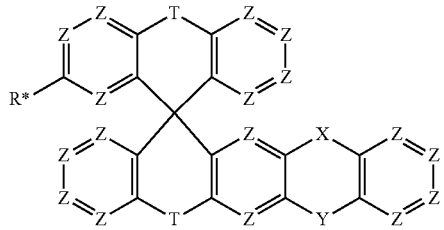

formula (I-1)

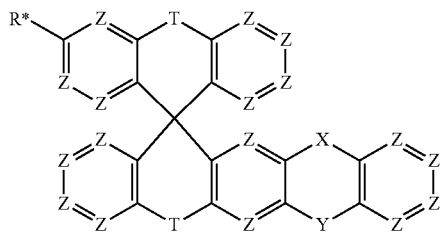

formula (I-2)

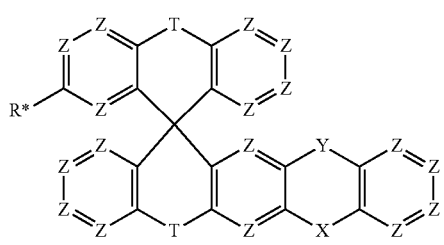

formula (I-3)

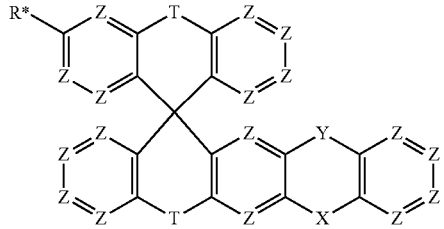

formula (I-4)

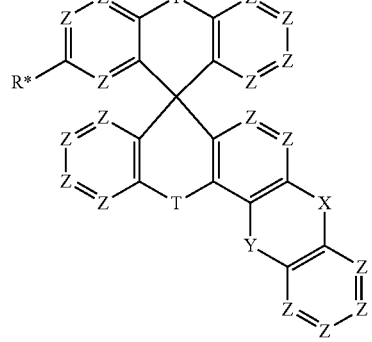

formula (I-5)

formula (I-6)
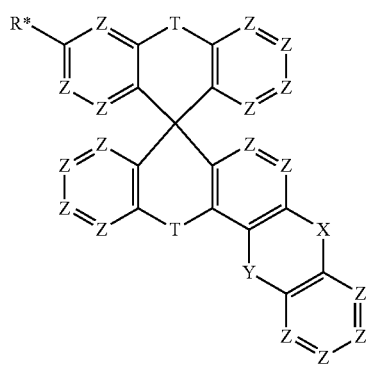

formula (I-7)
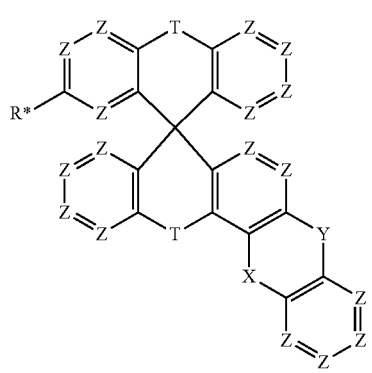

formula (I-8)
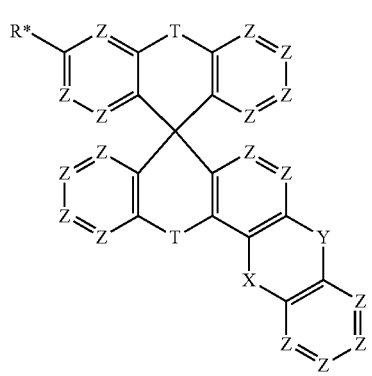

formula (I-9)
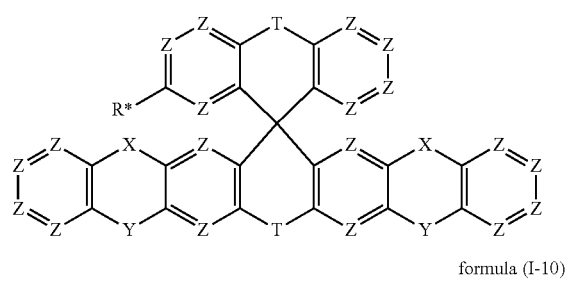

formula (I-10)
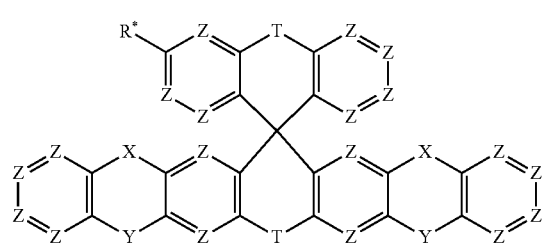

formula (I-11)
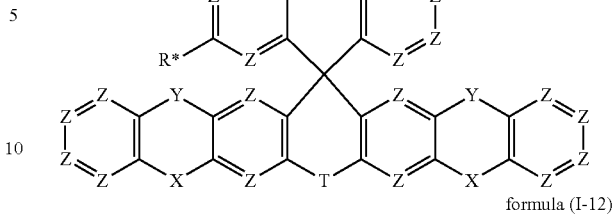

formula (I-12)
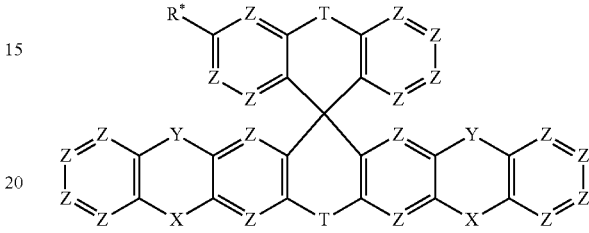

where the symbols occurring are as defined above and are preferably present in their preferred embodiments indicated above.

For the formulae (I-1) to (I-12), the group T is particularly preferably a single bond.

It is furthermore preferred for not more than one group Z per aromatic ring to be equal to N and for the other groups Z to be equal to $CR^1$. Particularly preferably, no group Z is equal to N, so that all groups Z are equal to $CR^1$.

Furthermore preferably, no heteroaryl group having 6 aromatic ring atoms is bonded to the groups X and Y in the formulae (I-1) to (I-12). Particularly preferably, no heteroaryl group, no keto group, no phosphorus oxide group and no sulfur oxide group is bonded to the groups X and Y.

For the formulae (I-1) to (I-12), preference is furthermore given to the combinations of embodiments of groups X and Y indicated in a table above.

Preference is furthermore given to the following combinations of groups R* with skeletons of the formulae (I-1) to (I-12):

| Formula | R* | L in R* | Skeleton |
|---------|-----|---------|----------|
| I-1-1 | Formula (K) | not present (n.p.) | Formula (I-1) |
| I-1-2 | see above (s.a.) | m-Ph | s.a. |
| I-1-3 | s.a. | p-Ph | s.a. |
| I-1-4 | Formula (P) | n.p. | s.a. |
| I-1-5 | s.a. | m-Ph | s.a. |
| I-1-6 | s.a. | p-Ph | s.a. |
| I-1-7 | Formula (S) | n.p. | s.a. |
| I-1-8 | s.a. | m-Ph | s.a. |
| I-1-9 | s.a. | p-Ph | s.a. |
| I-1-10 | Formula (H-1) | n.p. | s.a. |
| I-1-11 | s.a. | m-Ph | s.a. |
| I-1-12 | s.a. | p-Ph | s.a. |
| I-1-13 | Formula (H-2) | n.p. | s.a. |
| I-1-14 | s.a. | m-Ph | s.a. |
| I-1-15 | s.a. | p-Ph | s.a. |
| I-1-16 | Formula (H-3) | n.p. | s.a. |
| I-1-17 | s.a. | m-Ph | s.a. |
| I-1-18 | s.a. | p-Ph | s.a. |
| I-1-19 | Formula (H-4) | n.p. | s.a. |
| I-1-20 | s.a. | m-Ph | s.a. |
| I-1-21 | s.a. | p-Ph | s.a. |
| I-1-22 | Formula (H-5) | n.p. | s.a. |
| I-1-23 | s.a. | m-Ph | s.a. |
| I-1-24 | s.a. | p-Ph | s.a. |

| Formula | R* | L in R* | Skeleton |
|---|---|---|---|
| I-1-25 | Formula (H-6) | n.p. | s.a. |
| I-1-26 | s.a. | m-Ph | s.a. |
| I-1-27 | s.a. | p-Ph | s.a. |
| I-1-28 | Formula (H-7) | n.p. | s.a. |
| I-1-29 | s.a. | m-Ph | s.a. |
| I-1-30 | s.a. | p-Ph | s.a. |
| I-1-31 | Formula (H-8) | n.p. | s.a. |
| I-1-32 | s.a. | m-Ph | s.a. |
| I-1-33 | s.a. | p-Ph | s.a. |
| I-1-34 | Formula (H-9) | n.p. | s.a. |
| I-1-35 | s.a. | m-Ph | s.a. |
| I-1-36 | s.a. | p-Ph | s.a. |
| I-1-37 | Formula (H-10) | n.p. | s.a. |
| I-1-38 | s.a. | m-Ph | s.a. |
| I-1-39 | s.a. | p-Ph | s.a. |
| I-2-1 | Formula (K) | n.p. | Formula (I-2) |
| I-2-2 | s.a. | m-Ph | s.a. |
| I-2-3 | s.a. | p-Ph | s.a. |
| I-2-4 | Formula (P) | n.p. | s.a. |
| I-2-5 | s.a. | m-Ph | s.a. |
| I-2-6 | s.a. | p-Ph | s.a. |
| I-2-7 | Formula (S) | n.p. | s.a. |
| I-2-8 | s.a. | m-Ph | s.a. |
| I-2-9 | s.a. | p-Ph | s.a. |
| I-2-10 | Formula (H-1) | n.p. | s.a. |
| I-2-11 | s.a. | m-Ph | s.a. |
| I-2-12 | s.a. | p-Ph | s.a. |
| I-2-13 | Formula (H-2) | n.p. | s.a. |
| I-2-14 | s.a. | m-Ph | s.a. |
| I-2-15 | s.a. | p-Ph | s.a. |
| I-2-16 | Formula (H-3) | n.p. | s.a. |
| I-2-17 | s.a. | m-Ph | s.a. |
| I-2-18 | s.a. | p-Ph | s.a. |
| I-2-19 | Formula (H-4) | n.p. | s.a. |
| I-2-20 | s.a. | m-Ph | s.a. |
| I-2-21 | s.a. | p-Ph | s.a. |
| I-2-22 | Formula (H-5) | n.p. | s.a. |
| I-2-23 | s.a. | m-Ph | s.a. |
| I-2-24 | s.a. | p-Ph | s.a. |
| I-2-25 | Formula (H-6) | n.p. | s.a. |
| I-2-26 | s.a. | m-Ph | s.a. |
| I-2-27 | s.a. | p-Ph | s.a. |
| I-2-28 | Formula (H-7) | n.p. | s.a. |
| I-2-29 | s.a. | m-Ph | s.a. |
| I-2-30 | s.a. | p-Ph | s.a. |
| I-2-31 | Formula (H-8) | n.p. | s.a. |
| I-2-32 | s.a. | m-Ph | s.a. |
| I-2-33 | s.a. | p-Ph | s.a. |
| I-2-34 | Formula (H-9) | n.p. | s.a. |
| I-2-35 | s.a. | m-Ph | s.a. |
| I-2-36 | s.a. | p-Ph | s.a. |
| I-2-37 | Formula (H-10) | n.p. | s.a. |
| I-2-38 | s.a. | m-Ph | s.a. |
| I-2-39 | s.a. | p-Ph | s.a. |
| I-3-1 | Formula (K) | n.p. | Formula (I-3) |
| I-3-2 | s.a. | m-Ph | s.a. |
| I-3-3 | s.a. | p-Ph | s.a. |
| I-3-4 | Formula (P) | n.p. | s.a. |
| I-3-5 | s.a. | m-Ph | s.a. |
| I-3-6 | s.a. | p-Ph | s.a. |
| I-3-7 | Formula (S) | n.p. | s.a. |
| I-3-8 | s.a. | m-Ph | s.a. |
| I-3-9 | s.a. | p-Ph | s.a. |
| I-3-10 | Formula (H-1) | n.p. | s.a. |
| I-3-11 | s.a. | m-Ph | s.a. |
| I-3-12 | s.a. | p-Ph | s.a. |
| I-3-13 | Formula (H-2) | n.p. | s.a. |
| I-3-14 | s.a. | m-Ph | s.a. |
| I-3-15 | s.a. | p-Ph | s.a. |
| I-3-16 | Formula (H-3) | n.p. | s.a. |
| I-3-17 | s.a. | m-Ph | s.a. |
| I-3-18 | s.a. | p-Ph | s.a. |
| I-3-19 | Formula (H-4) | n.p. | s.a. |
| I-3-20 | s.a. | m-Ph | s.a. |
| I-3-21 | s.a. | p-Ph | s.a. |
| I-3-22 | Formula (H-5) | n.p. | s.a. |
| I-3-23 | s.a. | m-Ph | s.a. |
| I-3-24 | s.a. | p-Ph | s.a. |
| I-3-25 | Formula (H-6) | n.p. | s.a. |
| I-3-26 | s.a. | m-Ph | s.a. |
| I-3-27 | s.a. | p-Ph | s.a. |
| I-3-28 | Formula (H-7) | n.p. | s.a. |
| I-3-29 | s.a. | m-Ph | s.a. |
| I-3-30 | s.a. | p-Ph | s.a. |
| I-3-31 | Formula (H-8) | n.p. | s.a. |
| I-3-32 | s.a. | m-Ph | s.a. |
| I-3-33 | s.a. | p-Ph | s.a. |
| I-3-34 | Formula (H-9) | n.p. | s.a. |
| I-3-35 | s.a. | m-Ph | s.a. |
| I-3-36 | s.a. | p-Ph | s.a. |
| I-3-37 | Formula (H-10) | n.p. | s.a. |
| I-3-38 | s.a. | m-Ph | s.a. |
| I-3-39 | s.a. | p-Ph | s.a. |
| I-4-1 | Formula (K) | n.p. | Formula (I-4) |
| I-4-2 | s.a. | m-Ph | s.a. |
| I-4-3 | s.a. | p-Ph | s.a. |
| I-4-4 | Formula (P) | n.p. | s.a. |
| I-4-5 | s.a. | m-Ph | s.a. |
| I-4-6 | s.a. | p-Ph | s.a. |
| I-4-7 | Formula (S) | n.p. | s.a. |
| I-4-8 | s.a. | m-Ph | s.a. |
| I-4-9 | s.a. | p-Ph | s.a. |
| I-4-10 | Formula (H-1) | n.p. | s.a. |
| I-4-11 | s.a. | m-Ph | s.a. |
| I-4-12 | s.a. | p-Ph | s.a. |
| I-4-13 | Formula (H-2) | n.p. | s.a. |
| I-4-14 | s.a. | m-Ph | s.a. |
| I-4-15 | s.a. | p-Ph | s.a. |
| I-4-16 | Formula (H-3) | n.p. | s.a. |
| I-4-17 | s.a. | m-Ph | s.a. |
| I-4-18 | s.a. | p-Ph | s.a. |
| I-4-19 | Formula (H-4) | n.p. | s.a. |
| I-4-20 | s.a. | m-Ph | s.a. |
| I-4-21 | s.a. | p-Ph | s.a. |
| I-4-22 | Formula (H-5) | n.p. | s.a. |
| I-4-23 | s.a. | m-Ph | s.a. |
| I-4-24 | s.a. | p-Ph | s.a. |
| I-4-25 | Formula (H-6) | n.p. | s.a. |
| I-4-26 | s.a. | m-Ph | s.a. |
| I-4-27 | s.a. | p-Ph | s.a. |
| I-4-28 | Formula (H-7) | n.p. | s.a. |
| I-4-29 | s.a. | m-Ph | s.a. |
| I-4-30 | s.a. | p-Ph | s.a. |
| I-4-31 | Formula (H-8) | n.p. | s.a. |
| I-4-32 | s.a. | m-Ph | s.a. |
| I-4-33 | s.a. | p-Ph | s.a. |
| I-4-34 | Formula (H-9) | n.p. | s.a. |
| I-4-35 | s.a. | m-Ph | s.a. |
| I-4-36 | s.a. | p-Ph | s.a. |
| I-4-37 | Formula (H-10) | n.p. | s.a. |
| I-4-38 | s.a. | m-Ph | s.a. |
| I-4-39 | s.a. | p-Ph | s.a. |
| I-5-1 | Formula (K) | n.p. | Formula (I-5) |
| I-5-2 | s.a. | m-Ph | s.a. |
| I-5-3 | s.a. | p-Ph | s.a. |
| I-5-4 | Formula (P) | n.p. | s.a. |
| I-5-5 | s.a. | m-Ph | s.a. |
| I-5-6 | s.a. | p-Ph | s.a. |
| I-5-7 | Formula (S) | n.p. | s.a. |
| I-5-8 | s.a. | m-Ph | s.a. |
| I-5-9 | s.a. | p-Ph | s.a. |
| I-5-10 | Formula (H-1) | n.p. | s.a. |
| I-5-11 | s.a. | m-Ph | s.a. |
| I-5-12 | s.a. | p-Ph | s.a. |
| I-5-13 | Formula (H-2) | n.p. | s.a. |
| I-5-14 | s.a. | m-Ph | s.a. |
| I-5-15 | s.a. | p-Ph | s.a. |
| I-5-16 | Formula (H-3) | n.p. | s.a. |
| I-5-17 | s.a. | m-Ph | s.a. |
| I-5-18 | s.a. | p-Ph | s.a. |

| Formula | R* | L in R* | Skeleton |
|---|---|---|---|
| I-5-19 | Formula (H-4) | n.p. | s.a. |
| I-5-20 | s.a. | m-Ph | s.a. |
| I-5-21 | s.a. | p-Ph | s.a. |
| I-5-22 | Formula (H-5) | n.p. | s.a. |
| I-5-23 | s.a. | m-Ph | s.a. |
| I-5-24 | s.a. | p-Ph | s.a. |
| I-5-25 | Formula (H-6) | n.p. | s.a. |
| I-5-26 | s.a. | m-Ph | s.a. |
| I-5-27 | s.a. | p-Ph | s.a. |
| I-5-28 | Formula (H-7) | n.p. | s.a. |
| I-5-29 | s.a. | m-Ph | s.a. |
| I-5-30 | s.a. | p-Ph | s.a. |
| I-5-31 | Formula (H-8) | n.p. | s.a. |
| I-5-32 | s.a. | m-Ph | s.a. |
| I-5-33 | s.a. | p-Ph | s.a. |
| I-5-34 | Formula (H-9) | n.p. | s.a. |
| I-5-35 | s.a. | m-Ph | s.a. |
| I-5-36 | s.a. | p-Ph | s.a. |
| I-5-37 | Formula (H-10) | n.p. | s.a. |
| I-5-38 | s.a. | m-Ph | s.a. |
| I-5-39 | s.a. | p-Ph | s.a. |
| I-6-1 | Formula (K) | n.p. | Formula (I-6) |
| I-6-2 | s.a. | m-Ph | s.a. |
| I-6-3 | s.a. | p-Ph | s.a. |
| I-6-4 | Formula (P) | n.p. | s.a. |
| I-6-5 | s.a. | m-Ph | s.a. |
| I-6-6 | s.a. | p-Ph | s.a. |
| I-6-7 | Formula (S) | n.p. | s.a. |
| I-6-8 | s.a. | m-Ph | s.a. |
| I-6-9 | s.a. | p-Ph | s.a. |
| I-6-10 | Formula (H-1) | n.p. | s.a. |
| I-6-11 | s.a. | m-Ph | s.a. |
| I-6-12 | s.a. | p-Ph | s.a. |
| I-6-13 | Formula (H-2) | n.p. | s.a. |
| I-6-14 | s.a. | m-Ph | s.a. |
| I-6-15 | s.a. | p-Ph | s.a. |
| I-6-16 | Formula (H-3) | n.p. | s.a. |
| I-6-17 | s.a. | m-Ph | s.a. |
| I-6-18 | s.a. | p-Ph | s.a. |
| I-6-19 | Formula (H-4) | n.p. | s.a. |
| I-6-20 | s.a. | m-Ph | s.a. |
| I-6-21 | s.a. | p-Ph | s.a. |
| I-6-22 | Formula (H-5) | n.p. | s.a. |
| I-6-23 | s.a. | m-Ph | s.a. |
| I-6-24 | s.a. | p-Ph | s.a. |
| I-6-25 | Formula (H-6) | n.p. | s.a. |
| I-6-26 | s.a. | m-Ph | s.a. |
| I-6-27 | s.a. | p-Ph | s.a. |
| I-6-28 | Formula (H-7) | n.p. | s.a. |
| I-6-29 | s.a. | m-Ph | s.a. |
| I-6-30 | s.a. | p-Ph | s.a. |
| I-6-31 | Formula (H-8) | n.p. | s.a. |
| I-6-32 | s.a. | m-Ph | s.a. |
| I-6-33 | s.a. | p-Ph | s.a. |
| I-6-34 | Formula (H-9) | n.p. | s.a. |
| I-6-35 | s.a. | m-Ph | s.a. |
| I-6-36 | s.a. | p-Ph | s.a. |
| I-6-37 | Formula (H-10) | n.p. | s.a. |
| I-6-38 | s.a. | m-Ph | s.a. |
| I-6-39 | s.a. | p-Ph | s.a. |
| I-7-1 | Formula (K) | n.p. | Formula (I-7) |
| I-7-2 | s.a. | m-Ph | s.a. |
| I-7-3 | s.a. | p-Ph | s.a. |
| I-7-4 | Formula (P) | n.p. | s.a. |
| I-7-5 | s.a. | m-Ph | s.a. |
| I-7-6 | s.a. | p-Ph | s.a. |
| I-7-7 | Formula (S) | n.p. | s.a. |
| I-7-8 | s.a. | m-Ph | s.a. |
| I-7-9 | s.a. | p-Ph | s.a. |
| I-7-10 | Formula (H-1) | n.p. | s.a. |
| I-7-11 | s.a. | m-Ph | s.a. |
| I-7-12 | s.a. | p-Ph | s.a. |
| I-7-13 | Formula (H-2) | n.p. | s.a. |
| I-7-14 | s.a. | m-Ph | s.a. |
| I-7-15 | s.a. | p-Ph | s.a. |
| I-7-16 | Formula (H-3) | n.p. | s.a. |
| I-7-17 | s.a. | m-Ph | s.a. |
| I-7-18 | s.a. | p-Ph | s.a. |
| I-7-19 | Formula (H-4) | n.p. | s.a. |
| I-7-20 | s.a. | m-Ph | s.a. |
| I-7-21 | s.a. | p-Ph | s.a. |
| I-7-22 | Formula (H-5) | n.p. | s.a. |
| I-7-23 | s.a. | m-Ph | s.a. |
| I-7-24 | s.a. | p-Ph | s.a. |
| I-7-25 | Formula (H-6) | n.p. | s.a. |
| I-7-26 | s.a. | m-Ph | s.a. |
| I-7-27 | s.a. | p-Ph | s.a. |
| I-7-28 | Formula (H-7) | n.p. | s.a. |
| I-7-29 | s.a. | m-Ph | s.a. |
| I-7-30 | s.a. | p-Ph | s.a. |
| I-7-31 | Formula (H-8) | n.p. | s.a. |
| I-7-32 | s.a. | m-Ph | s.a. |
| I-7-33 | s.a. | p-Ph | s.a. |
| I-7-34 | Formula (H-9) | n.p. | s.a. |
| I-7-35 | s.a. | m-Ph | s.a. |
| I-7-36 | s.a. | p-Ph | s.a. |
| I-7-37 | Formula (H-10) | n.p. | s.a. |
| I-7-38 | s.a. | m-Ph | s.a. |
| I-7-39 | s.a. | p-Ph | s.a. |
| I-8-1 | Formula (K) | n.p. | Formula (I-8) |
| I-8-2 | s.a. | m-Ph | s.a. |
| I-8-3 | s.a. | p-Ph | s.a. |
| I-8-4 | Formula (P) | n.p. | s.a. |
| I-8-5 | s.a. | m-Ph | s.a. |
| I-8-6 | s.a. | p-Ph | s.a. |
| I-8-7 | Formula (S) | n.p. | s.a. |
| I-8-8 | s.a. | m-Ph | s.a. |
| I-8-9 | s.a. | p-Ph | s.a. |
| I-8-10 | Formula (H-1) | n.p. | s.a. |
| I-8-11 | s.a. | m-Ph | s.a. |
| I-8-12 | s.a. | p-Ph | s.a. |
| I-8-13 | Formula (H-2) | n.p. | s.a. |
| I-8-14 | s.a. | m-Ph | s.a. |
| I-8-15 | s.a. | p-Ph | s.a. |
| I-8-16 | Formula (H-3) | n.p. | s.a. |
| I-8-17 | s.a. | m-Ph | s.a. |
| I-8-18 | s.a. | p-Ph | s.a. |
| I-8-19 | Formula (H-4) | n.p. | s.a. |
| I-8-20 | s.a. | m-Ph | s.a. |
| I-8-21 | s.a. | p-Ph | s.a. |
| I-8-22 | Formula (H-5) | n.p. | s.a. |
| I-8-23 | s.a. | m-Ph | s.a. |
| I-8-24 | s.a. | p-Ph | s.a. |
| I-8-25 | Formula (H-6) | n.p. | s.a. |
| I-8-26 | s.a. | m-Ph | s.a. |
| I-8-27 | s.a. | p-Ph | s.a. |
| I-8-28 | Formula (H-7) | n.p. | s.a. |
| I-8-29 | s.a. | m-Ph | s.a. |
| I-8-30 | s.a. | p-Ph | s.a. |
| I-8-31 | Formula (H-8) | n.p. | s.a. |
| I-8-32 | s.a. | m-Ph | s.a. |
| I-8-33 | s.a. | p-Ph | s.a. |
| I-8-34 | Formula (H-9) | n.p. | s.a. |
| I-8-35 | s.a. | m-Ph | s.a. |
| I-8-36 | s.a. | p-Ph | s.a. |
| I-8-37 | Formula (H-10) | n.p. | s.a. |
| I-8-38 | s.a. | m-Ph | s.a. |
| I-8-39 | s.a. | p-Ph | s.a. |
| I-9-1 | Formula (K) | n.p. | Formula (I-9) |
| I-9-2 | s.a. | m-Ph | s.a. |
| I-9-3 | s.a. | p-Ph | s.a. |
| I-9-4 | Formula (P) | n.p. | s.a. |
| I-9-5 | s.a. | m-Ph | s.a. |
| I-9-6 | s.a. | p-Ph | s.a. |
| I-9-7 | Formula (S) | n.p. | s.a. |
| I-9-8 | s.a. | m-Ph | s.a. |
| I-9-9 | s.a. | p-Ph | s.a. |
| I-9-10 | Formula (H-1) | n.p. | s.a. |
| I-9-11 | s.a. | m-Ph | s.a. |
| I-9-12 | s.a. | p-Ph | s.a. |

| Formula | R* | L in R* | Skeleton |
|---|---|---|---|
| I-9-13 | Formula (H-2) | n.p. | s.a. |
| I-9-14 | s.a. | m-Ph | s.a. |
| I-9-15 | s.a. | p-Ph | s.a. |
| I-9-16 | Formula (H-3) | n.p. | s.a. |
| I-9-17 | s.a. | m-Ph | s.a. |
| I-9-18 | s.a. | p-Ph | s.a. |
| I-9-19 | Formula (H-4) | n.p. | s.a. |
| I-9-20 | s.a. | m-Ph | s.a. |
| I-9-21 | s.a. | p-Ph | s.a. |
| I-9-22 | Formula (H-5) | n.p. | s.a. |
| I-9-23 | s.a. | m-Ph | s.a. |
| I-9-24 | s.a. | p-Ph | s.a. |
| I-9-25 | Formula (H-6) | n.p. | s.a. |
| I-9-26 | s.a. | m-Ph | s.a. |
| I-9-27 | s.a. | p-Ph | s.a. |
| I-9-28 | Formula (H-7) | n.p. | s.a. |
| I-9-29 | s.a. | m-Ph | s.a. |
| I-9-30 | s.a. | p-Ph | s.a. |
| I-9-31 | Formula (H-8) | n.p. | s.a. |
| I-9-32 | s.a. | m-Ph | s.a. |
| I-9-33 | s.a. | p-Ph | s.a. |
| I-9-34 | Formula (H-9) | n.p. | s.a. |
| I-9-35 | s.a. | m-Ph | s.a. |
| I-9-36 | s.a. | p-Ph | s.a. |
| I-9-37 | Formula (H-10) | n.p. | s.a. |
| I-9-38 | s.a. | m-Ph | s.a. |
| I-9-39 | s.a. | p-Ph | s.a. |
| I-10-1 | Formula (K) | n.p. | Formula (I-10) |
| I-10-2 | s.a. | m-Ph | s.a. |
| I-10-3 | s.a. | p-Ph | s.a. |
| I-10-4 | Formula (P) | n.p. | s.a. |
| I-10-5 | s.a. | m-Ph | s.a. |
| I-10-6 | s.a. | p-Ph | s.a. |
| I-10-7 | Formula (S) | n.p. | s.a. |
| I-10-8 | s.a. | m-Ph | s.a. |
| I-10-9 | s.a. | p-Ph | s.a. |
| I-10-10 | Formula (H-1) | n.p. | s.a. |
| I-10-11 | s.a. | m-Ph | s.a. |
| I-10-12 | s.a. | p-Ph | s.a. |
| I-10-13 | Formula (H-2) | n.p. | s.a. |
| I-10-14 | s.a. | m-Ph | s.a. |
| I-10-15 | s.a. | p-Ph | s.a. |
| I-10-16 | Formula (H-3) | n.p. | s.a. |
| I-10-17 | s.a. | m-Ph | s.a. |
| I-10-18 | s.a. | p-Ph | s.a. |
| I-10-19 | Formula (H-4) | n.p. | s.a. |
| I-10-20 | s.a. | m-Ph | s.a. |
| I-10-21 | s.a. | p-Ph | s.a. |
| I-10-22 | Formula (H-5) | n.p. | s.a. |
| I-10-23 | s.a. | m-Ph | s.a. |
| I-10-24 | s.a. | p-Ph | s.a. |
| I-10-25 | Formula (H-6) | n.p. | s.a. |
| I-10-26 | s.a. | m-Ph | s.a. |
| I-10-27 | s.a. | p-Ph | s.a. |
| I-10-28 | Formula (H-7) | n.p. | s.a. |
| I-10-29 | s.a. | m-Ph | s.a. |
| I-10-30 | s.a. | p-Ph | s.a. |
| I-10-31 | Formula (H-8) | n.p. | s.a. |
| I-10-32 | s.a. | m-Ph | s.a. |
| I-10-33 | s.a. | p-Ph | s.a. |
| I-10-34 | Formula (H-9) | n.p. | s.a. |
| I-10-35 | s.a. | m-Ph | s.a. |
| I-10-36 | s.a. | p-Ph | s.a. |
| I-10-37 | Formula (H-10) | n.p. | s.a. |
| I-10-38 | s.a. | m-Ph | s.a. |
| I-10-39 | s.a. | p-Ph | s.a. |
| I-11-1 | Formula (K) | n.p. | Formula (I-11) |
| I-11-2 | s.a. | m-Ph | s.a. |
| I-11-3 | s.a. | p-Ph | s.a. |
| I-11-4 | Formula (P) | n.p. | s.a. |
| I-11-5 | s.a. | m-Ph | s.a. |
| I-11-6 | s.a. | p-Ph | s.a. |
| I-11-7 | Formula (S) | n.p. | s.a. |
| I-11-8 | s.a. | m-Ph | s.a. |
| I-11-9 | s.a. | p-Ph | s.a. |
| I-11-10 | Formula (H-1) | n.p. | s.a. |
| I-11-11 | s.a. | m-Ph | s.a. |
| I-11-12 | s.a. | p-Ph | s.a. |
| I-11-13 | Formula (H-2) | n.p. | s.a. |
| I-11-14 | s.a. | m-Ph | s.a. |
| I-11-15 | s.a. | p-Ph | s.a. |
| I-11-16 | Formula (H-3) | n.p. | s.a. |
| I-11-17 | s.a. | m-Ph | s.a. |
| I-11-18 | s.a. | p-Ph | s.a. |
| I-11-19 | Formula (H-4) | n.p. | s.a. |
| I-11-20 | s.a. | m-Ph | s.a. |
| I-11-21 | s.a. | p-Ph | s.a. |
| I-11-22 | Formula (H-5) | n.p. | s.a. |
| I-11-23 | s.a. | m-Ph | s.a. |
| I-11-24 | s.a. | p-Ph | s.a. |
| I-11-25 | Formula (H-6) | n.p. | s.a. |
| I-11-26 | s.a. | m-Ph | s.a. |
| I-11-27 | s.a. | p-Ph | s.a. |
| I-11-28 | Formula (H-7) | n.p. | s.a. |
| I-11-29 | s.a. | m-Ph | s.a. |
| I-11-30 | s.a. | p-Ph | s.a. |
| I-11-31 | Formula (H-8) | n.p. | s.a. |
| I-11-32 | s.a. | m-Ph | s.a. |
| I-11-33 | s.a. | p-Ph | s.a. |
| I-11-34 | Formula (H-9) | n.p. | s.a. |
| I-11-35 | s.a. | m-Ph | s.a. |
| I-11-36 | s.a. | p-Ph | s.a. |
| I-11-37 | Formula (H-10) | n.p. | s.a. |
| I-11-38 | s.a. | m-Ph | s.a. |
| I-11-39 | s.a. | p-Ph | s.a. |
| I-12-1 | Formula (K) | n.p. | Formula (I-12) |
| I-12-2 | s.a. | m-Ph | s.a. |
| I-12-3 | s.a. | p-Ph | s.a. |
| I-12-4 | Formula (P) | n.p. | s.a. |
| I-12-5 | s.a. | m-Ph | s.a. |
| I-12-6 | s.a. | p-Ph | s.a. |
| I-12-7 | Formula (S) | n.p. | s.a. |
| I-12-8 | s.a. | m-Ph | s.a. |
| I-12-9 | s.a. | p-Ph | s.a. |
| I-12-10 | Formula (H-1) | n.p. | s.a. |
| I-12-11 | s.a. | m-Ph | s.a. |
| I-12-12 | s.a. | p-Ph | s.a. |
| I-12-13 | Formula (H-2) | n.p. | s.a. |
| I-12-14 | s.a. | m-Ph | s.a. |
| I-12-15 | s.a. | p-Ph | s.a. |
| I-12-16 | Formula (H-3) | n.p. | s.a. |
| I-12-17 | s.a. | m-Ph | s.a. |
| I-12-18 | s.a. | p-Ph | s.a. |
| I-12-19 | Formula (H-4) | n.p. | s.a. |
| I-12-20 | s.a. | m-Ph | s.a. |
| I-12-21 | s.a. | p-Ph | s.a. |
| I-12-22 | Formula (H-5) | n.p. | s.a. |
| I-12-23 | s.a. | m-Ph | s.a. |
| I-12-24 | s.a. | p-Ph | s.a. |
| I-12-25 | Formula (H-6) | n.p. | s.a. |
| I-12-26 | s.a. | m-Ph | s.a. |
| I-12-27 | s.a. | p-Ph | s.a. |
| I-12-28 | Formula (H-7) | n.p. | s.a. |
| I-12-29 | s.a. | m-Ph | s.a. |
| I-12-30 | s.a. | p-Ph | s.a. |
| I-12-31 | Formula (H-8) | n.p. | s.a. |
| I-12-32 | s.a. | m-Ph | s.a. |
| I-12-33 | s.a. | p-Ph | s.a. |
| I-12-34 | Formula (H-9) | n.p. | s.a. |
| I-12-35 | s.a. | m-Ph | s.a. |
| I-12-36 | s.a. | p-Ph | s.a. |
| I-12-37 | Formula (H-10) | n.p. | s.a. |
| I-12-38 | s.a. | m-Ph | s.a. |
| I-12-39 | s.a. | p-Ph | s.a. |

The formulae indicated here and the symbols occurring therein are as defined above. Furthermore, p-Ph stands for para-phenylene and m-Ph stands for meta-phenylene.

Particularly preferred embodiments of the formula (I) are the formulae (I-1-A) to (I-12-A) indicated below formula (I-1-A)
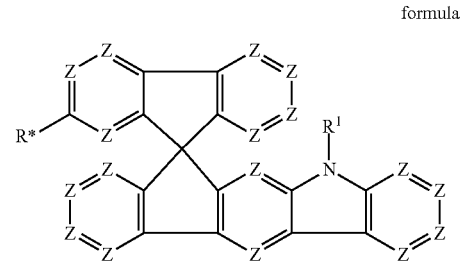
formula (I-2-A)
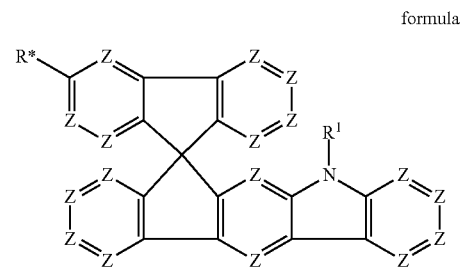
formula (I-3-A)
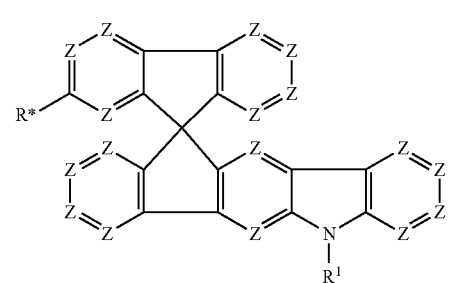
formula (I-4-A)
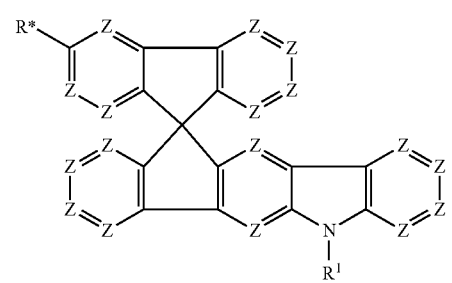
formula (I-5-A)
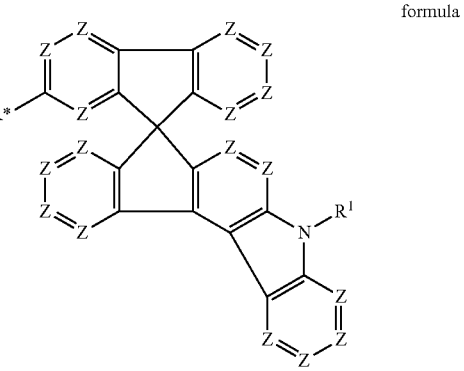
-continued
formula (I-6-A)
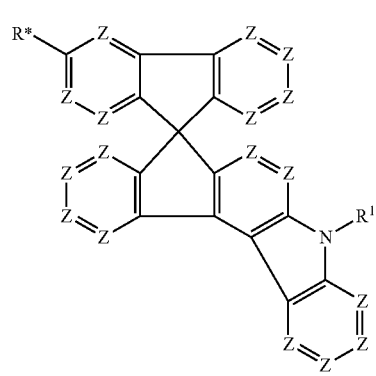
formula (I-7-A)
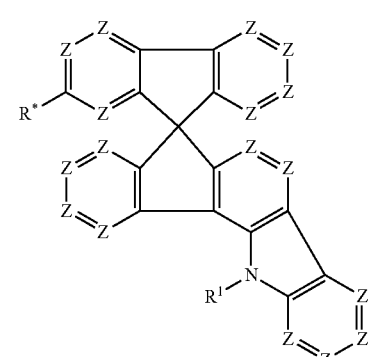
formula (I-8-A)
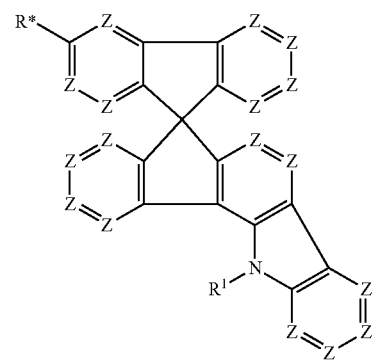
formula (I-9-A)
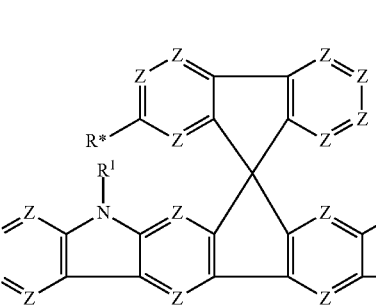

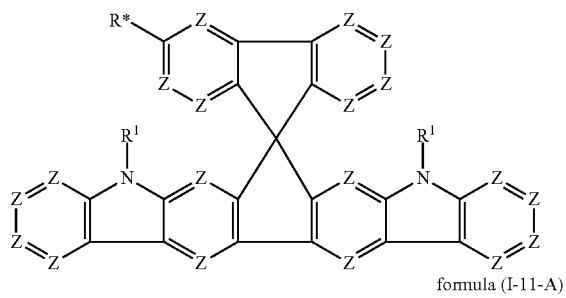

where the symbols occurring are as defined above and are preferably present in the preferred embodiments indicated above.

It is furthermore preferred for not more than one group Z per aromatic ring to be equal to N and for the other groups Z to be equal to $CR^1$. Particularly preferably, no group Z is equal to N, so that all groups Z are equal to $CR^1$.

Furthermore preferably, the radical $R^1$ which is bonded to the nitrogen atom in the formulae (I-1-A) to (I-12-A) does not represent a heteroaryl group having 6 aromatic ring atoms. This radical $R^1$ is particularly preferably not a heteroaryl group, keto group, phosphorus oxide group or sulfur oxide group.

The combinations of groups R* with skeletons of the formulae (I-1) to (I-12) indicated in a table above are identically preferred for skeletons of the formulae (I-1-A) to (I-12-A).

Preferred embodiments of the compound of the formula (II) conform to one of the following formulae (II-1) to (II-6)

where the symbols occurring are as defined above and are preferably present in their preferred embodiments indicated above.

For the formulae (II-1) to (II-6), the group T is particularly preferably a single bond or a group $C(R^1)_2$.

It is furthermore preferred for not more than one group Z per aromatic ring to be equal to N and for the other groups Z to be equal to $CR^1$. Particularly preferably, no group Z is equal to N, so that all groups Z are equal to $CR^1$.

Furthermore preferably, no heteroaryl group having 6 aromatic ring atoms is bonded to the groups X and Y in the formulae (II-1) to (II-6). Particularly preferably, no heteroaryl group, no keto group, no phosphorus oxide group and no sulfur oxide group is bonded to the groups X and Y.

For the formulae (II-1) to (II-6), preference is furthermore given to the combinations of embodiments of groups X and Y indicated in a table above.

Preference is furthermore given to the following combinations of groups R* with skeletons of the formulae (II-1) to (II-6):

| Formula | R* | L in R* | Skeleton |
|---|---|---|---|
| II-1-1 | Formula (K) | not present (n.p.) | Formula (II-1) |
| II-1-2 | see above (s.a.) | m-Ph | s.a. |
| II-1-3 | s.a. | p-Ph | s.a. |
| II-1-4 | Formula (P) | n.p. | s.a. |
| II-1-5 | s.a. | m-Ph | s.a. |
| II-1-6 | s.a. | p-Ph | s.a. |
| II-1-7 | Formula (S) | n.p. | s.a. |
| II-1-8 | s.a. | m-Ph | s.a. |
| II-1-9 | s.a. | p-Ph | s.a. |
| II-1-10 | Formula (H-1) | n.p. | s.a. |
| II-1-11 | s.a. | m-Ph | s.a. |
| II-1-12 | s.a. | p-Ph | s.a. |
| II-1-13 | Formula (H-2) | n.p. | s.a. |
| II-1-14 | s.a. | m-Ph | s.a. |
| II-1-15 | s.a. | p-Ph | s.a. |
| II-1-16 | Formula (H-3) | n.p. | s.a. |
| II-1-17 | s.a. | m-Ph | s.a. |
| II-1-18 | s.a. | p-Ph | s.a. |
| II-1-19 | Formula (H-4) | n.p. | s.a. |
| II-1-20 | s.a. | m-Ph | s.a. |
| II-1-21 | s.a. | p-Ph | s.a. |
| II-1-22 | Formula (H-5) | n.p. | s.a. |
| II-1-23 | s.a. | m-Ph | s.a. |
| II-1-24 | s.a. | p-Ph | s.a. |
| II-1-25 | Formula (H-6) | n.p. | s.a. |
| II-1-26 | s.a. | m-Ph | s.a. |
| II-1-27 | s.a. | p-Ph | s.a. |
| II-1-28 | Formula (H-7) | n.p. | s.a. |
| II-1-29 | s.a. | m-Ph | s.a. |
| II-1-30 | s.a. | p-Ph | s.a. |
| II-1-31 | Formula (H-8) | n.p. | s.a. |
| II-1-32 | s.a. | m-Ph | s.a. |
| II-1-33 | s.a. | p-Ph | s.a. |
| II-1-34 | Formula (H-9) | n.p. | s.a. |
| II-1-35 | s.a. | m-Ph | s.a. |
| II-1-36 | s.a. | p-Ph | s.a. |
| II-1-37 | Formula (H-10) | n.p. | s.a. |
| II-1-38 | s.a. | m-Ph | s.a. |
| II-1-39 | s.a. | p-Ph | s.a. |
| II-2-1 | Formula (K) | n.p. | Formula (II-2) |
| II-2-2 | s.a. | m-Ph | s.a. |
| II-2-3 | s.a. | p-Ph | s.a. |
| II-2-4 | Formula (P) | n.p. | s.a. |
| II-2-5 | s.a. | m-Ph | s.a. |
| II-2-6 | s.a. | p-Ph | s.a. |
| II-2-7 | Formula (S) | n.p. | s.a. |
| II-2-8 | s.a. | m-Ph | s.a. |
| II-2-9 | s.a. | p-Ph | s.a. |
| II-2-10 | Formula (H-1) | n.p. | s.a. |
| II-2-11 | s.a. | m-Ph | s.a. |
| II-2-12 | s.a. | p-Ph | s.a. |
| II-2-13 | Formula (H-2) | n.p. | s.a. |
| II-2-14 | s.a. | m-Ph | s.a. |
| II-2-15 | s.a. | p-Ph | s.a. |
| II-2-16 | Formula (H-3) | n.p. | s.a. |
| II-2-17 | s.a. | m-Ph | s.a. |
| II-2-18 | s.a. | p-Ph | s.a. |
| II-2-19 | Formula (H-4) | n.p. | s.a. |
| II-2-20 | s.a. | m-Ph | s.a. |
| II-2-21 | s.a. | p-Ph | s.a. |
| II-2-22 | Formula (H-5) | n.p. | s.a. |
| II-2-23 | s.a. | m-Ph | s.a. |
| II-2-24 | s.a. | p-Ph | s.a. |
| II-2-25 | Formula (H-6) | n.p. | s.a. |
| II-2-26 | s.a. | m-Ph | s.a. |
| II-2-27 | s.a. | p-Ph | s.a. |
| II-2-28 | Formula (H-7) | n.p. | s.a. |
| II-2-29 | s.a. | m-Ph | s.a. |
| II-2-30 | s.a. | p-Ph | s.a. |
| II-2-31 | Formula (H-8) | n.p. | s.a. |
| II-2-32 | s.a. | m-Ph | s.a. |
| II-2-33 | s.a. | p-Ph | s.a. |
| II-2-34 | Formula (H-9) | n.p. | s.a. |
| II-2-35 | s.a. | m-Ph | s.a. |
| II-2-36 | s.a. | p-Ph | s.a. |
| II-2-37 | Formula (H-10) | n.p. | s.a. |
| II-2-38 | s.a. | m-Ph | s.a. |
| II-2-39 | s.a. | p-Ph | s.a. |
| II-3-1 | Formula (K) | n.p. | Formula (II-3) |
| II-3-2 | s.a. | m-Ph | s.a. |
| II-3-3 | s.a. | p-Ph | s.a. |
| II-3-4 | Formula (P) | n.p. | s.a. |
| II-3-5 | s.a. | m-Ph | s.a. |
| II-3-6 | s.a. | p-Ph | s.a. |
| II-3-7 | Formula (S) | n.p. | s.a. |
| II-3-8 | s.a. | m-Ph | s.a. |
| II-3-9 | s.a. | p-Ph | s.a. |
| II-3-10 | Formula (H-1) | n.p. | s.a. |
| II-3-11 | s.a. | m-Ph | s.a. |
| II-3-12 | s.a. | p-Ph | s.a. |
| II-3-13 | Formula (H-2) | n.p. | s.a. |
| II-3-14 | s.a. | m-Ph | s.a. |
| II-3-15 | s.a. | p-Ph | s.a. |
| II-3-16 | Formula (H-3) | n.p. | s.a. |
| II-3-17 | s.a. | m-Ph | s.a. |
| II-3-18 | s.a. | p-Ph | s.a. |
| II-3-19 | Formula (H-4) | n.p. | s.a. |
| II-3-20 | s.a. | m-Ph | s.a. |
| II-3-21 | s.a. | p-Ph | s.a. |
| II-3-22 | Formula (H-5) | n.p. | s.a. |
| II-3-23 | s.a. | m-Ph | s.a. |
| II-3-24 | s.a. | p-Ph | s.a. |
| II-3-25 | Formula (H-6) | n.p. | s.a. |
| II-3-26 | s.a. | m-Ph | s.a. |
| II-3-27 | s.a. | p-Ph | s.a. |
| II-3-28 | Formula (H-7) | n.p. | s.a. |
| II-3-29 | s.a. | m-Ph | s.a. |
| II-3-30 | s.a. | p-Ph | s.a. |
| II-3-31 | Formula (H-8) | n.p. | s.a. |
| II-3-32 | s.a. | m-Ph | s.a. |
| II-3-33 | s.a. | p-Ph | s.a. |
| II-3-34 | Formula (H-9) | n.p. | s.a. |
| II-3-35 | s.a. | m-Ph | s.a. |
| II-3-36 | s.a. | p-Ph | s.a. |
| II-3-37 | Formula (H-10) | n.p. | s.a. |
| II-3-38 | s.a. | m-Ph | s.a. |
| II-3-39 | s.a. | p-Ph | s.a. |
| II-4-1 | Formula (K) | n.p. | Formula (II-4) |
| II-4-2 | s.a. | m-Ph | s.a. |
| II-4-3 | s.a. | p-Ph | s.a. |
| II-4-4 | Formula (P) | n.p. | s.a. |
| II-4-5 | s.a. | m-Ph | s.a. |
| II-4-6 | s.a. | p-Ph | s.a. |

-continued

| Formula | R* | L in R* | Skeleton |
|---|---|---|---|
| II-4-7 | Formula (S) | n.p. | s.a. |
| II-4-8 | s.a. | m-Ph | s.a. |
| II-4-9 | s.a. | p-Ph | s.a. |
| II-4-10 | Formula (H-1) | n.p. | s.a. |
| II-4-11 | s.a. | m-Ph | s.a. |
| II-4-12 | s.a. | p-Ph | s.a. |
| II-4-13 | Formula (H-2) | n.p. | s.a. |
| II-4-14 | s.a. | m-Ph | s.a. |
| II-4-15 | s.a. | p-Ph | s.a. |
| II-4-16 | Formula (H-3) | n.p. | s.a. |
| II-4-17 | s.a. | m-Ph | s.a. |
| II-4-18 | s.a. | p-Ph | s.a. |
| II-4-19 | Formula (H-4) | n.p. | s.a. |
| II-4-20 | s.a. | m-Ph | s.a. |
| II-4-21 | s.a. | p-Ph | s.a. |
| II-4-22 | Formula (H-5) | n.p. | s.a. |
| II-4-23 | s.a. | m-Ph | s.a. |
| II-4-24 | s.a. | p-Ph | s.a. |
| II-4-25 | Formula (H-6) | n.p. | s.a. |
| II-4-26 | s.a. | m-Ph | s.a. |
| II-4-27 | s.a. | p-Ph | s.a. |
| II-4-28 | Formula (H-7) | n.p. | s.a. |
| II-4-29 | s.a. | m-Ph | s.a. |
| II-4-30 | s.a. | p-Ph | s.a. |
| II-4-31 | Formula (H-8) | n.p. | s.a. |
| II-4-32 | s.a. | m-Ph | s.a. |
| II-4-33 | s.a. | p-Ph | s.a. |
| II-4-34 | Formula (H-9) | n.p. | s.a. |
| II-4-35 | s.a. | m-Ph | s.a. |
| II-4-36 | s.a. | p-Ph | s.a. |
| II-4-37 | Formula (H-10) | n.p. | s.a. |
| II-4-38 | s.a. | m-Ph | s.a. |
| II-4-39 | s.a. | p-Ph | s.a. |
| II-5-1 | Formula (K) | n.p. | Formula (II-5) |
| II-5-2 | s.a. | m-Ph | s.a. |
| II-5-3 | s.a. | p-Ph | s.a. |
| II-5-4 | Formula (P) | n.p. | s.a. |
| II-5-5 | s.a. | m-Ph | s.a. |
| II-5-6 | s.a. | p-Ph | s.a. |
| II-5-7 | Formula (S) | n.p. | s.a. |
| II-5-8 | s.a. | m-Ph | s.a. |
| II-5-9 | s.a. | p-Ph | s.a. |
| II-5-10 | Formula (H-1) | n.p. | s.a. |
| II-5-11 | s.a. | m-Ph | s.a. |
| II-5-12 | s.a. | p-Ph | s.a. |
| II-5-13 | Formula (H-2) | n.p. | s.a. |
| II-5-14 | s.a. | m-Ph | s.a. |
| II-5-15 | s.a. | p-Ph | s.a. |
| II-5-16 | Formula (H-3) | n.p. | s.a. |
| II-5-17 | s.a. | m-Ph | s.a. |
| II-5-18 | s.a. | p-Ph | s.a. |
| II-5-19 | Formula (H-4) | n.p. | s.a. |
| II-5-20 | s.a. | m-Ph | s.a. |
| II-5-21 | s.a. | p-Ph | s.a. |
| II-5-22 | Formula (H-5) | n.p. | s.a. |
| II-5-23 | s.a. | m-Ph | s.a. |
| II-5-24 | s.a. | p-Ph | s.a. |
| II-5-25 | Formula (H-6) | n.p. | s.a. |
| II-5-26 | s.a. | m-Ph | s.a. |
| II-5-27 | s.a. | p-Ph | s.a. |
| II-5-28 | Formula (H-7) | n.p. | s.a. |
| II-5-29 | s.a. | m-Ph | s.a. |
| II-5-30 | s.a. | p-Ph | s.a. |
| II-5-31 | Formula (H-8) | n.p. | s.a. |
| II-5-32 | s.a. | m-Ph | s.a. |
| II-5-33 | s.a. | p-Ph | s.a. |
| II-5-34 | Formula (H-9) | n.p. | s.a. |
| II-5-35 | s.a. | m-Ph | s.a. |
| II-5-36 | s.a. | p-Ph | s.a. |
| II-5-37 | Formula (H-10) | n.p. | s.a. |
| II-5-38 | s.a. | m-Ph | s.a. |
| II-5-39 | s.a. | p-Ph | s.a. |
| II-6-1 | Formula (K) | n.p. | Formula (II-6) |
| II-6-2 | s.a. | m-Ph | s.a. |
| II-6-3 | s.a. | p-Ph | s.a. |
| II-6-4 | Formula (P) | n.p. | s.a. |
| II-6-5 | s.a. | m-Ph | s.a. |
| II-6-6 | s.a. | p-Ph | s.a. |
| II-6-7 | Formula (S) | n.p. | s.a. |
| II-6-8 | s.a. | m-Ph | s.a. |
| II-6-9 | s.a. | p-Ph | s.a. |
| II-6-10 | Formula (H-1) | n.p. | s.a. |
| II-6-11 | s.a. | m-Ph | s.a. |
| II-6-12 | s.a. | p-Ph | s.a. |
| II-6-13 | Formula (H-2) | n.p. | s.a. |
| II-6-14 | s.a. | m-Ph | s.a. |
| II-6-15 | s.a. | p-Ph | s.a. |
| II-6-16 | Formula (H-3) | n.p. | s.a. |
| II-6-17 | s.a. | m-Ph | s.a. |
| II-6-18 | s.a. | p-Ph | s.a. |
| II-6-19 | Formula (H-4) | n.p. | s.a. |
| II-6-20 | s.a. | m-Ph | s.a. |
| II-6-21 | s.a. | p-Ph | s.a. |
| II-6-22 | Formula (H-5) | n.p. | s.a. |
| II-6-23 | s.a. | m-Ph | s.a. |
| II-6-24 | s.a. | p-Ph | s.a. |
| II-6-25 | Formula (H-6) | n.p. | s.a. |
| II-6-26 | s.a. | m-Ph | s.a. |
| II-6-27 | s.a. | p-Ph | s.a. |
| II-6-28 | Formula (H-7) | n.p. | s.a. |
| II-6-29 | s.a. | m-Ph | s.a. |
| II-6-30 | s.a. | p-Ph | s.a. |
| II-6-31 | Formula (H-8) | n.p. | s.a. |
| II-6-32 | s.a. | m-Ph | s.a. |
| II-6-33 | s.a. | p-Ph | s.a. |
| II-6-34 | Formula (H-9) | n.p. | s.a. |
| II-6-35 | s.a. | m-Ph | s.a. |
| II-6-36 | s.a. | p-Ph | s.a. |
| II-6-37 | Formula (H-10) | n.p. | s.a. |
| II-6-38 | s.a. | m-Ph | s.a. |
| II-6-39 | s.a. | p-Ph | s.a. |

The formulae indicated here and the symbols occurring therein are as defined above. Furthermore, p-Ph stands for para-phenylene and m-Ph stands for meta-phenylene.

Particularly preferred embodiments of the formula (I) are the formulae (II-1-A) to (II-6-A) indicated below formua (II-1-A)

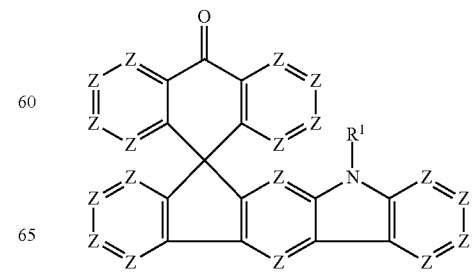

formula (II-2-A)

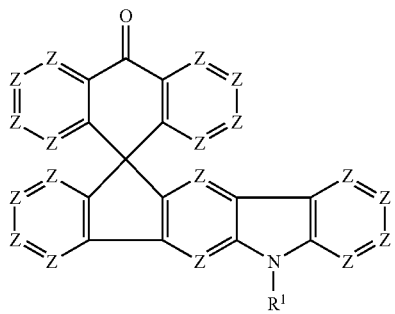

formula (II-3-A)

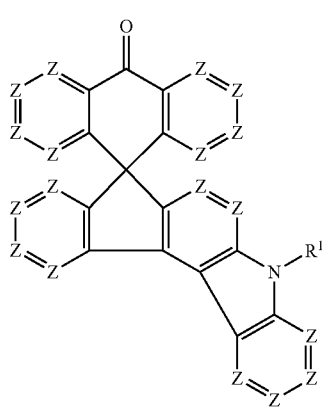

formula (II-4-A)

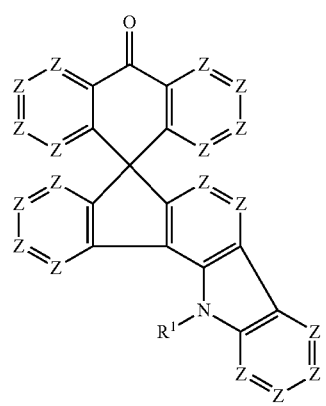

formula (II-5-A)

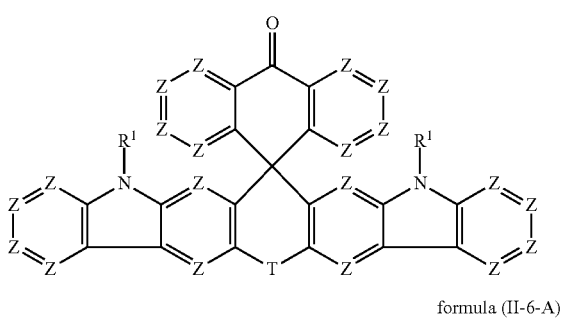

formula (II-6-A)

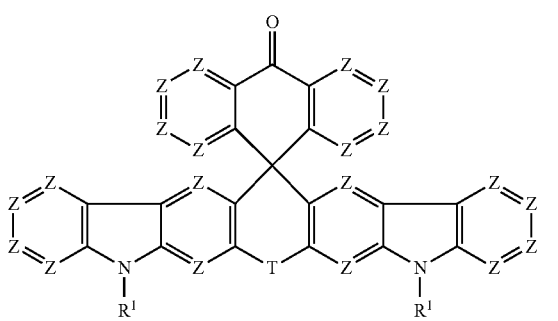

where the symbols occurring are as defined above and are preferably present in the preferred embodiments indicated above.

It is furthermore preferred for not more than one group Z per aromatic ring to be equal to N and for the other groups Z to be equal to $CR^1$. Particularly preferably, no group Z is equal to N, so that all groups Z are equal to $CR^1$.

Furthermore preferably, the radical $R^1$ which is bonded to the nitrogen atom in the formulae (II-1-A) to (II-6-A) does not represent a heteroaryl group having 6 aromatic ring atoms. This radical $R^1$ is particularly preferably not a heteroaryl group, keto group, phosphorus oxide group or sulfur oxide group.

The combinations of groups R* with skeletons of the formulae (II-1) to (II-6) indicated in a table above are identically preferred for skeletons of the formulae (II-1-A) to (II-6-A).

Examples of compounds of the formula (I) or (II) are given in the following table:

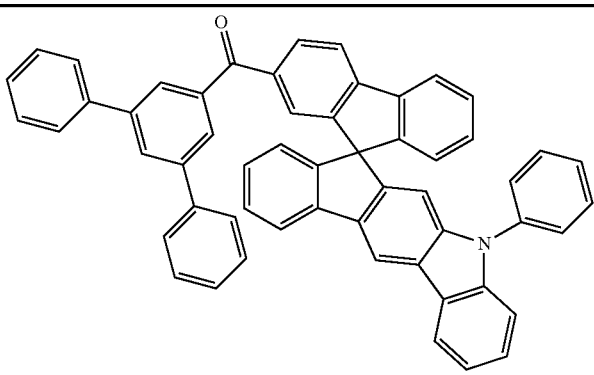

1

-continued
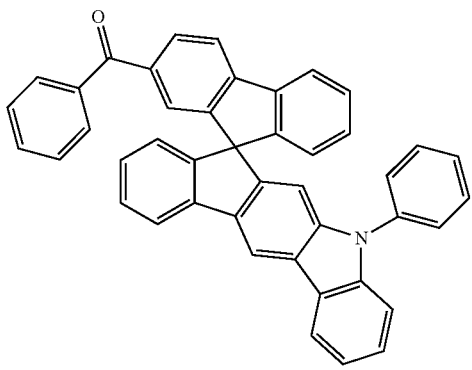 [SMILES: O=C(c1ccccc1)c1ccc2c(c1)C1(c3ccccc3-2)c2ccccc2-c2cc3c4ccccc4n(-c4ccccc4)c3cc21]
2
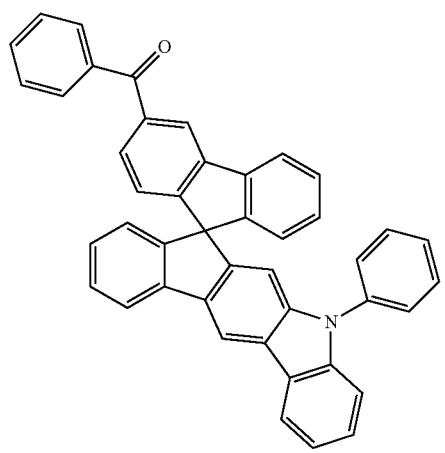 [SMILES: O=C(c1ccccc1)c1ccc2c(c1)-c1ccccc1C21c2ccccc2-c2cc3c4ccccc4n(-c4ccccc4)c3cc21]
3
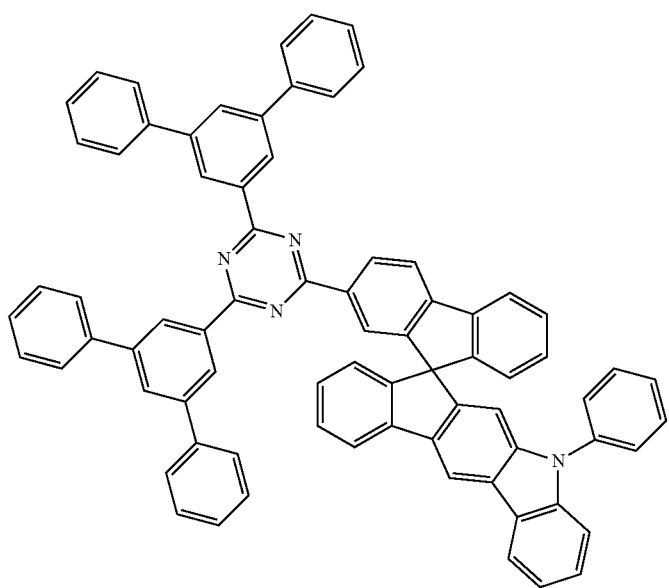 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-5)c5ccccc5-c5cc6c7ccccc7n(-c7ccccc7)c6cc54)n3)c2)cc1]
4

-continued
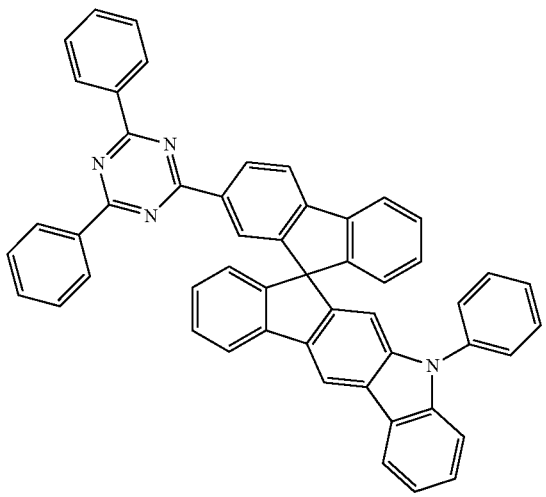 [SMILES: c1ccc(-c2nc(-c3ccccc3)nc(-c3ccc4c(c3)C3(c5ccccc5-4)c4ccccc4-c4cc5c6ccccc6n(-c6ccccc6)c5cc43)n2)cc1]
5
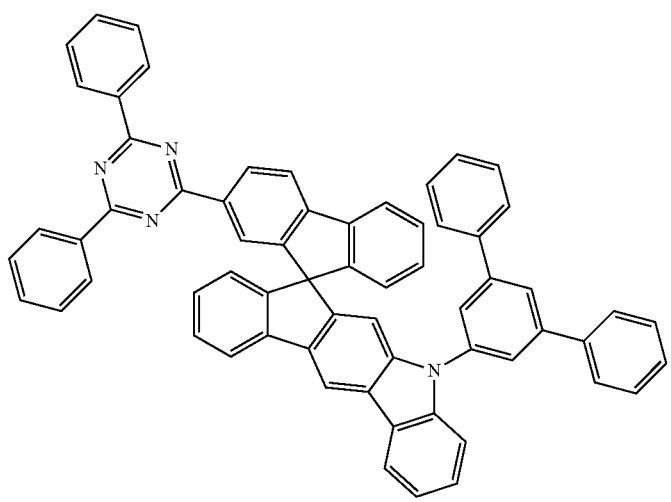 [SMILES: c1ccc(-c2cc(-c3ccccc3)cc(-n3c4ccccc4c4cc5c(cc43)C3(c4ccccc4-c4ccc(-c6nc(-c7ccccc7)nc(-c7ccccc7)n6)cc43)c3ccccc3-5)c2)cc1]
6
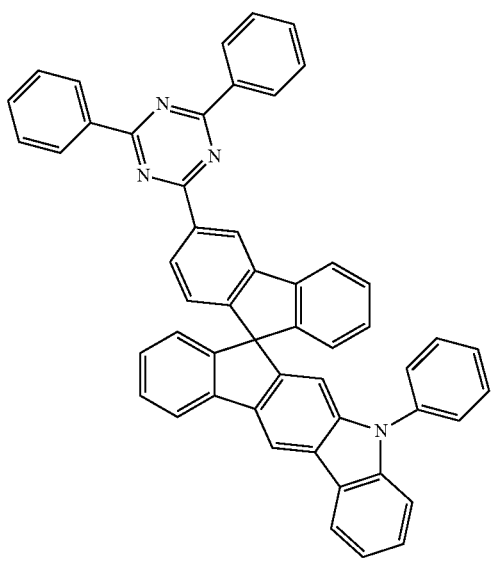 [SMILES: c1ccc(-c2nc(-c3ccccc3)nc(-c3ccc4c(c3)-c3ccccc3C43c4ccccc4-c4cc5c6ccccc6n(-c6ccccc6)c5cc43)n2)cc1]
7

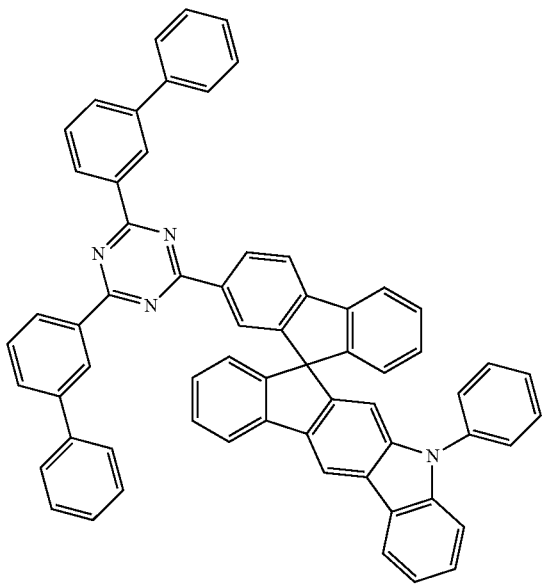 [SMILES: c1ccc(-c2cccc(-c3nc(-c4cccc(-c5ccccc5)c4)nc(-c4ccc5c(c4)C4(c6ccccc6-5)c5ccccc5-c5cc6c7ccccc7n(-c7ccccc7)c6cc54)n3)c2)cc1]
8
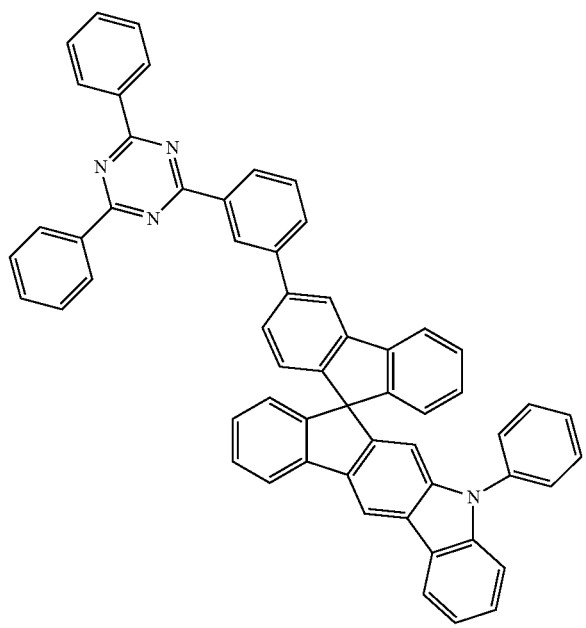 [SMILES: c1ccc(-c2nc(-c3ccccc3)nc(-c3cccc(-c4ccc5c(c4)-c4ccccc4C54c5ccccc5-c5cc6c7ccccc7n(-c7ccccc7)c6cc54)c3)n2)cc1]
9

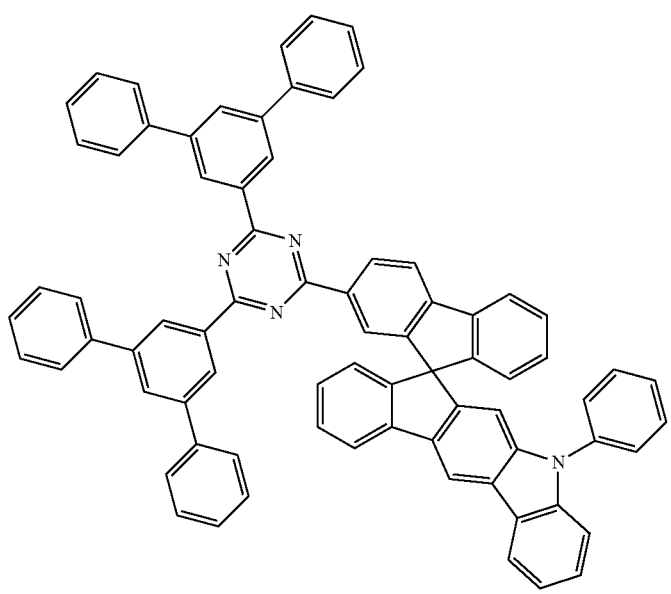 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-5)c5ccccc5-c5cc6c7ccccc7n(-c7ccccc7)c6cc54)n3)c2)cc1]
10
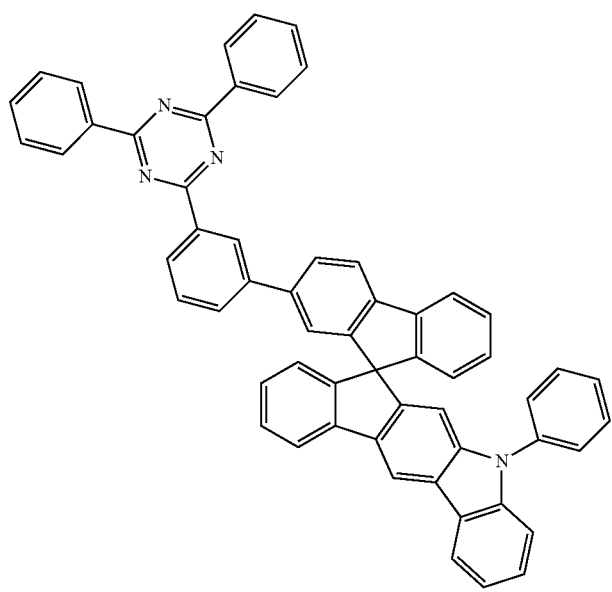 [SMILES: c1ccc(-c2nc(-c3ccccc3)nc(-c3cccc(-c4ccc5c(c4)C4(c6ccccc6-5)c5ccccc5-c5cc6c7ccccc7n(-c7ccccc7)c6cc54)c3)n2)cc1]
11

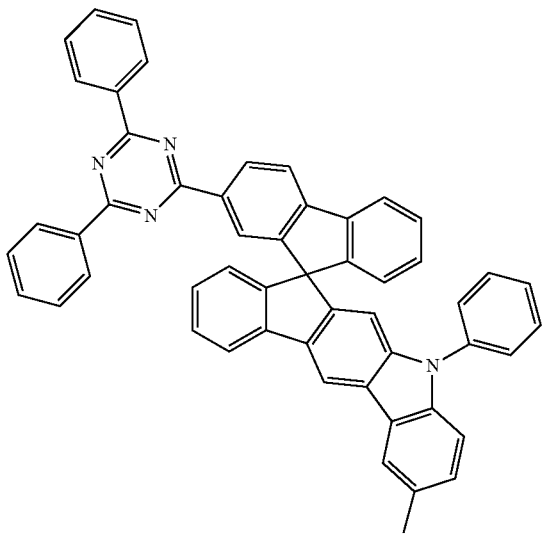 [SMILES: Cc1ccc2c(c1)c1cc3c(cc1n2-c1ccccc1)C1(c2ccccc2-c2ccc(-c4nc(-c5ccccc5)nc(-c5ccccc5)n4)cc21)c1ccccc1-3]
12
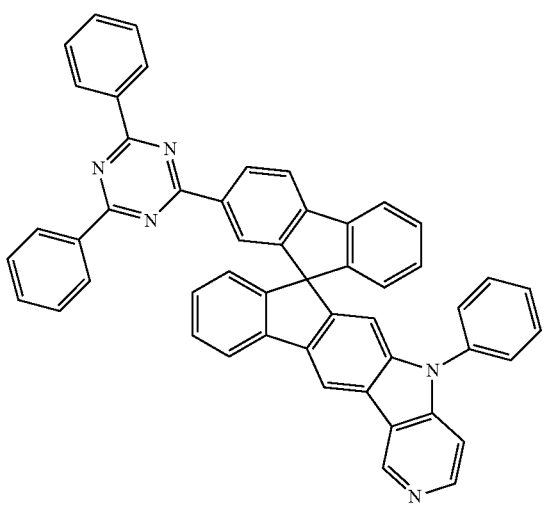 [SMILES: c1ccc(-c2nc(-c3ccccc3)nc(-c3ccc4c(c3)C3(c5ccccc5-4)c4ccccc4-c4cc5c6cnccc6n(-c6ccccc6)c5cc43)n2)cc1]
13
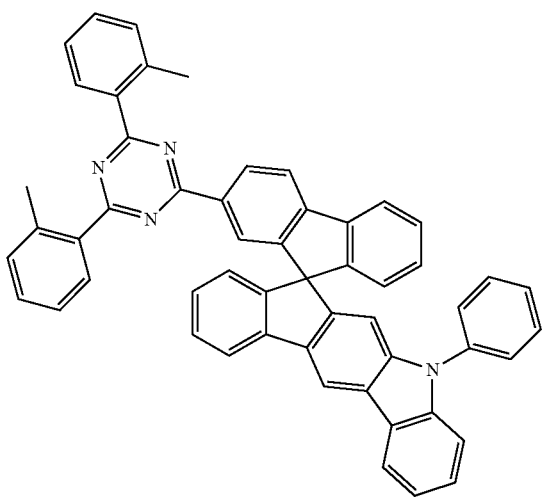 [SMILES: Cc1ccccc1-c1nc(-c2ccc3c(c2)C2(c4ccccc4-3)c3ccccc3-c3cc4c5ccccc5n(-c5ccccc5)c4cc32)nc(-c2ccccc2C)n1]
14

-continued
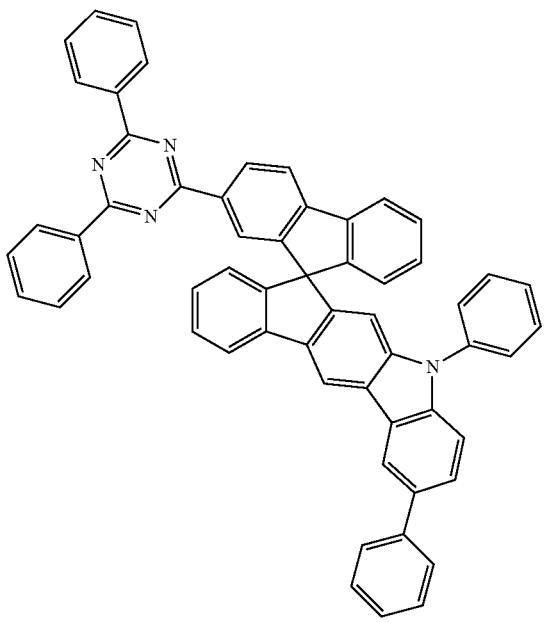 [SMILES: c1ccc(-c2ccc3c(c2)c2cc4c(cc2n3-c2ccccc2)C2(c3ccccc3-c3ccc(-c5nc(-c6ccccc6)nc(-c6ccccc6)n5)cc32)c2ccccc2-4)cc1]
15
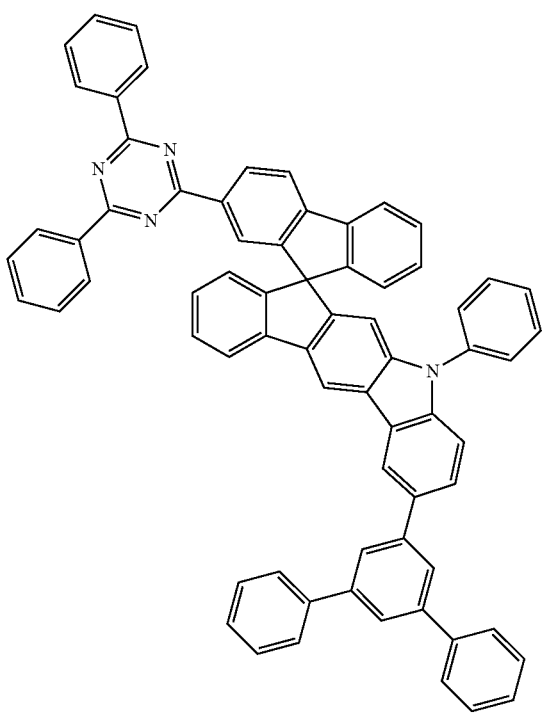 [SMILES: c1ccc(-c2cc(-c3ccccc3)cc(-c3ccc4c(c3)c3cc5c(cc3n4-c3ccccc3)C3(c4ccccc4-c4ccc(-c6nc(-c7ccccc7)nc(-c7ccccc7)n6)cc43)c3ccccc3-5)c2)cc1]
16

-continued
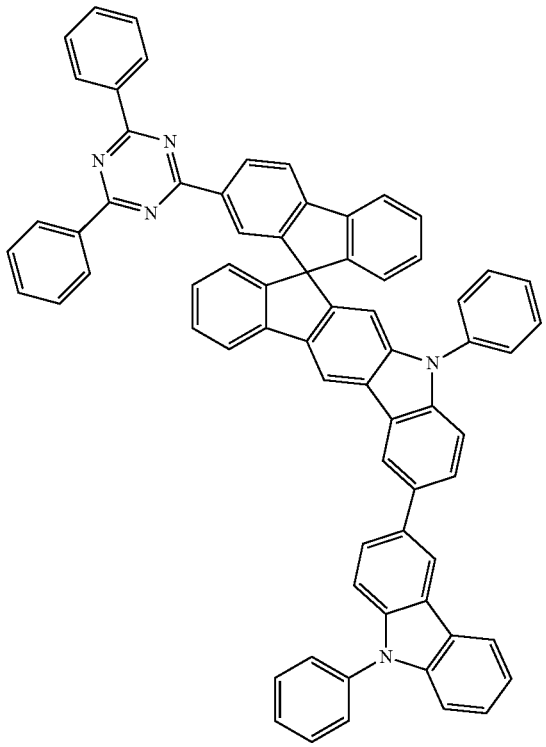 [SMILES: c1ccc(-c2nc(-c3ccccc3)nc(-c3ccc4c(c3)C3(c5ccccc5-4)c4ccccc4-c4cc5c6cc(-c7ccc8c(c7)c7ccccc7n8-c7ccccc7)ccc6n(-c6ccccc6)c5cc43)n2)cc1]
17
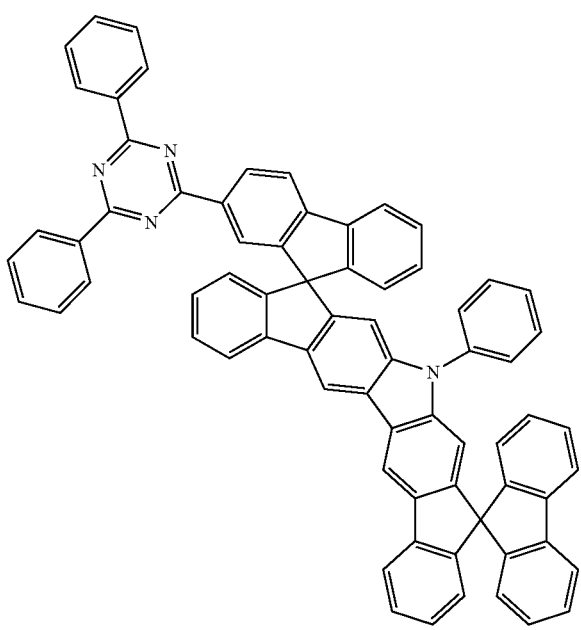 [SMILES: c1ccc(-c2nc(-c3ccccc3)nc(-c3ccc4c(c3)C3(c5ccccc5-4)c4ccccc4-c4cc5c6cc7c(cc6n(-c6ccccc6)c5cc43)C3(c4ccccc4-c4ccccc43)c3ccccc3-7)n2)cc1]
18

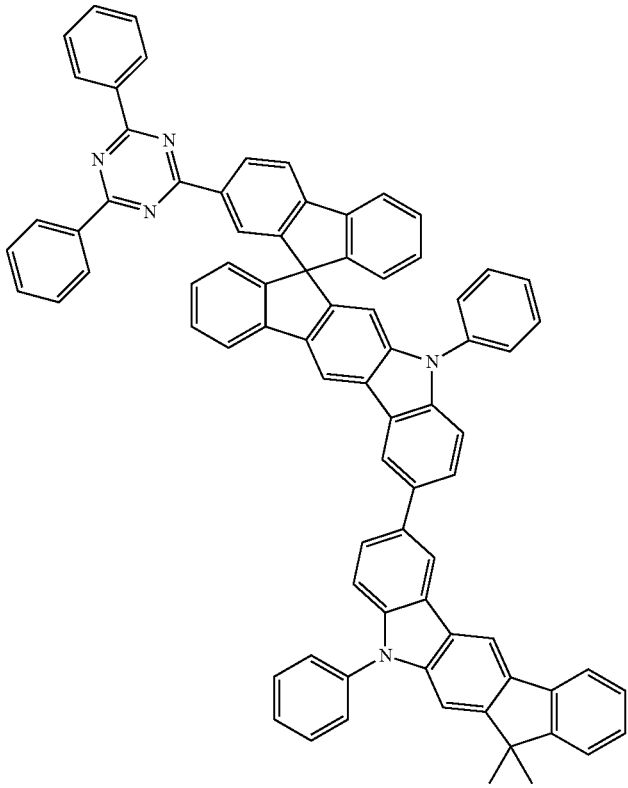 [SMILES: CC1(C)c2ccccc2-c2cc3c4cc(-c5ccc6c(c5)c5cc7c(cc5n6-c5ccccc5)C5(c6ccccc6-c6ccc(-c8nc(-c9ccccc9)nc(-c9ccccc9)n8)cc65)c5ccccc5-7)ccc4n(-c4ccccc4)c3cc21]
19
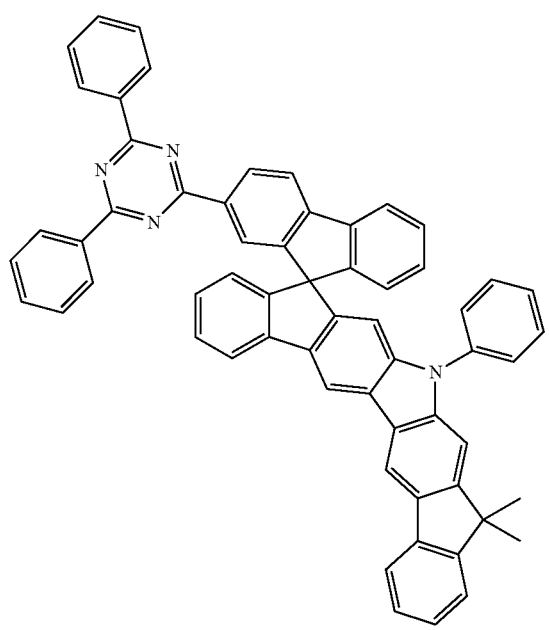 [SMILES: CC1(C)c2ccccc2-c2cc3c4cc5c(cc4n(-c4ccccc4)c3cc21)C1(c2ccccc2-c2ccc(-c3nc(-c4ccccc4)nc(-c4ccccc4)n3)cc21)c1ccccc1-5]
20

-continued
21
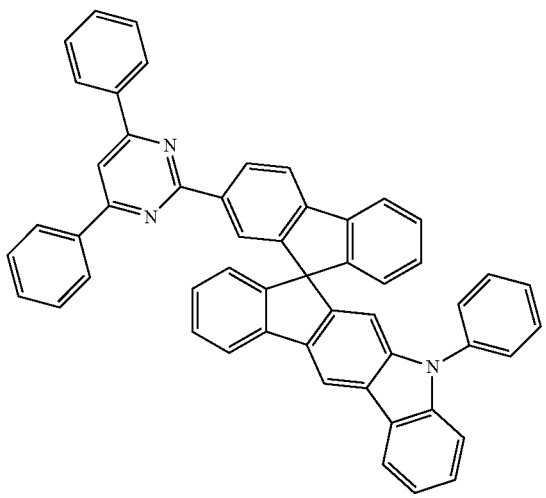
22
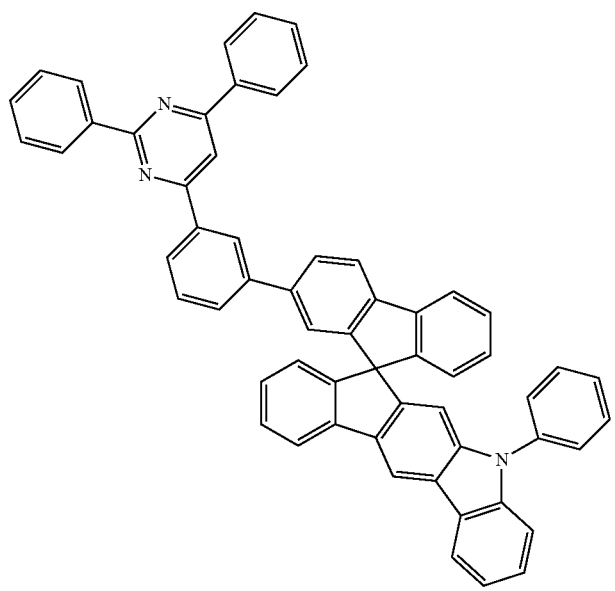
23
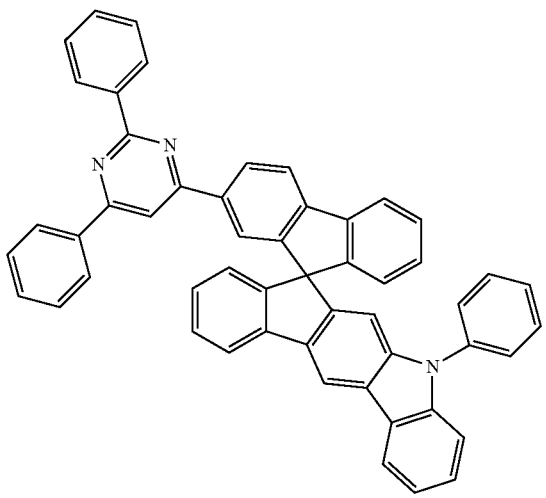 [SMILES: c1ccc(-c2cc(-c3ccc4c(c3)C3(c5ccccc5-4)c4ccccc4-c4cc5c6ccccc6n(-c6ccccc6)c5cc43)nc(-c3ccccc3)n2)cc1]

-continued
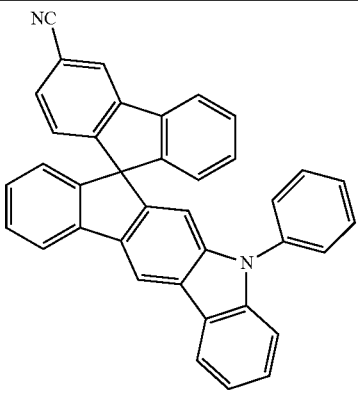
24
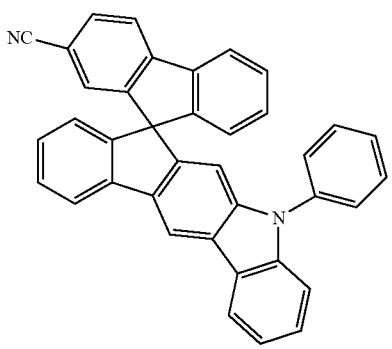 [SMILES: N#Cc1ccc2c(c1)C1(c3ccccc3-2)c2ccccc2-c2cc3c4ccccc4n(-c4ccccc4)c3cc21]
25
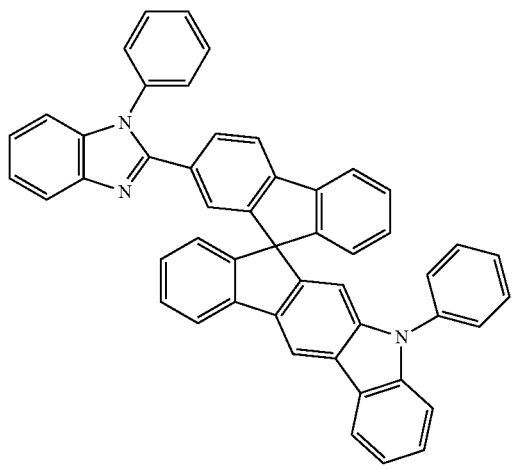 [SMILES: c1ccc(-n2c(-c3ccc4c(c3)C3(c5ccccc5-4)c4ccccc4-c4cc5c6ccccc6n(-c6ccccc6)c5cc43)nc3ccccc32)cc1]
26

-continued
27
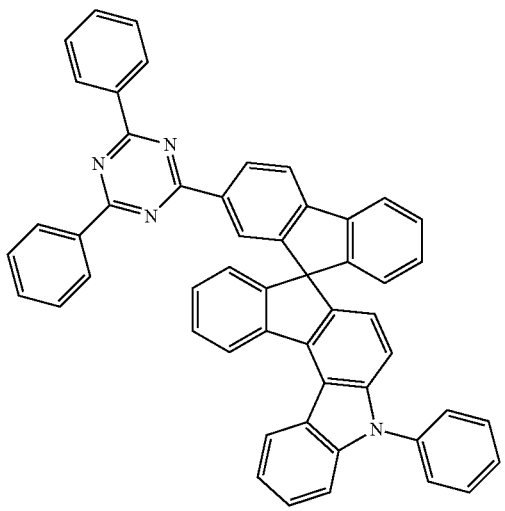 [SMILES: c1ccc(-c2nc(-c3ccccc3)nc(-c3ccc4c(c3)C3(c5ccccc5-4)c4ccccc4-c4c3ccc3c4c4ccccc4n3-c3ccccc3)n2)cc1]
28
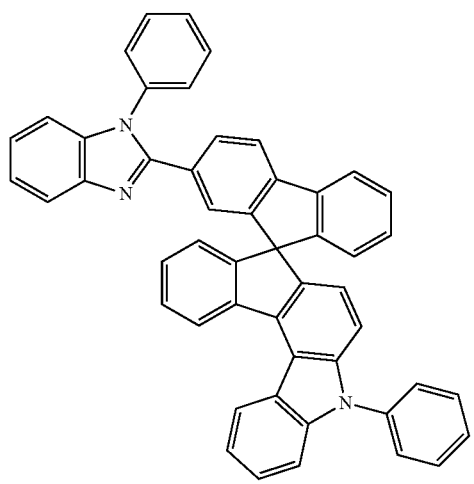 [SMILES: c1ccc(-n2c(-c3ccc4c(c3)C3(c5ccccc5-4)c4ccccc4-c4c3ccc3c4c4ccccc4n3-c3ccccc3)nc3ccccc32)cc1]
29
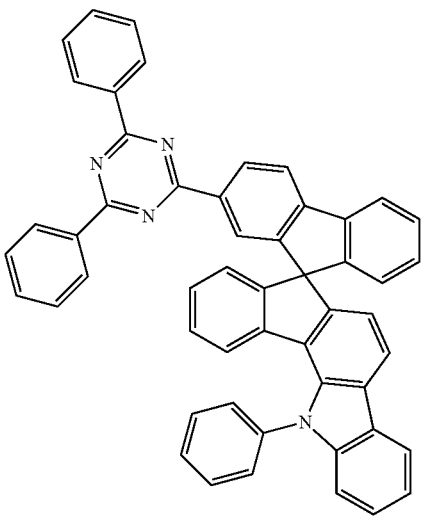 [SMILES: c1ccc(-c2nc(-c3ccccc3)nc(-c3ccc4c(c3)C3(c5ccccc5-4)c4ccccc4-c4c3ccc3c5ccccc5n(-c5ccccc5)c43)n2)cc1]

-continued
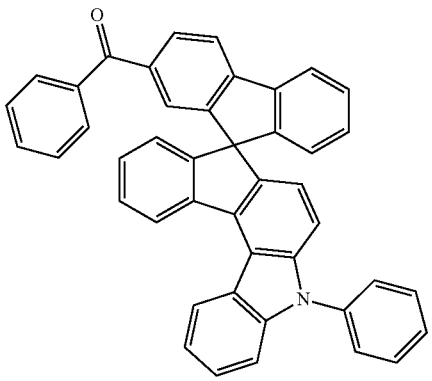 [SMILES: O=C(c1ccccc1)c1ccc2c(c1)C1(c3ccccc3-2)c2ccccc2-c2c1ccc1c2c2ccccc2n1-c1ccccc1]
30
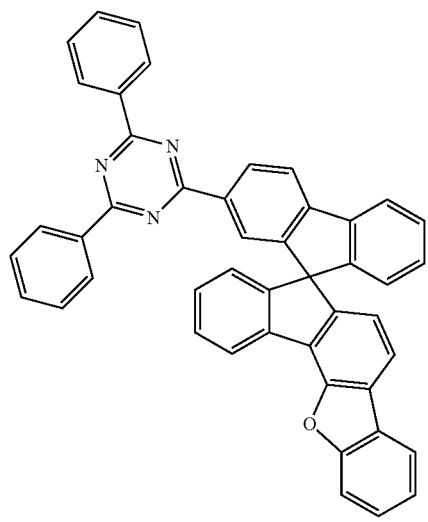 [SMILES: c1ccc(-c2nc(-c3ccccc3)nc(-c3ccc4c(c3)C3(c5ccccc5-4)c4ccccc4-c4c3ccc3c4oc4ccccc43)n2)cc1]
31
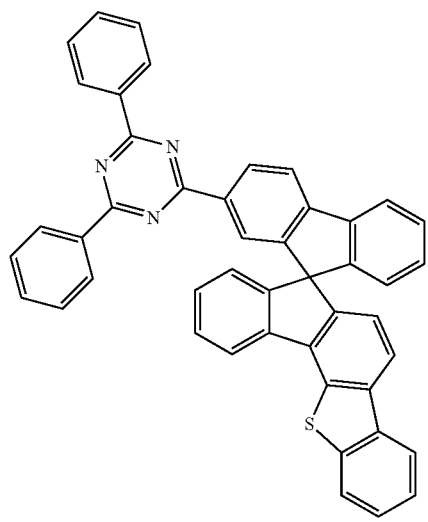
32

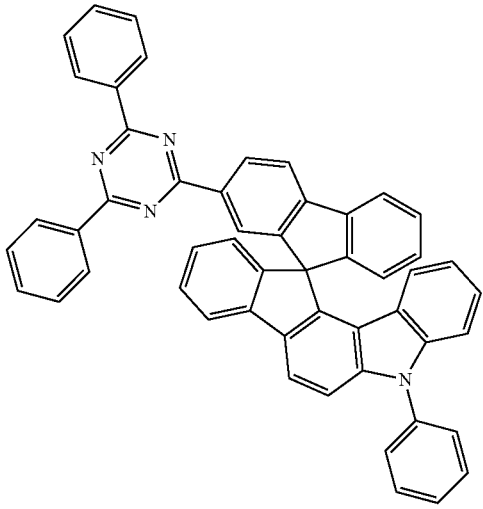 [SMILES: c1ccc(-c2nc(-c3ccccc3)nc(-c3ccc4c(c3)C3(c5ccccc5-4)c4ccccc4-c4ccc5c(c43)c3ccccc3n5-c3ccccc3)n2)cc1]
33
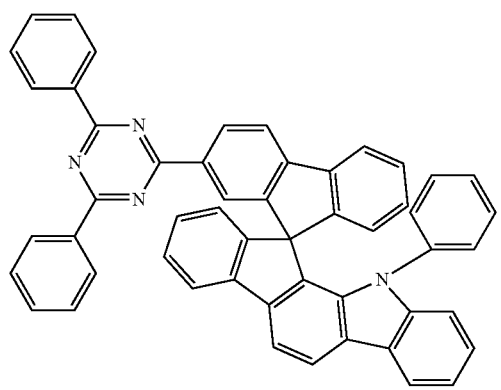 [SMILES: c1ccc(-c2nc(-c3ccccc3)nc(-c3ccc4c(c3)C3(c5ccccc5-4)c4ccccc4-c4ccc5c6ccccc6n(-c6ccccc6)c5c43)n2)cc1]
34
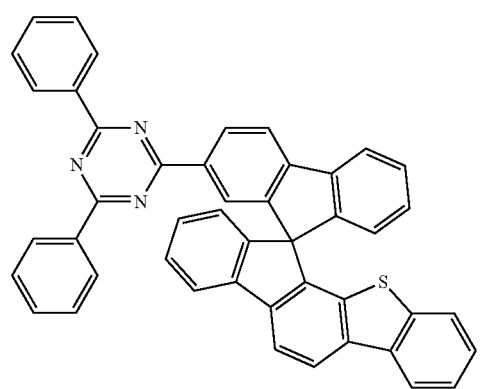 [SMILES: c1ccc(-c2nc(-c3ccccc3)nc(-c3ccc4c(c3)C3(c5ccccc5-4)c4ccccc4-c4ccc5c(sc6ccccc65)c43)n2)cc1]
35

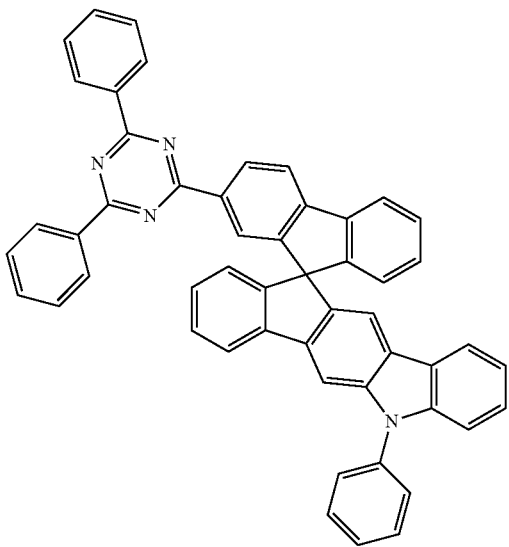 [SMILES: c1ccc(-c2nc(-c3ccccc3)nc(-c3ccc4c(c3)C3(c5ccccc5-4)c4ccccc4-c4cc5c(cc43)c3ccccc3n5-c3ccccc3)n2)cc1]
36
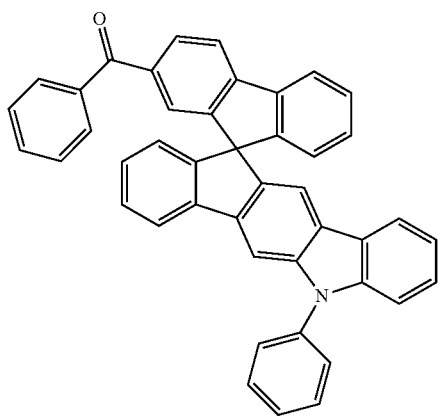 [SMILES: O=C(c1ccccc1)c1ccc2c(c1)C1(c3ccccc3-2)c2ccccc2-c2cc3c(cc21)c1ccccc1n3-c1ccccc1]
37
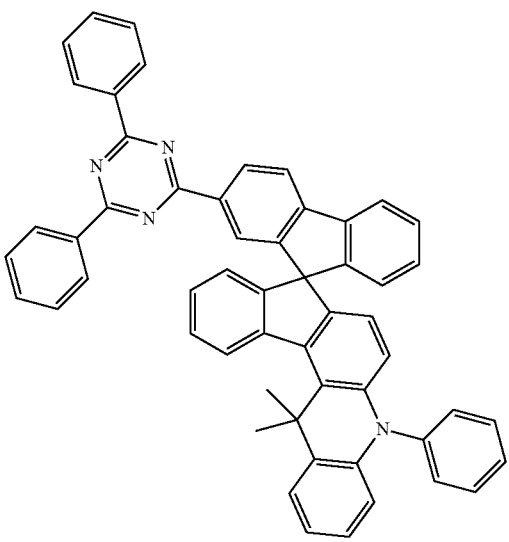 [SMILES: CC1(C)c2ccccc2N(c2ccccc2)c2ccc3c(c21)-c1ccccc1C31c2ccccc2-c2ccc(-c3nc(-c4ccccc4)nc(-c4ccccc4)n3)cc21]
38

39
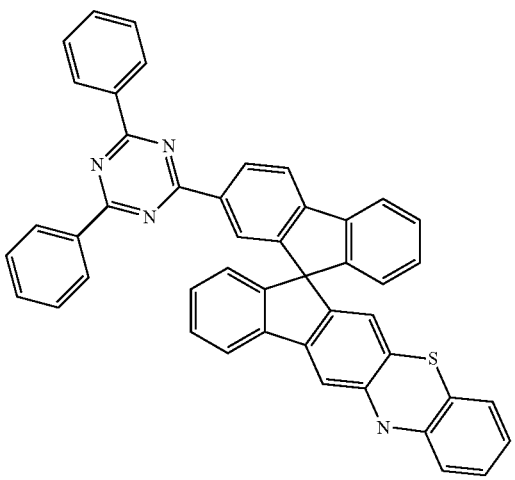 [SMILES: c1ccc(-c2nc(-c3ccccc3)nc(-c3ccc4c(c3)C3(c5ccccc5-4)c4ccccc4-c4cc5c(cc43)Sc3ccccc3N5)n2)cc1]
40
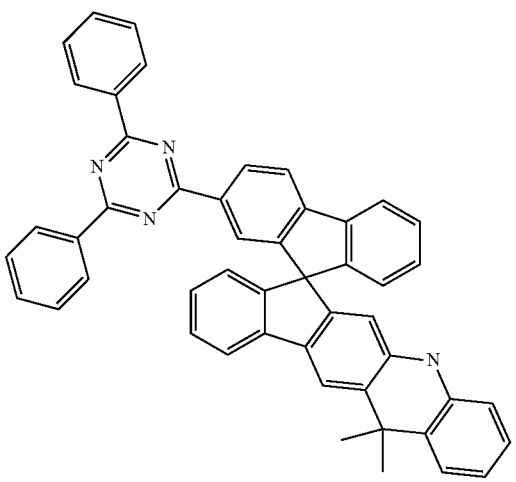 [SMILES: CC1(C)c2ccccc2Nc2cc3c(cc21)-c1ccccc1C31c2ccccc2-c2ccc(-c3nc(-c4ccccc4)nc(-c4ccccc4)n3)cc21]
41
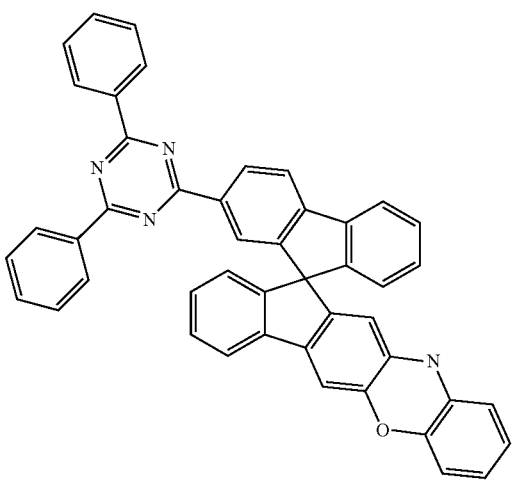 [SMILES: c1ccc(-c2nc(-c3ccccc3)nc(-c3ccc4c(c3)C3(c5ccccc5-4)c4ccccc4-c4cc5c(cc43)Nc3ccccc3O5)n2)cc1]

-continued
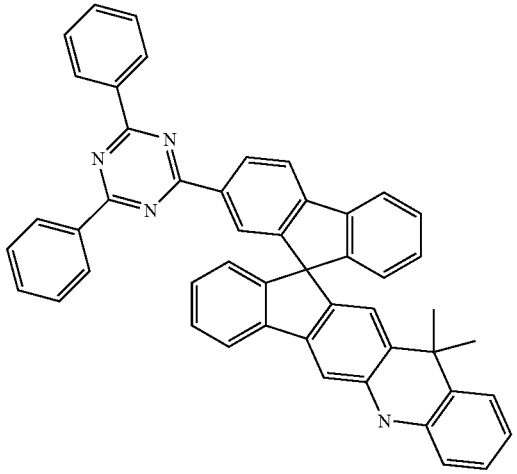 [SMILES: CC1(C)c2ccccc2Nc2cc3c(cc21)C1(c2ccccc2-c2ccc(-c4nc(-c5ccccc5)nc(-c5ccccc5)n4)cc21)c1ccccc1-3]
42
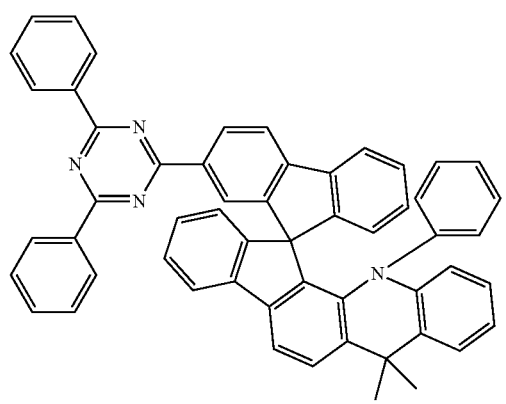 [SMILES: CC1(C)c2ccccc2N(c2ccccc2)c2c1ccc1c2C2(c3ccccc3-c3ccc(-c4nc(-c5ccccc5)nc(-c5ccccc5)n4)cc32)c2ccccc2-1]
43
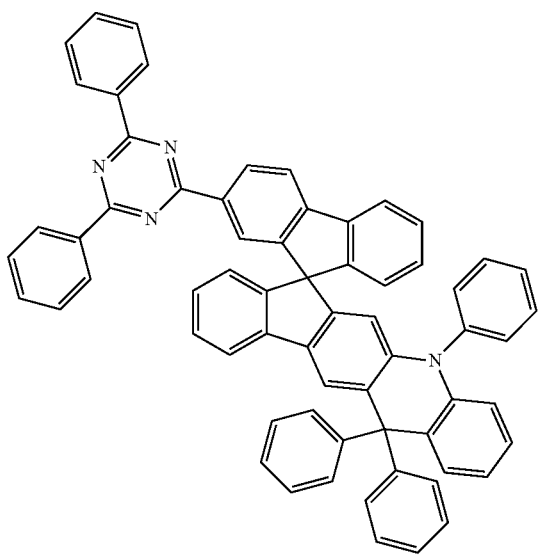 [SMILES: c1ccc(-c2nc(-c3ccccc3)nc(-c3ccc4c(c3)C3(c5ccccc5-4)c4ccccc4-c4cc5c(cc43)N(c3ccccc3)c3ccccc3C5(c3ccccc3)c3ccccc3)n2)cc1]
44

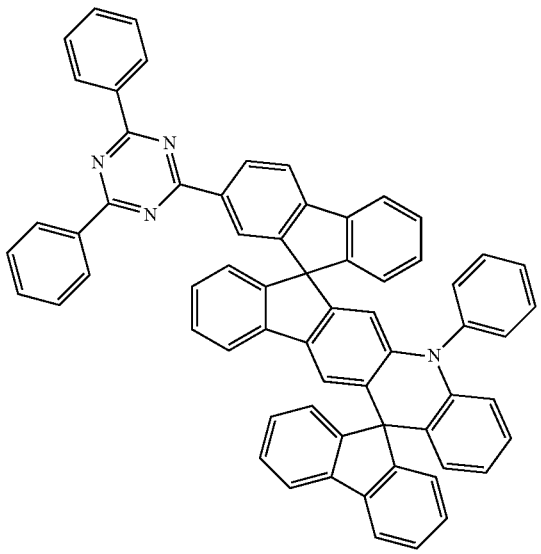 [SMILES: c1ccc(-c2nc(-c3ccccc3)nc(-c3ccc4c(c3)C3(c5ccccc5-4)c4ccccc4-c4cc5c(cc43)N(c3ccccc3)c3ccccc3C53c4ccccc4-c4ccccc43)n2)cc1]
45
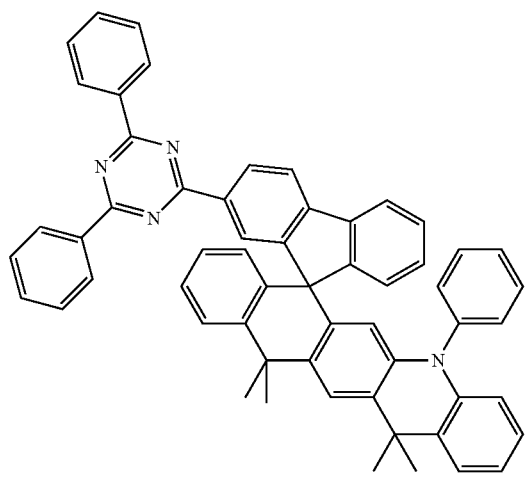 [SMILES: CC1(C)c2ccccc2N(c2ccccc2)c2cc3c(cc21)C(C)(C)c1ccccc1C31c2ccccc2-c2ccc(-c3nc(-c4ccccc4)nc(-c4ccccc4)n3)cc21]
46
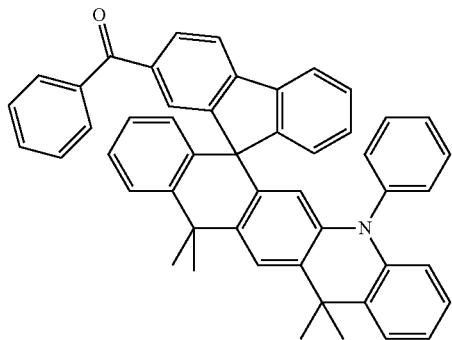 [SMILES: CC1(C)c2ccccc2N(c2ccccc2)c2cc3c(cc21)C(C)(C)c1ccccc1C31c2ccccc2-c2ccc(C(=O)c3ccccc3)cc21]
47

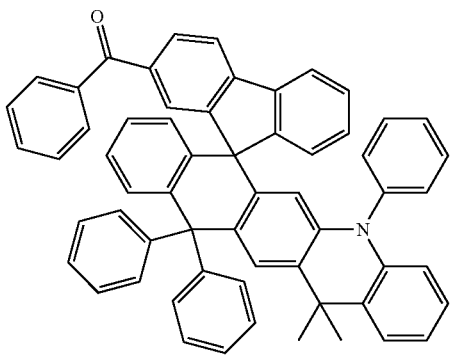 [SMILES: CC1(C)c2ccccc2N(c2ccccc2)c2cc3c(cc21)C(c1ccccc1)(c1ccccc1)c1ccccc1C31c2ccccc2-c2ccc(C(=O)c3ccccc3)cc21]
48
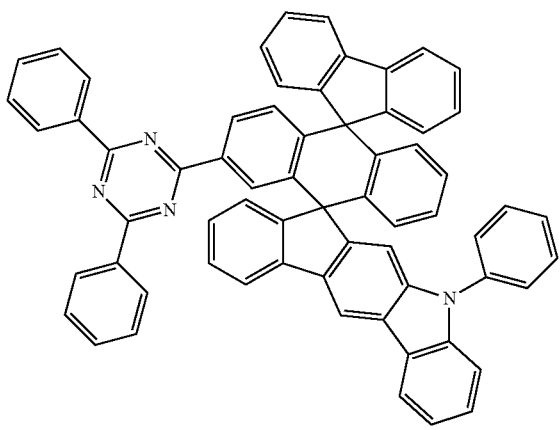 [SMILES: c1ccc(-c2nc(-c3ccccc3)nc(-c3ccc4c(c3)C3(c5ccccc5-c5cc6c7ccccc7n(-c7ccccc7)c6cc53)c3ccccc3C43c4ccccc4-c4ccccc43)n2)cc1]
49
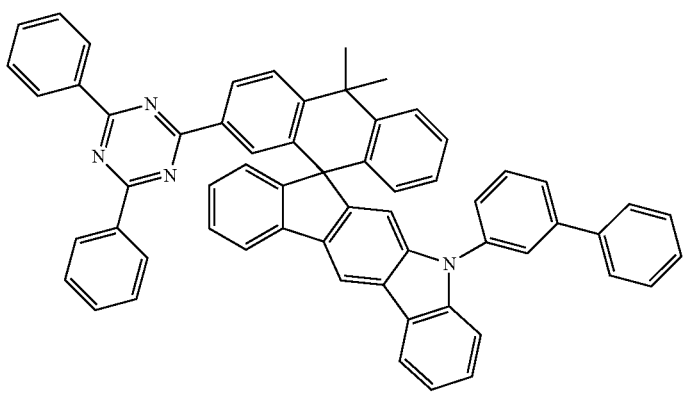 [SMILES: CC1(C)c2ccccc2C2(c3ccccc3-c3cc4c5ccccc5n(-c5cccc(-c6ccccc6)c5)c4cc32)c2cc(-c3nc(-c4ccccc4)nc(-c4ccccc4)n3)ccc21]
50
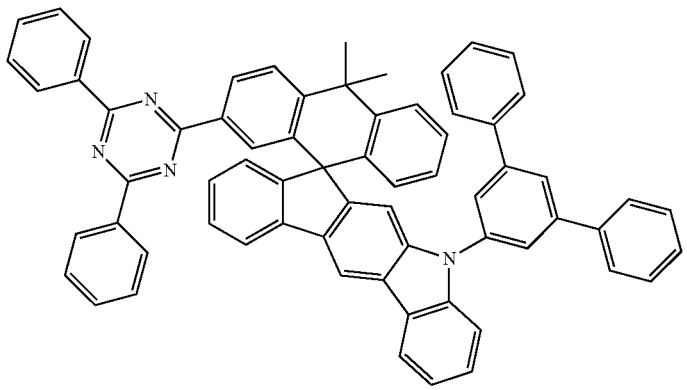 [SMILES: CC1(C)c2ccccc2C2(c3ccccc3-c3cc4c5ccccc5n(-c5cc(-c6ccccc6)cc(-c6ccccc6)c5)c4cc32)c2cc(-c3nc(-c4ccccc4)nc(-c4ccccc4)n3)ccc21]
51

-continued
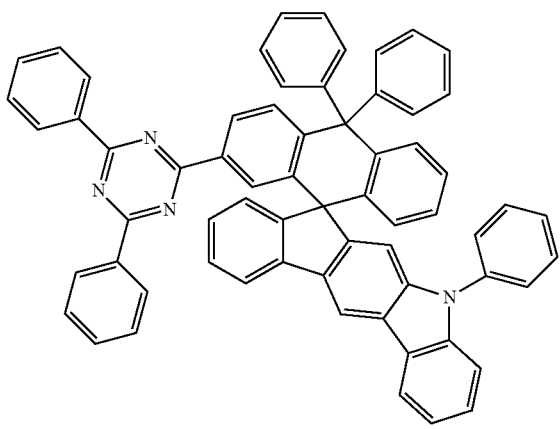 [SMILES: c1ccc(-c2nc(-c3ccccc3)nc(-c3ccc4c(c3)C3(c5ccccc5-c5cc6c7ccccc7n(-c7ccccc7)c6cc53)c3ccccc3C4(c3ccccc3)c3ccccc3)n2)cc1]
52
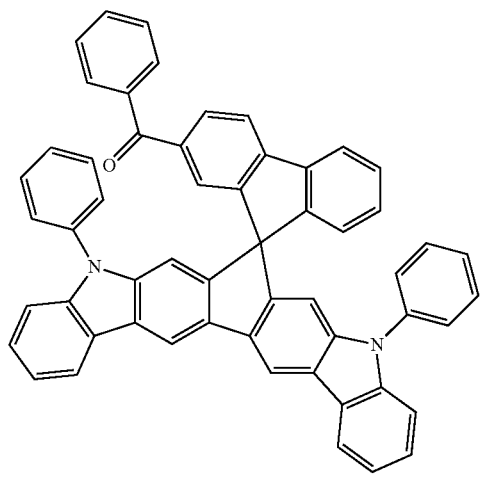 [SMILES: O=C(c1ccccc1)c1ccc2c(c1)C1(c3ccccc3-2)c2cc3c(cc2-c2cc4c5ccccc5n(-c5ccccc5)c4cc21)c1ccccc1n3-c1ccccc1]
53
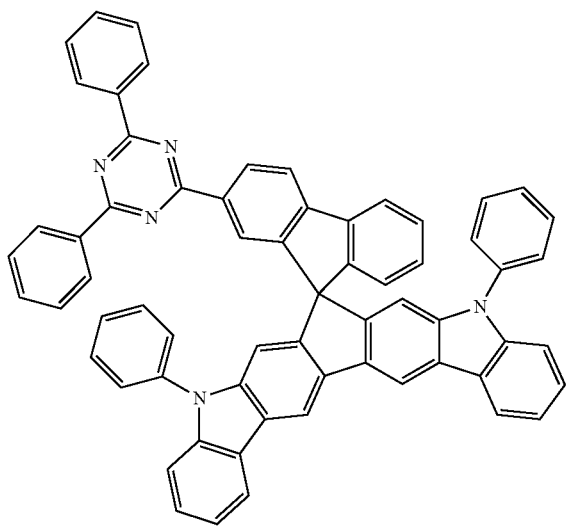 [SMILES: c1ccc(-c2nc(-c3ccccc3)nc(-c3ccc4c(c3)C3(c5ccccc5-4)c4cc5c(cc4-c4cc6c7ccccc7n(-c7ccccc7)c6cc43)c3ccccc3n5-c3ccccc3)n2)cc1]
54

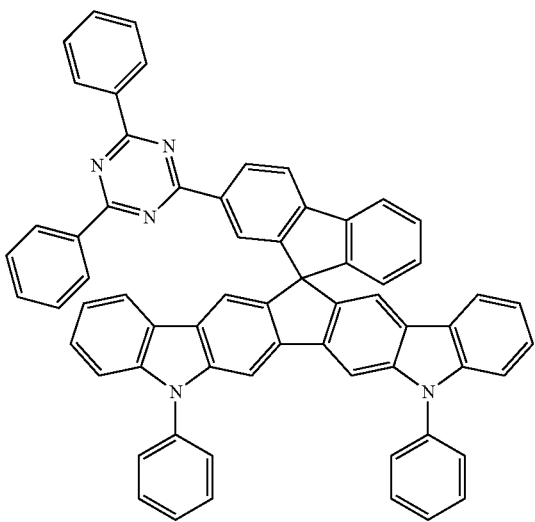 [SMILES: c1ccc(-c2nc(-c3ccccc3)nc(-c3ccc4c(c3)C3(c5ccccc5-4)c4cc5c6ccccc6n(-c6ccccc6)c5cc4-c4cc5c(cc43)c3ccccc3n5-c3ccccc3)n2)cc1]
55
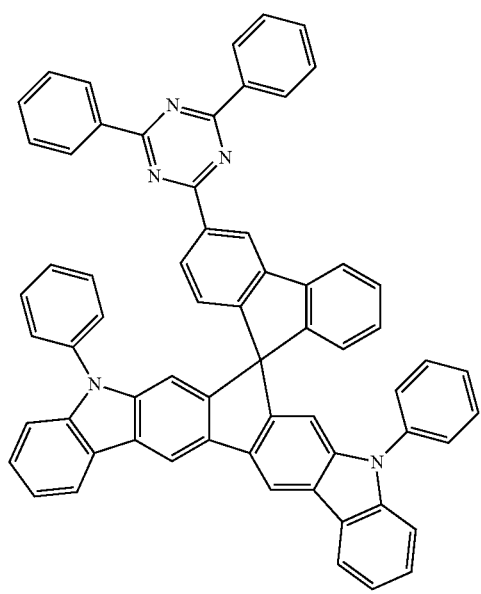 [SMILES: c1ccc(-c2nc(-c3ccccc3)nc(-c3ccc4c(c3)-c3ccccc3C43c4cc5c(cc4-c4cc6c7ccccc7n(-c7ccccc7)c6cc43)c3ccccc3n5-c3ccccc3)n2)cc1]
56

-continued
57
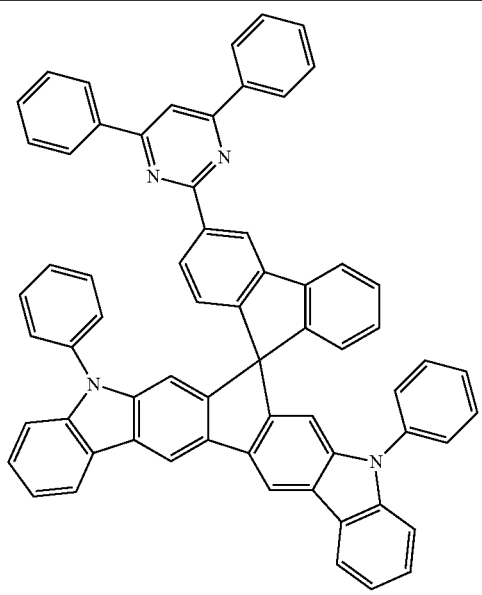
58
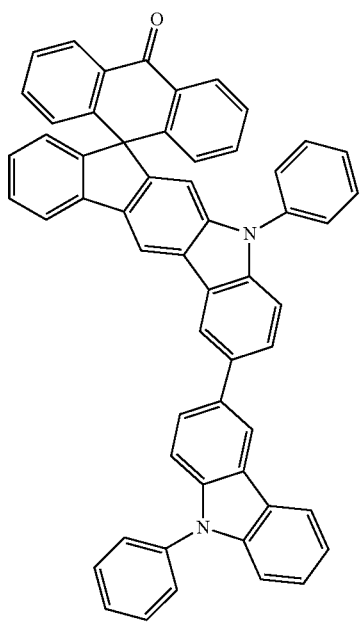 [SMILES: O=C1c2ccccc2C2(c3ccccc31)c1ccccc1-c1cc3c4cc(-c5ccc6c(c5)c5ccccc5n6-c5ccccc5)ccc4n(-c4ccccc4)c3cc12]
59
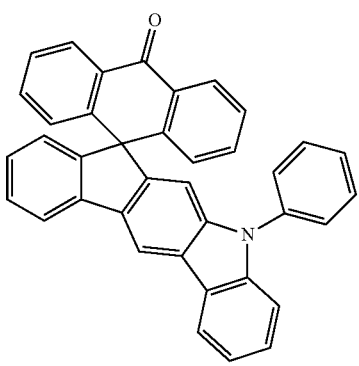 [SMILES: O=C1c2ccccc2C2(c3ccccc31)c1ccccc1-c1cc3c4ccccc4n(-c4ccccc4)c3cc12]

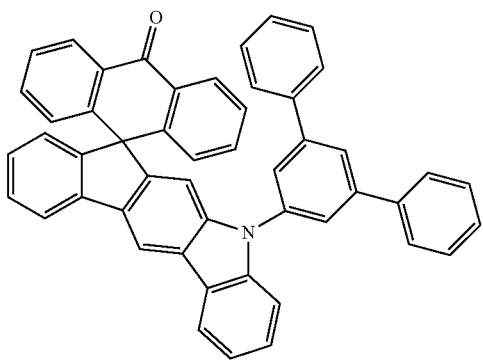 [SMILES: O=C1c2ccccc2C2(c3ccccc31)c1ccccc1-c1cc3c4ccccc4n(-c4cc(-c5ccccc5)cc(-c5ccccc5)c4)c3cc12]
60
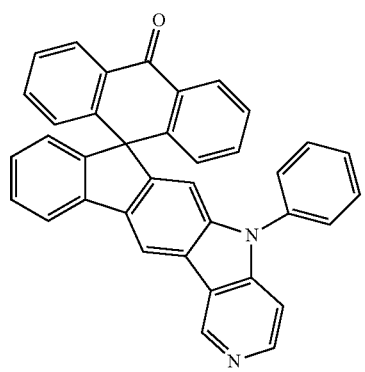 [SMILES: O=C1c2ccccc2C2(c3ccccc31)c1ccccc1-c1cc3c4cnccc4n(-c4ccccc4)c3cc12]
61
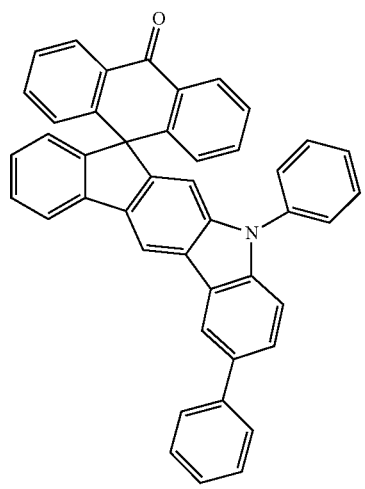 [SMILES: O=C1c2ccccc2C2(c3ccccc31)c1ccccc1-c1cc3c4cc(-c5ccccc5)ccc4n(-c4ccccc4)c3cc12]
62
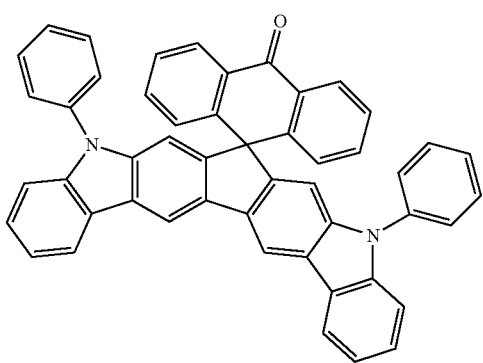 [SMILES: O=C1c2ccccc2C2(c3ccccc31)c1cc3c(cc1-c1cc4c5ccccc5n(-c5ccccc5)c4cc12)c1ccccc1n3-c1ccccc1]
63

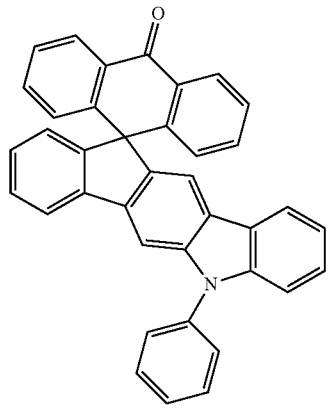 [SMILES: O=C1c2ccccc2C2(c3ccccc31)c1ccccc1-c1cc3c(cc12)c1ccccc1n3-c1ccccc1]
64
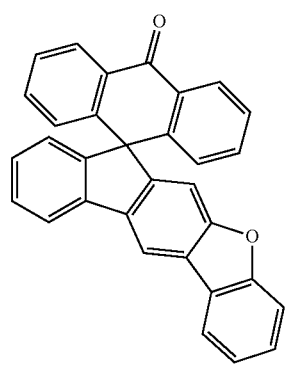 [SMILES: O=C1c2ccccc2C2(c3ccccc31)c1ccccc1-c1cc3c(cc12)oc1ccccc13]
65
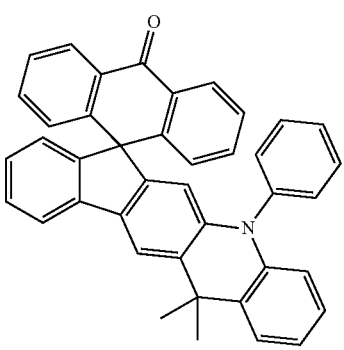 [SMILES: CC1(C)c2ccccc2N(c2ccccc2)c2cc3c(cc21)-c1ccccc1C31c2ccccc2C(=O)c2ccccc21]
66
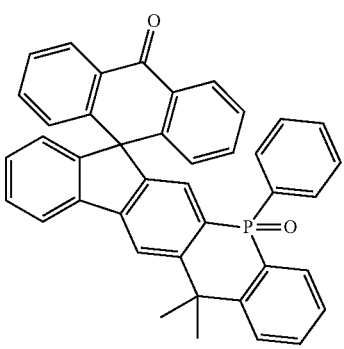 [SMILES: CC1(C)c2ccccc2P(=O)(c2ccccc2)c2cc3c(cc21)-c1ccccc1C31c2ccccc2C(=O)c2ccccc21]
67

68 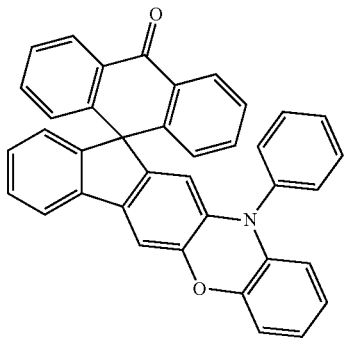 [SMILES: O=C1c2ccccc2C2(c3ccccc31)c1ccccc1-c1cc3c(cc12)N(c1ccccc1)c1ccccc1O3]
69 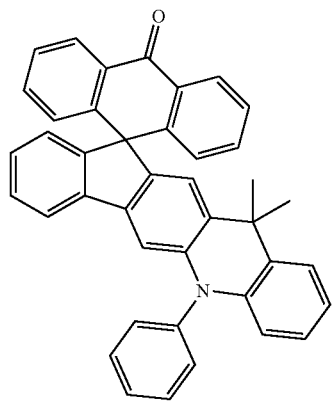 [SMILES: CC1(C)c2ccccc2N(c2ccccc2)c2cc3c(cc21)C1(c2ccccc2C(=O)c2ccccc21)c1ccccc1-3]
70 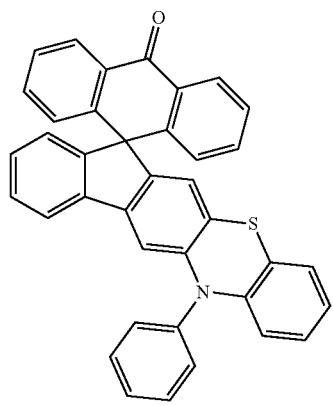 [SMILES: O=C1c2ccccc2C2(c3ccccc31)c1ccccc1-c1cc3c(cc12)Sc1ccccc1N3c1ccccc1]
71 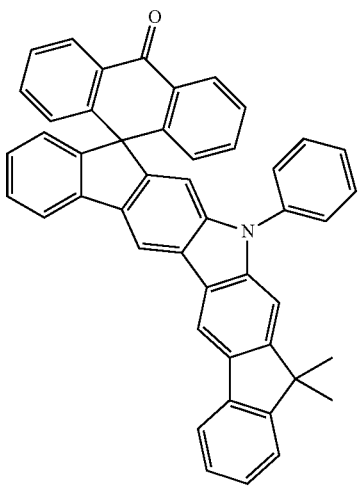 [SMILES: CC1(C)c2ccccc2-c2cc3c4cc5c(cc4n(-c4ccccc4)c3cc21)C1(c2ccccc2C(=O)c2ccccc21)c1ccccc1-5]

-continued
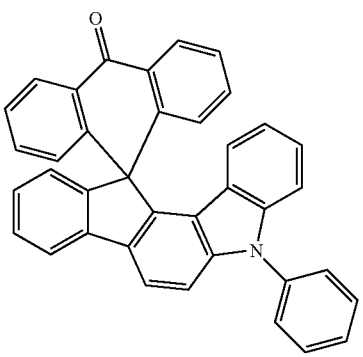 [SMILES: O=C1c2ccccc2C2(c3ccccc31)c1ccccc1-c1ccc3c(c12)c1ccccc1n3-c1ccccc1]
72
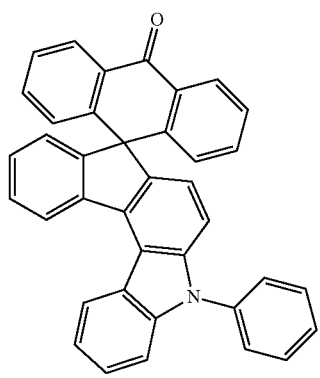 [SMILES: O=C1c2ccccc2C2(c3ccccc31)c1ccccc1-c1c2ccc2c1c1ccccc1n2-c1ccccc1]
73
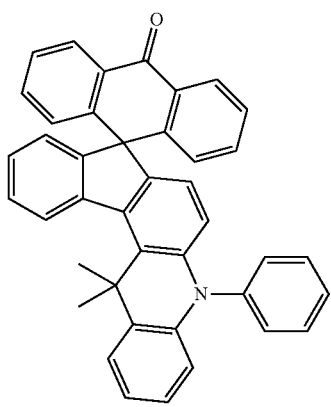 [SMILES: CC1(C)c2ccccc2N(c2ccccc2)c2ccc3c(c21)-c1ccccc1C31c2ccccc2C(=O)c2ccccc21]
74
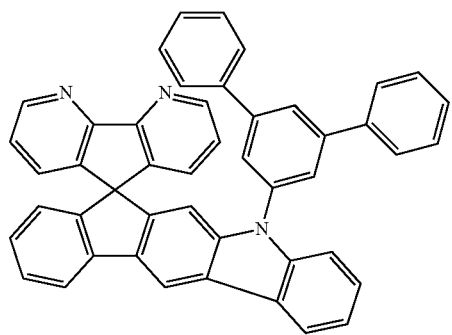 [SMILES: c1ccc(-c2cc(-c3ccccc3)cc(-n3c4ccccc4c4cc5c(cc43)C3(c4ccccc4-5)c4cccnc4-c4ncccc43)c2)cc1]
75

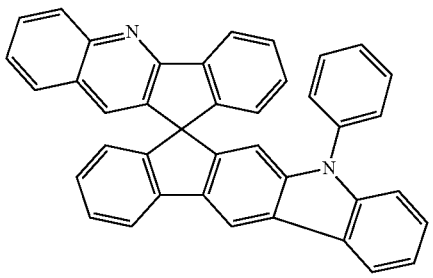 [SMILES: c1ccc(-n2c3ccccc3c3cc4c(cc32)C2(c3ccccc3-4)c3ccccc3-c3nc4ccccc4cc32)cc1]

76

The synthesis of the compounds according to the invention can be carried out by processes and reaction types known from the prior art, for example halogenation, Buchwald coupling and Suzuki coupling.

Two preferred synthetic processes for the preparation of the compounds according to the invention will be presented below.

The person skilled in the art does not have to rely on the processes disclosed here for the synthesis of the compounds according to the invention, but instead will be able to develop and apply alternative synthetic routes within his expert knowledge in the area of organic synthesis.

The starting material used in the synthetic route shown in Scheme 1 is a spirobifluorene compound which carries a reactive group, for example a halogen group, and a radical R*. The radical R* represents an electron-deficient group, for example a triazine group, a ketone or a phosphine oxide. Starting compounds of this type can in many cases be prepared in one or few steps from commercially available compounds. Explicit synthetic routes for such compounds are shown in the working examples.

In the two subsequent steps, the condensed-on indole group is introduced via a Buchwald coupling and subsequent palladium-catalysed cyclisation. Instead of this reaction sequence, other heteroaryl groups, for example the structures reproduced in the tabular examples, can also be condensed on via different reactions. In a third step, the free NH function is arylated via a Buchwald coupling.

Scheme 1

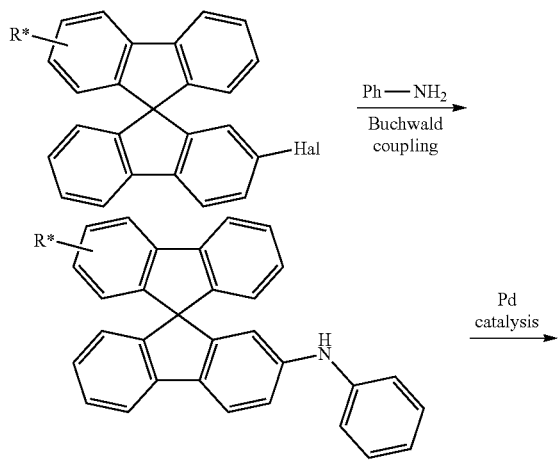

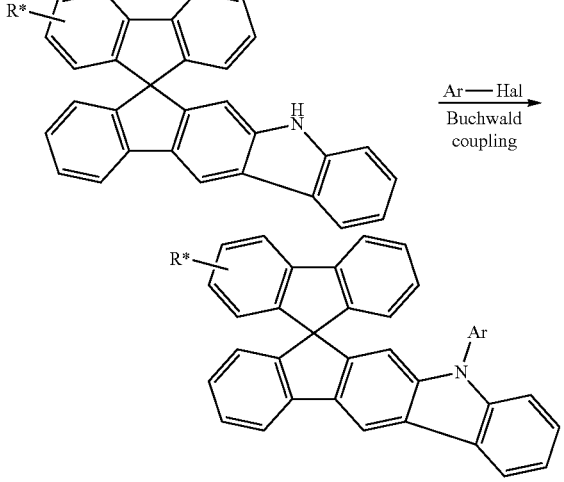

R* = electron-defficient group, for example triazine, pyrimidine, benzimidazole, ketone, phosphine oxide
Hal = halide or other suitable reactive group
Ar = aryl or heteroaryl group The synthetic route shown in Scheme 2 enables the preparation of compounds according to the invention which carry a modified spirobifluorene group, for example a spirobifluorene group which has been modified by a keto bridge. To this end, the starting material used is a fluorene derivative which carries a reactive group. An indole group can be condensed on again via the above-described sequence of Buchwald coupling and cyclisation. This indole group is, as likewise already described above, arylated by means of a Buchwald coupling. In a final step, the modified spirobifluorene group is prepared via a cyclisation reaction from the fluorenone group.

It is alternatively possible to employ a starting compound other than that described in Scheme 2 in the cyclisation reaction. Some starting compounds of this type are commercially available. In this respect, corresponding synthesis examples of compounds according to the invention are described in the working examples.

Scheme 2

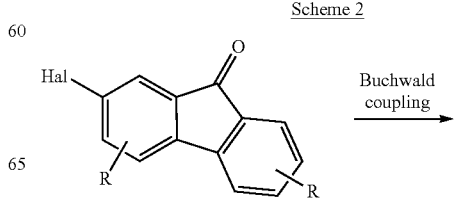

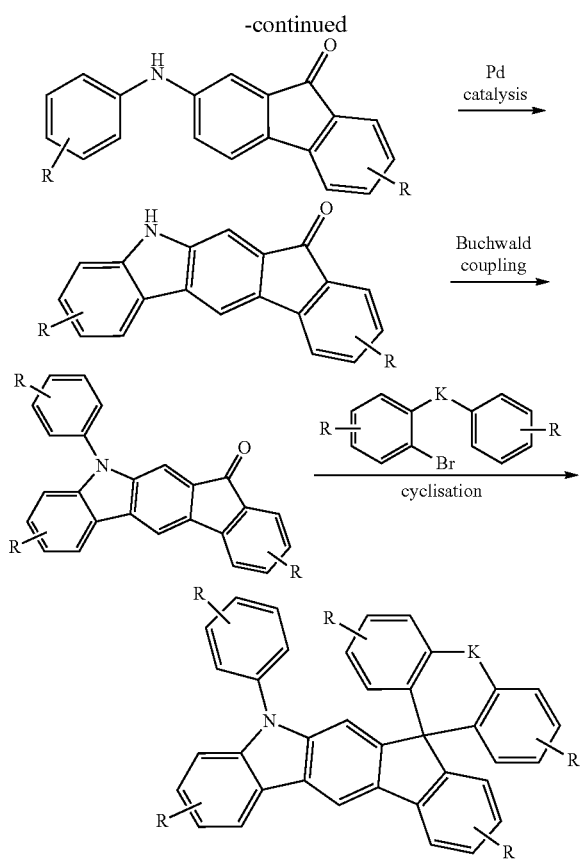

Hal = halide or another suitable reactive group
R = organic radical
K = C═O, P═OR, SO, SO$_2$, single bond The invention thus relates to a process for the preparation of compounds according to the invention, characterised in that
a heteroaryl group is condensed onto a spirobifluorene group which is substituted by an electron-deficient group, or in that
a cyclisation reaction is carried out via which a modified spirobifluorene group is obtained.

The above-mentioned electron-deficient group is preferably a triazine group, a pyrimidine group, a benzimidazole group, a ketone group or a phosphine oxide group.

The modified spirobifluorene group furthermore preferably contains a keto group, a phosphine oxide group, a sulfoxide group or a sulfone group.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I) or (II), where the bond(s) to the polymer, oligomer or dendrimer can be localised at any desired positions that are substituted by R$^1$ or R$^2$. Depending on the linking of the compound of the formula (I), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) or (II) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) or (II) may be linked via a trivalent or polyvalent group, for example via a trivalent or polyvalent aromatic or heteroaromatic group, to form a branched or dendritic oligomer or polymer.

The same preferences as described above for compounds of the formula (I) or (II) apply to the recurring units of the formula (I) or (II) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, of which at least one monomer results in recurring units of the formula (I) or (II) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds of the formula (I) or (II) from liquid phase, for example by spin coating or by printing processes, formulations of the compounds are necessary. These formulations can be, for example, solutions, dispersions or mini-emulsions.

The invention therefore furthermore relates to a formulation, in particular a solution, dispersion or mini-emulsion, comprising at least one compound of the formula (I) or (II) or at least one polymer, oligomer or dendrimer containing at least one unit of the formula (I) or (II) and at least one solvent, preferably an organic solvent. The way in which solutions of this type can be prepared is known to the person skilled in the art and is described, for example, in the applications WO 2002/072714 and WO 2003/019694 and the literature cited therein.

The compounds of the formula (I) or (II) are suitable for use in electronic devices, in particular in organic electroluminescent devices (OLEDs). The compounds can be employed in different functions and/or layers, inter alia depending on the substitution. The compounds are preferably employed as host materials for phosphorescent emitters and/or as electron-transport materials in an electron-transport layer and/or as hole-blocking materials in a hole-blocking layer.

The invention furthermore relates to the use of the compounds of the formula (I) or (II) in electronic devices. The electronic devices here are preferably selected from the group consisting of organic integrated circuits (O—ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention furthermore relates to an electronic device comprising anode, cathode and at least one organic layer, where the organic layer comprises at least one compound of the formula (I) or (II). The electronic device here is preferably selected from the above-mentioned devices and is particularly preferably an organic electroluminescent device (OLED).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent. The compounds preferably employed in the respective layers and functions are explicitly disclosed in later sections.

It is preferred in accordance with the invention for the compound of the formula (I) or (II) to be employed in an electronic device comprising one or more phosphorescent dopants. The compound can be used in various layers here, preferably in an electron-transport layer, a hole-transport layer, a hole-injection layer or in the emitting layer. However, the compound of the formula (I) or (II) can also be employed in accordance with the invention in an electronic device comprising one or more fluorescent dopants and no phosphorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs. Further examples of suitable phosphorescent dopants are revealed by the table following in a later section.

In a preferred embodiment of the present invention, the compounds of the formula (I) or (II) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (I) or (II) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or entirely in a single mixed-matrix component, where the further mixed-matrix components fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More detailed information of mixed-matrix systems is given, inter alia, in the application WO 2010/108579.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Particularly suitable matrix materials, which can be employed in combination with the compounds according to the invention as matrix components of a mixed-matrix system, are generally the preferred matrix materials indicated in following sections. Depending on whether a fluorescent or phosphorescent dopant is present in the emitting layer, the preferred matrix materials indicated below for fluorescent dopants or the preferred matrix materials indicated below for phosphorescent dopants are preferred.

Preferred phosphorescent dopants for use in mixed-matrix systems comprising the compounds according to the invention are the phosphorescent dopants shown in a following table.

In a further preferred embodiment of the invention, the compound of the formula (I) or (II) is employed as electron-transport material in an electron-transport or electron-injection layer. The emitting layer here may comprise fluorescent and/or phosphorescent emitters. If the compound is employed as electron-transport material, it may be preferred for it to be doped, for example with alkali-metal complexes, such as, for example, Liq (lithium hydroxyquinolinate). Also suitable is the combination of the compound according to the invention in an electron-transport layer with an electron-injection layer. Suitable materials for the electron-injection layer are, for example, alkali or alkaline-earth metal fluorides, such as, for example, LiF.

In still a further preferred embodiment of the invention, the compound of the formula (I) or (II) is employed as hole-blocking material in a hole-blocking layer. A hole-blocking layer is taken to mean a layer which is directly adjacent to an emitting layer on the cathode side.

The organic electroluminescent device according to the invention may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers, where the various colours in this embodiment of the invention together give white light. Particular preference is given to three-layer systems, i.e. systems having three emitting layers, where one pr more of these layers comprises a compound of the formula (I) or (II) and where the three layers exhibit blue, green and orange or red emission (for the basic structure see, for example, WO 2005/011013). Likewise, emitters which have broad-band emission bands and thus exhibit white emission are suitable for white emission in such systems. Alternatively and/or additionally, the compounds according to the invention may also be present in a hole-transport layer or electron-transport layer or in another layer in such systems.

The further functional materials preferably employed in the electronic devices according to the invention are shown below.

The compounds shown in the following table are particularly suitable phosphorescent dopants.

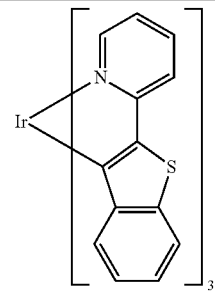

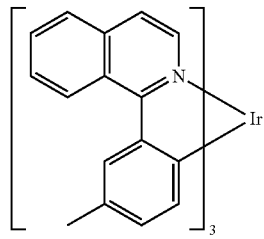

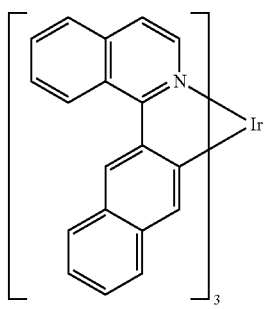
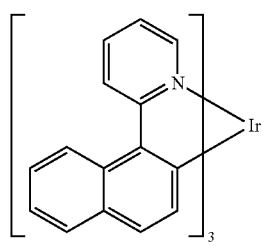
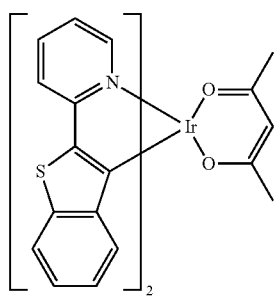
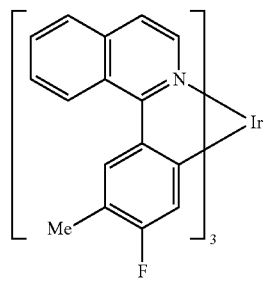
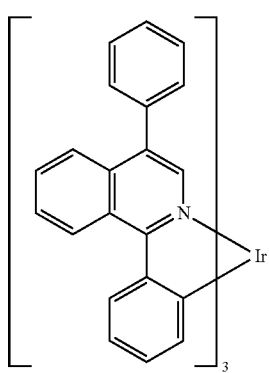
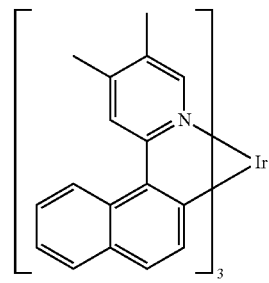
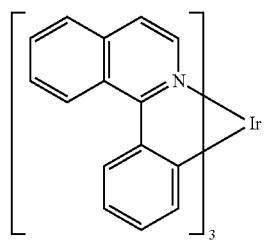
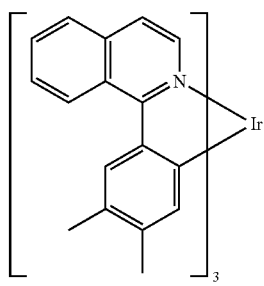
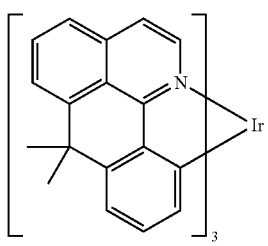
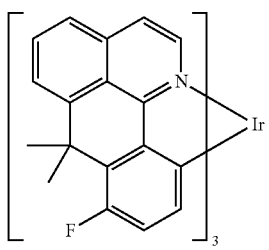

91
-continued
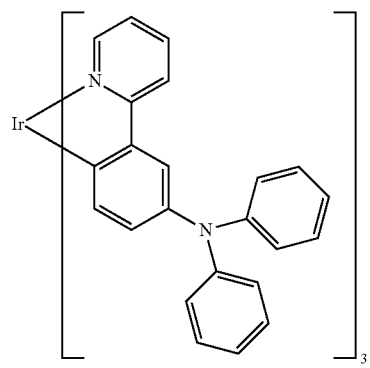
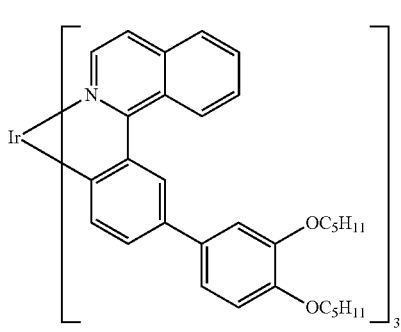
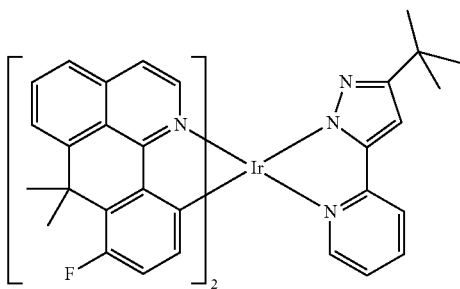
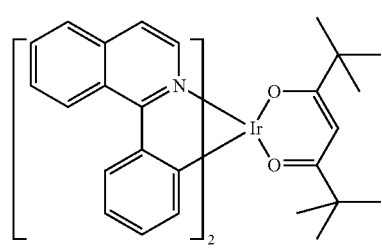
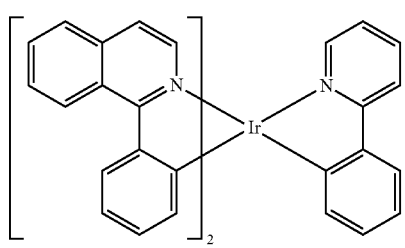
92
-continued
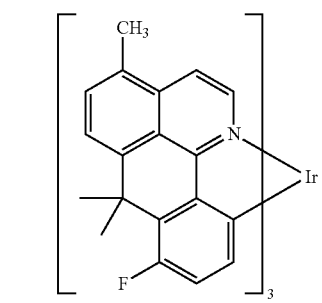
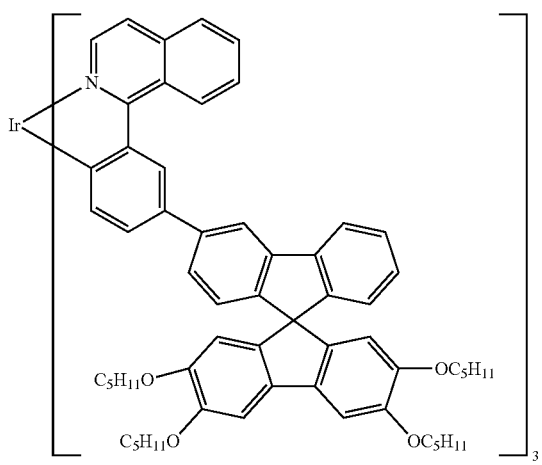
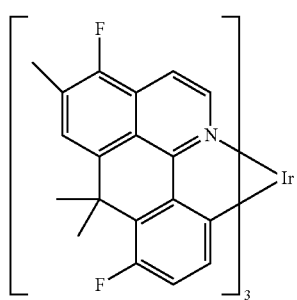

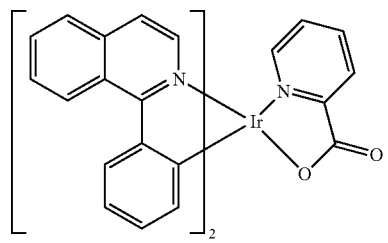
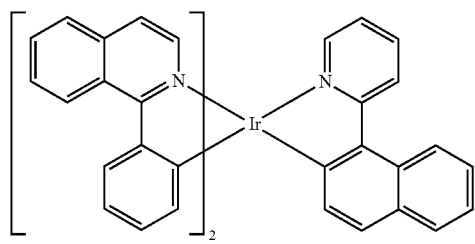
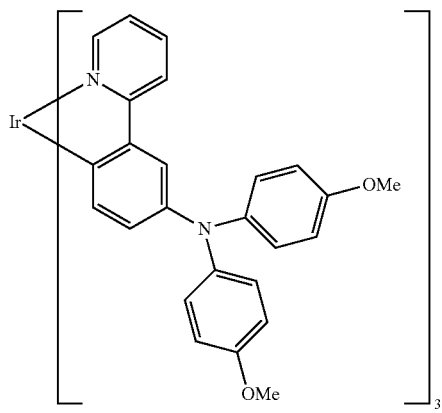
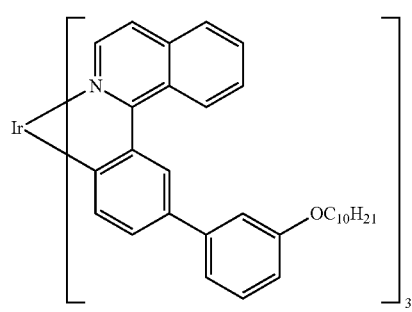
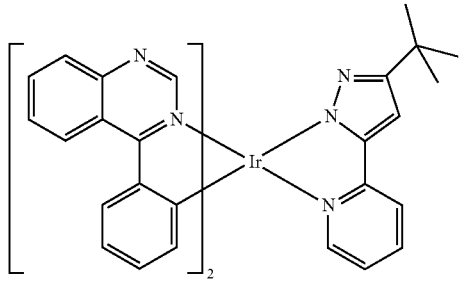
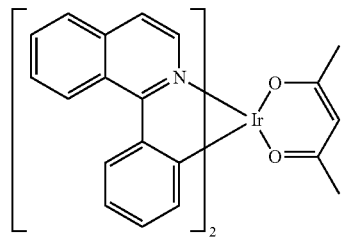
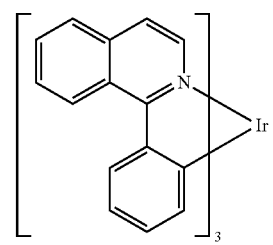
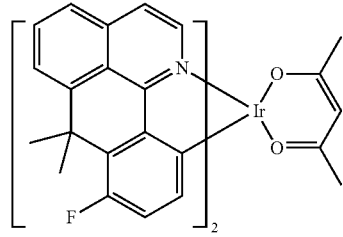
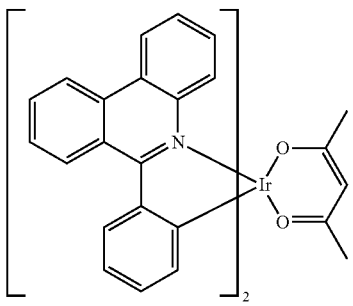
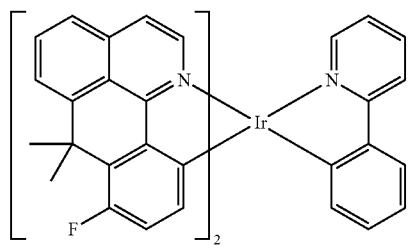
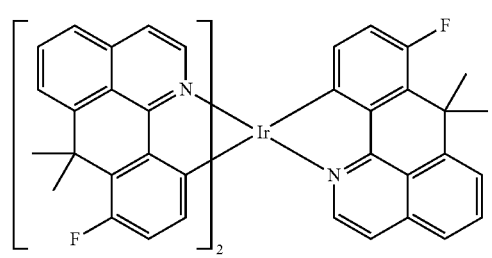

95
-continued
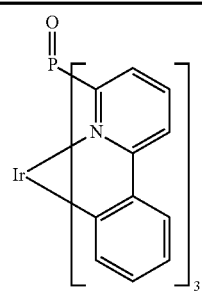
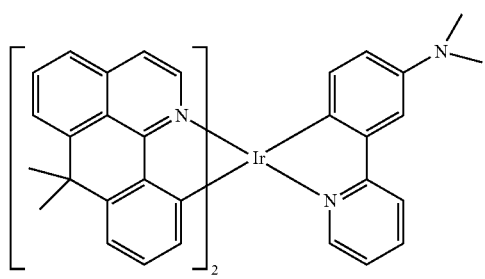
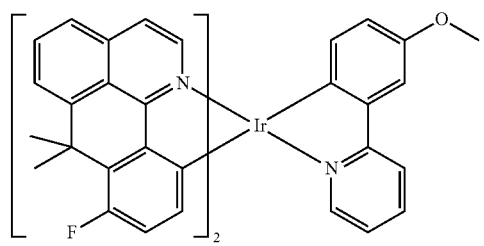
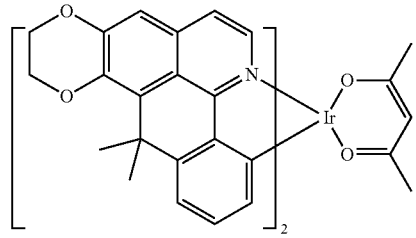
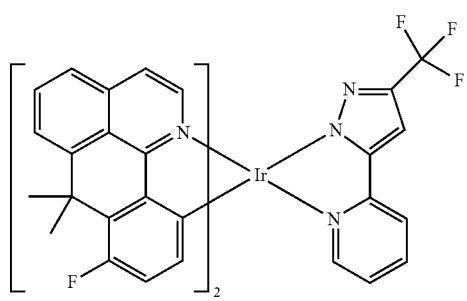
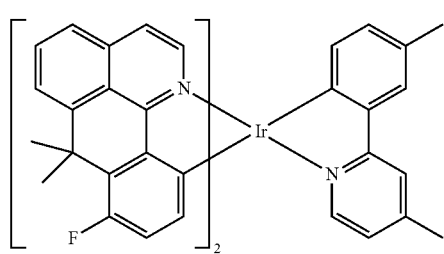
96
-continued
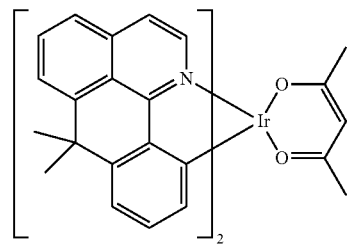
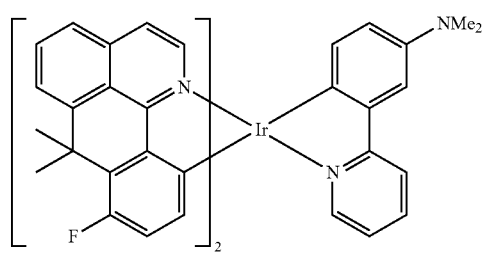
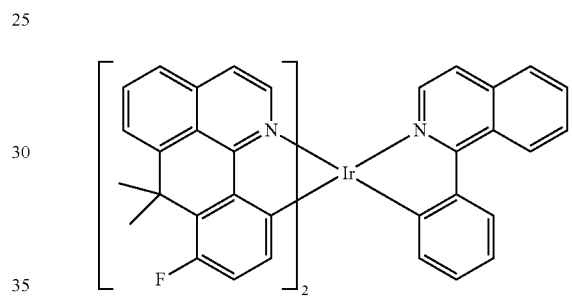
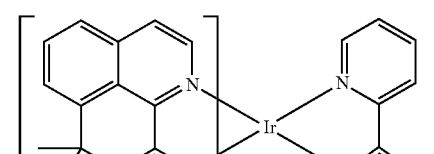
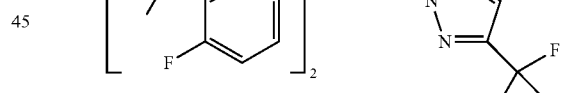
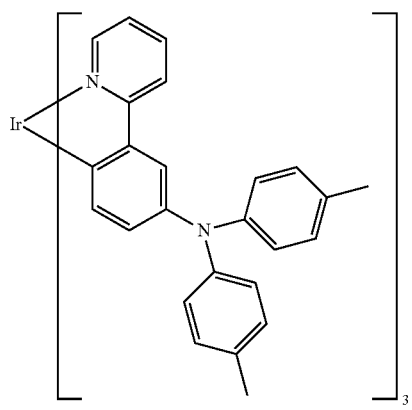

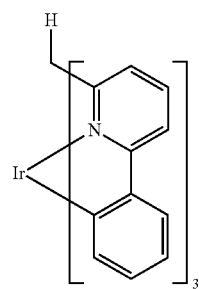
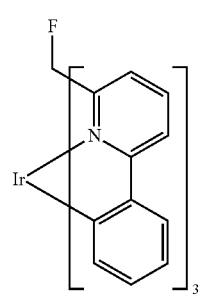
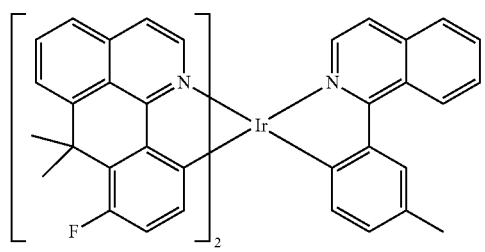
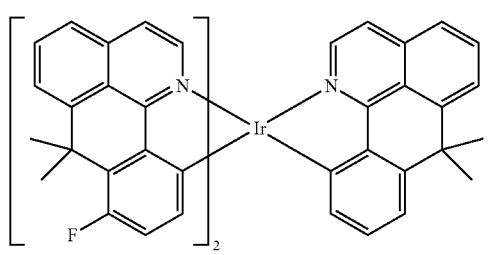
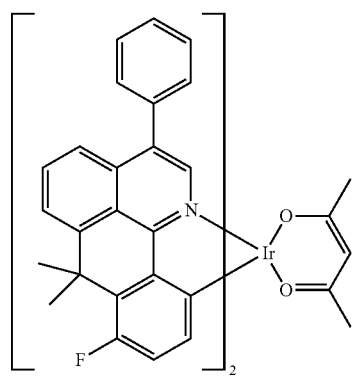
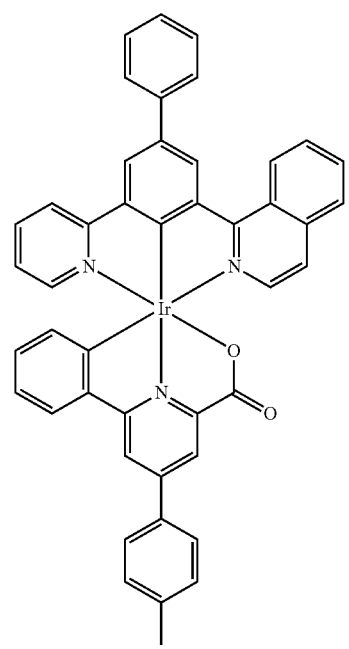
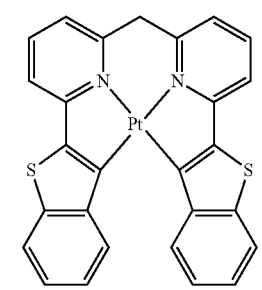
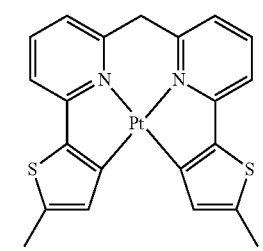
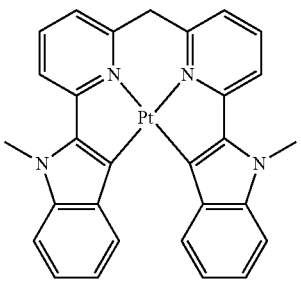

99
-continued
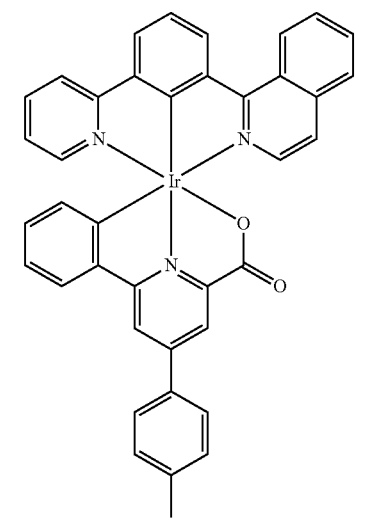
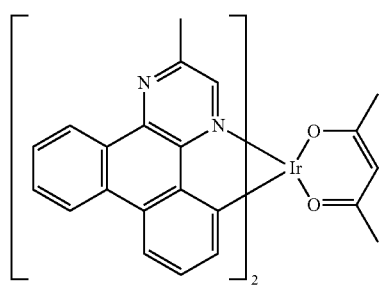
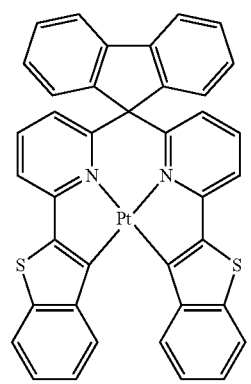
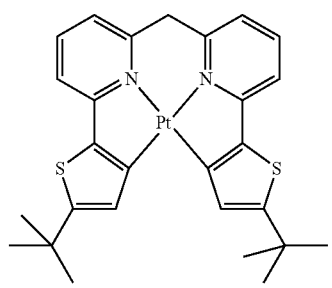
100
-continued
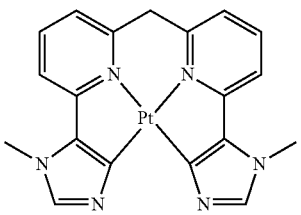
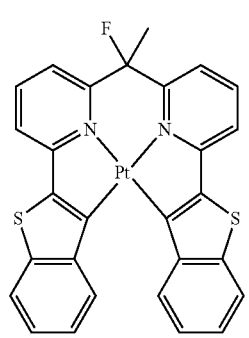
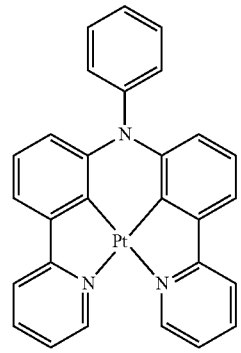
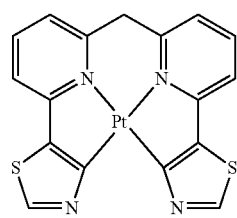
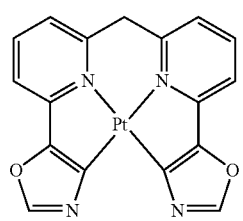

| 101 -continued | 102 -continued |
|---|---|
| 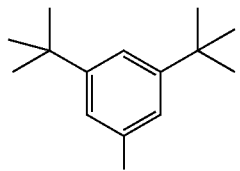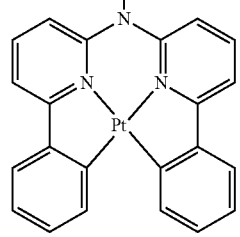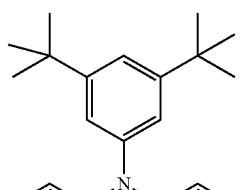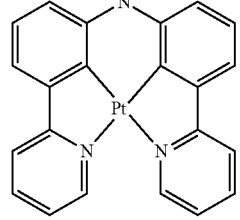 | 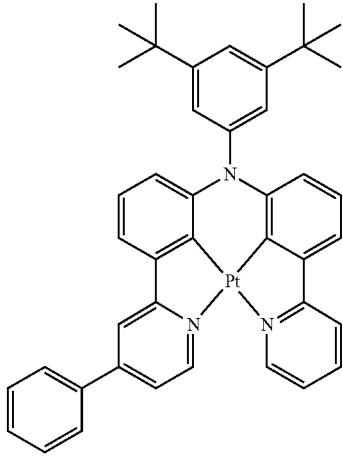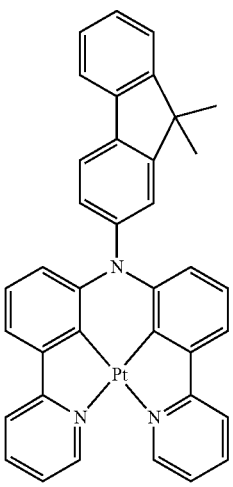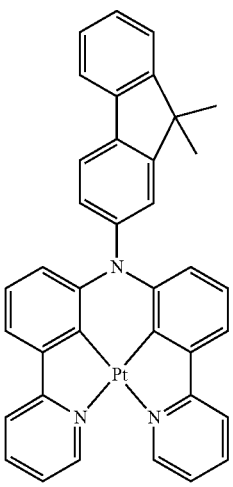 |

| 103 -continued | 104 -continued |
|---|---|
| 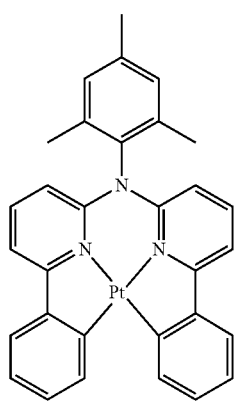 | 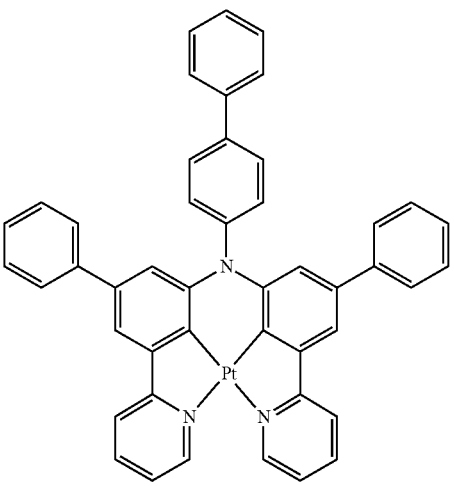 |
| 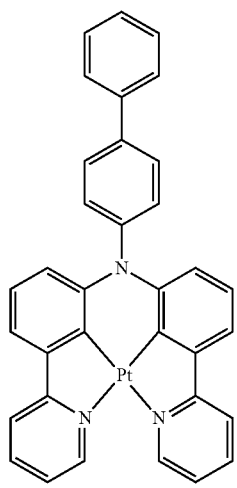 | 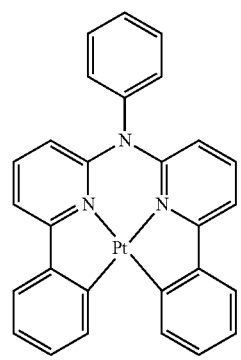 |
| 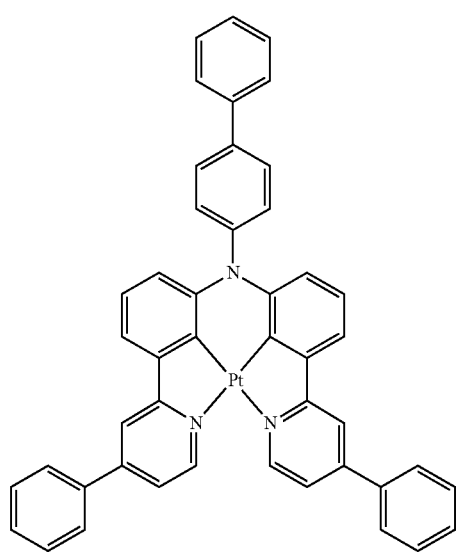 | 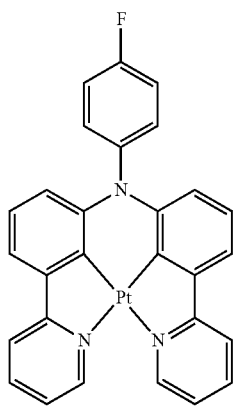 |

-continued
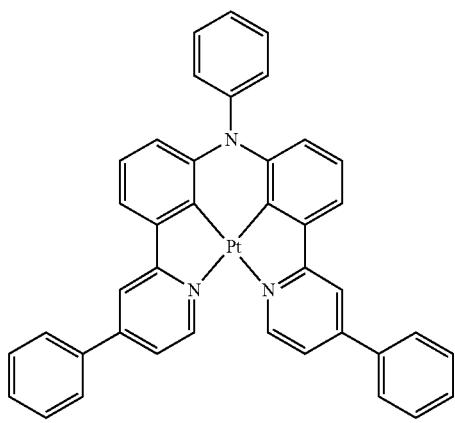
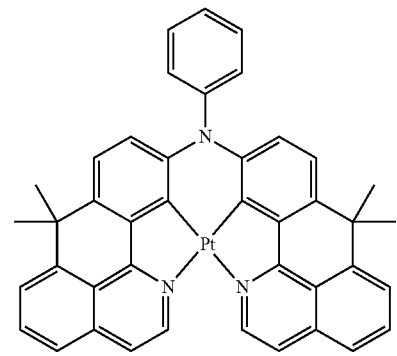
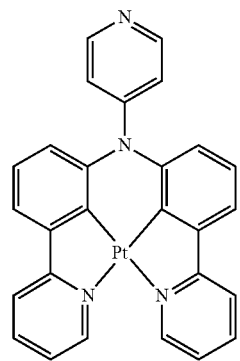
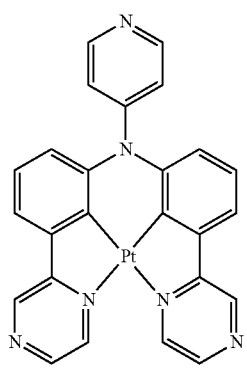
-continued
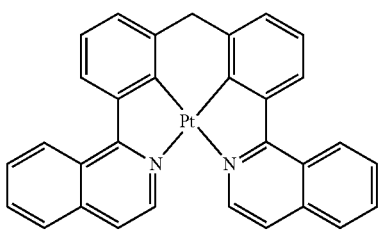
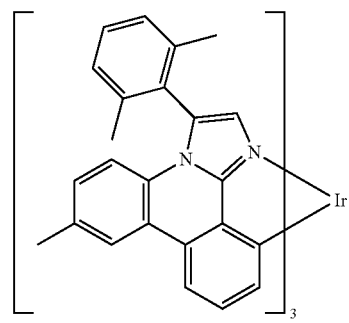
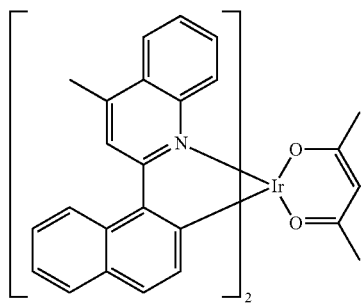
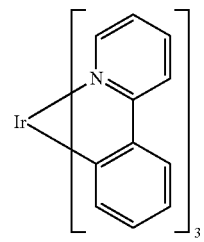
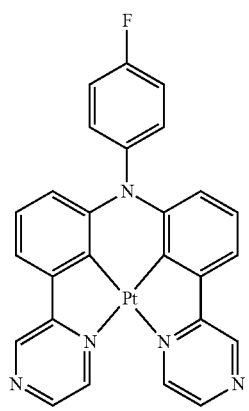

107
-continued
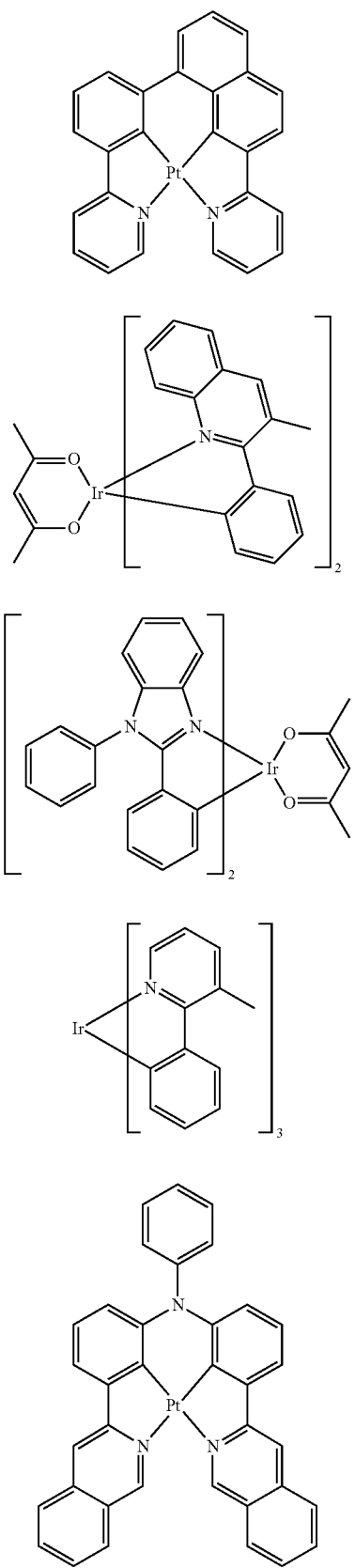
108
-continued
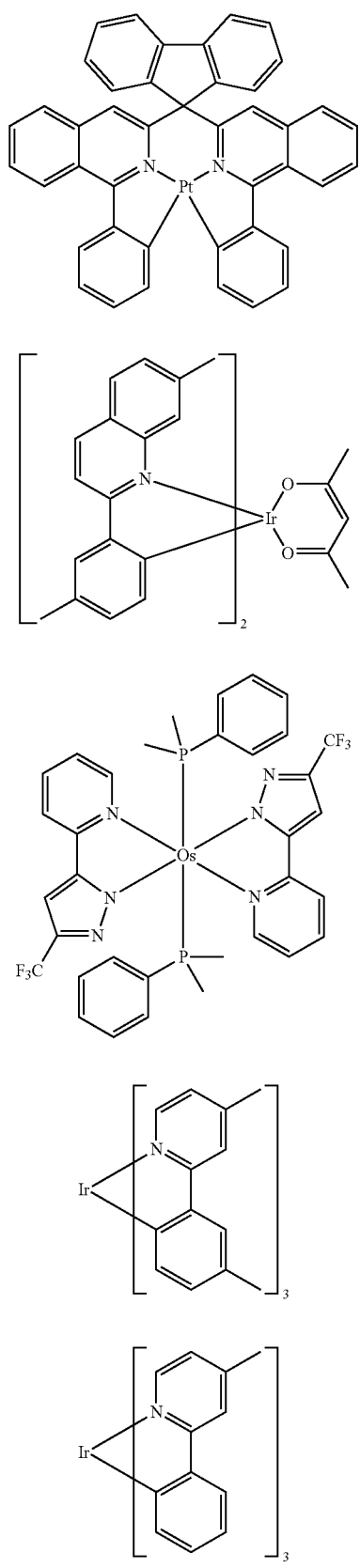

109
-continued
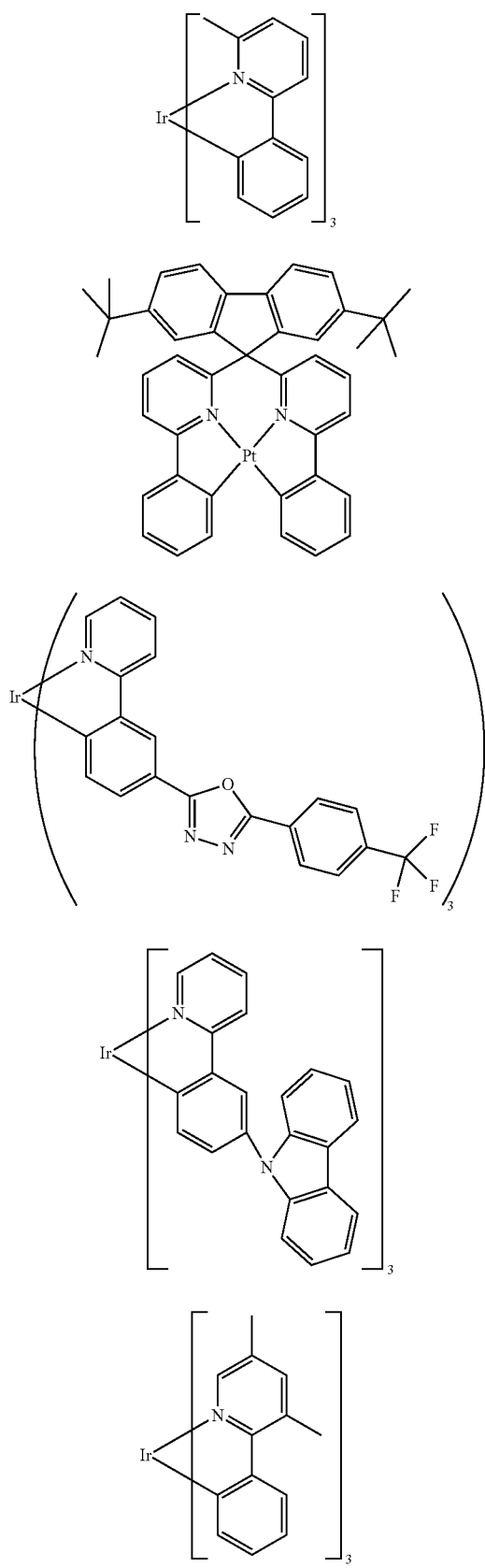
110
-continued
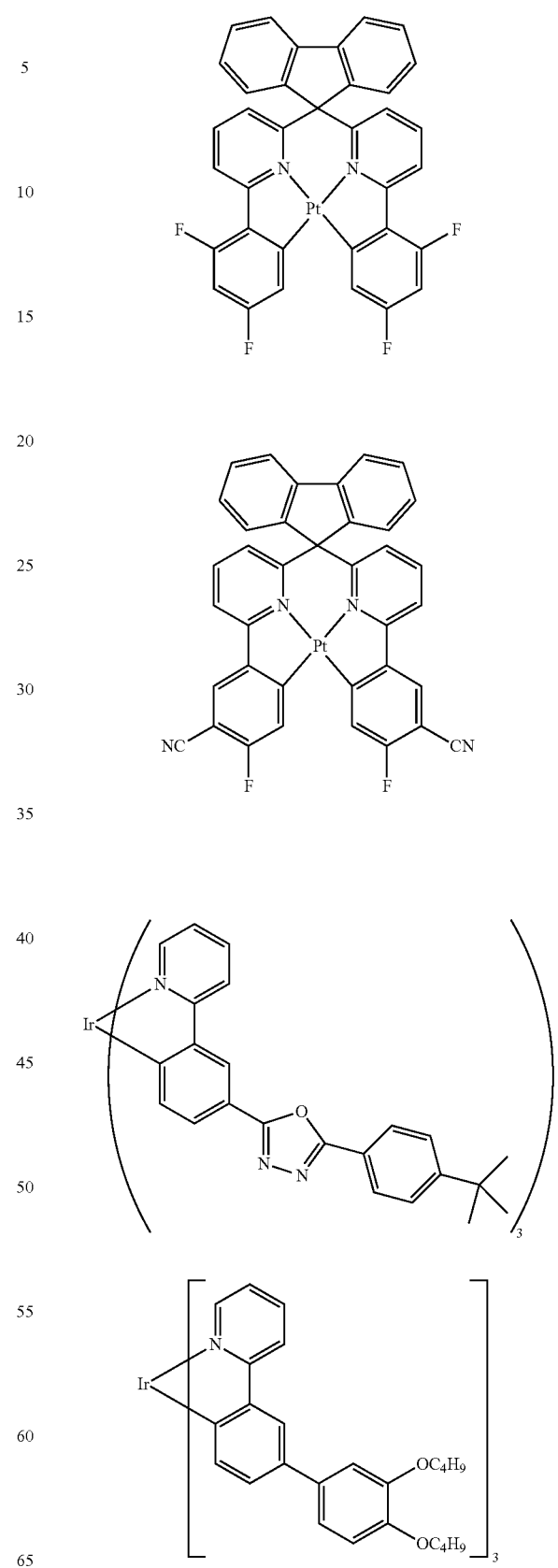

111
-continued
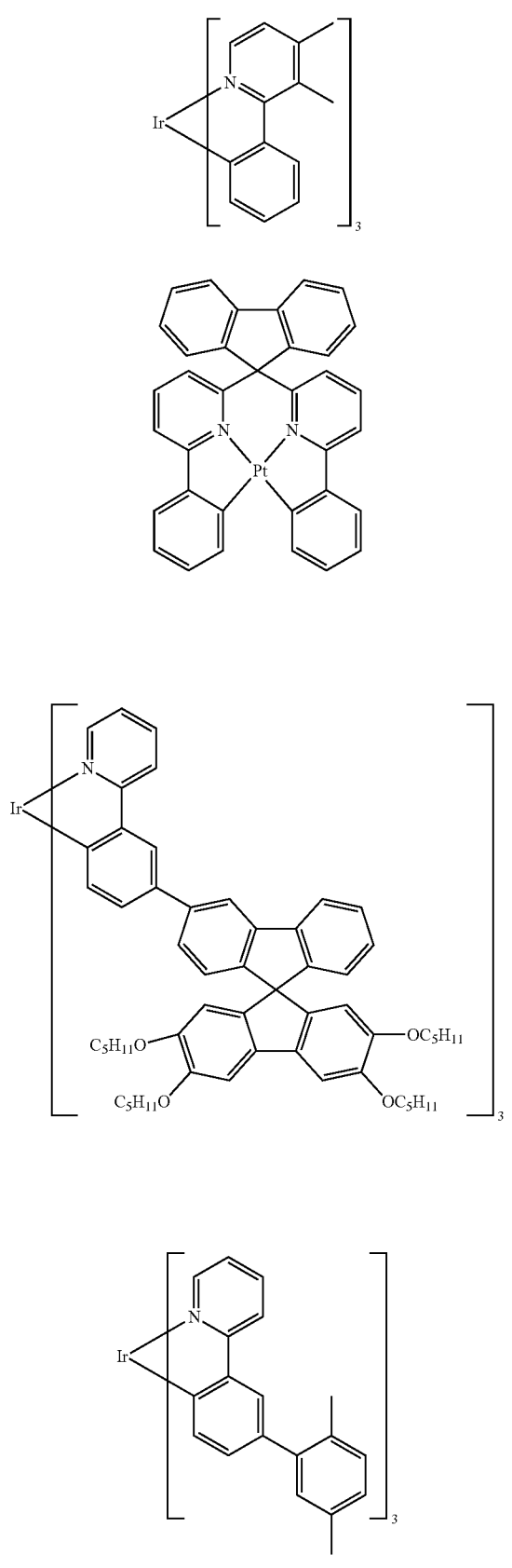
112
-continued
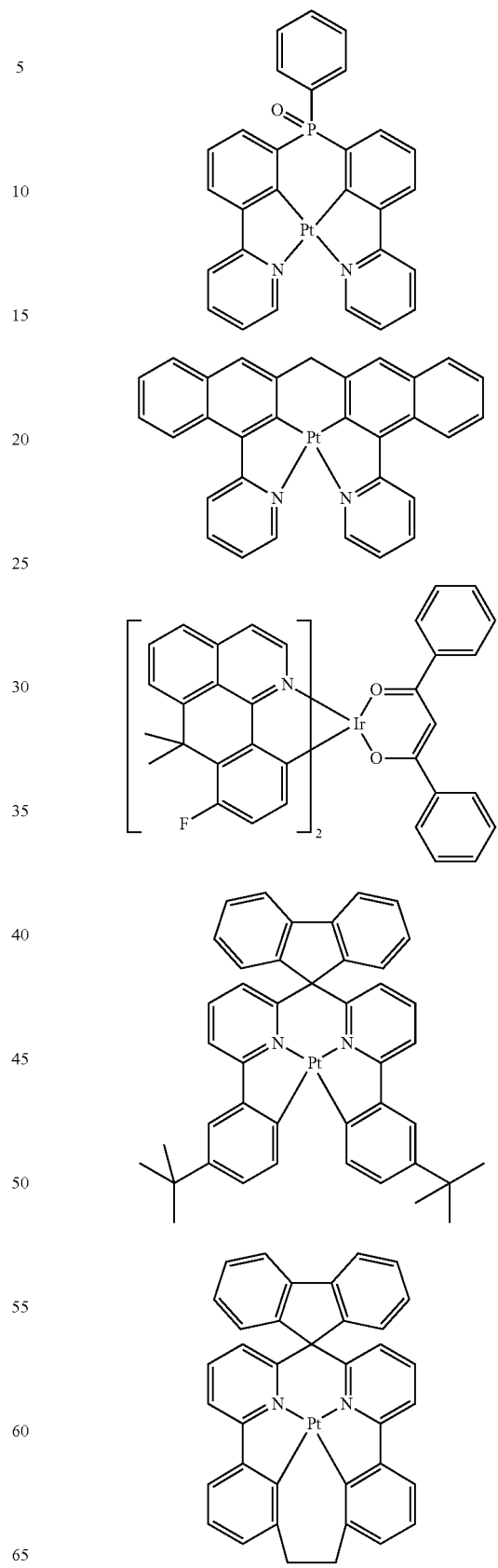

| 113 -continued | 114 -continued |
|---|---|
| 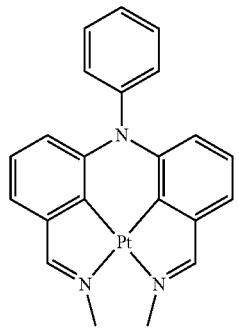 | 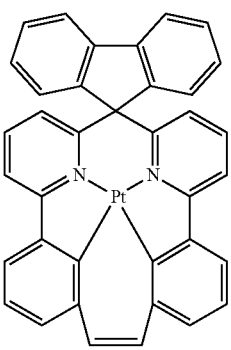 |
| 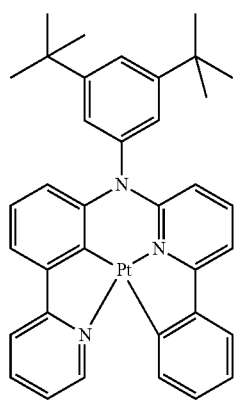 | 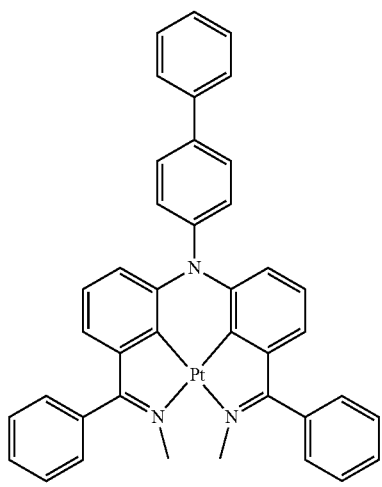 |
| 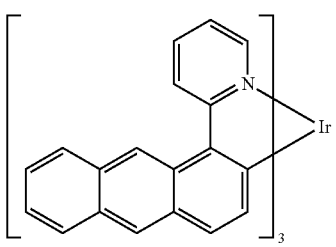 | 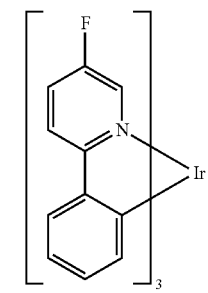 |
| 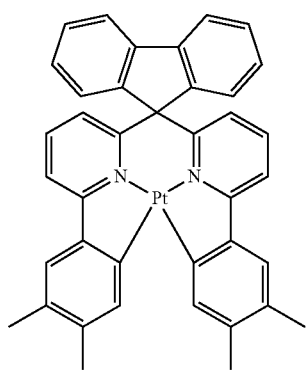 | 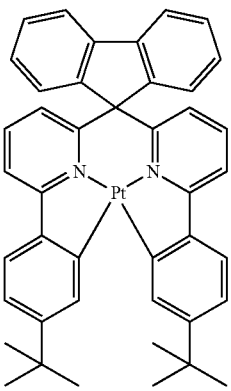 |

| 115 -continued | | 116 -continued |
|---|---|---|
| 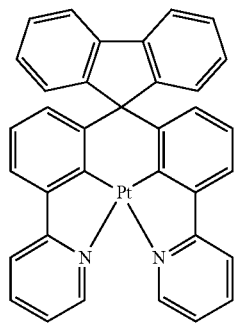 | | 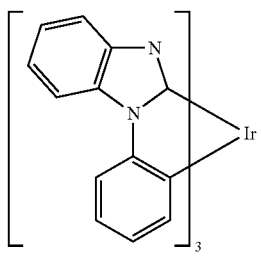 |
| 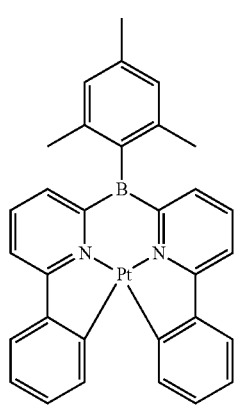 | | 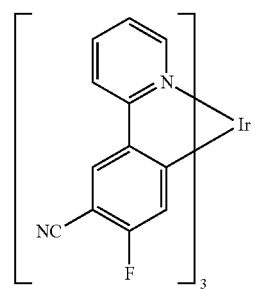 |
| 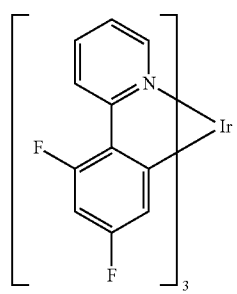 | | 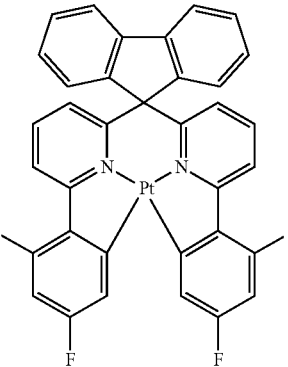 |
| 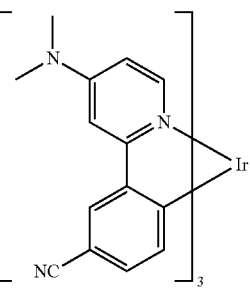 | | 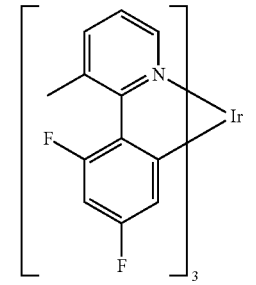 |
| 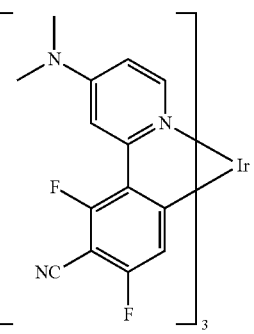 | | 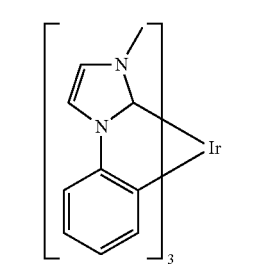 |

117
-continued
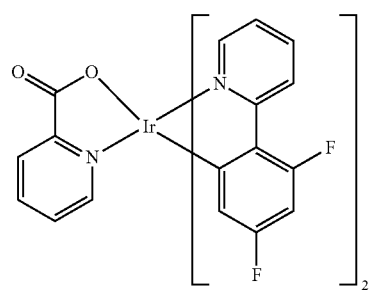
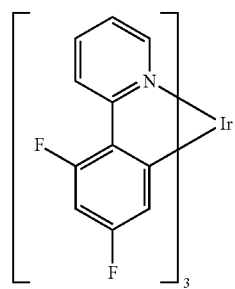
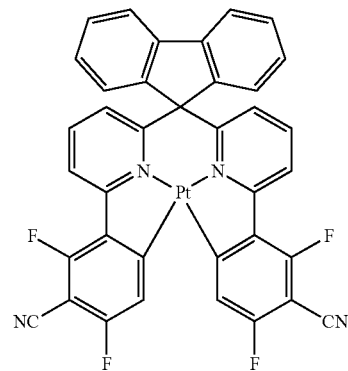
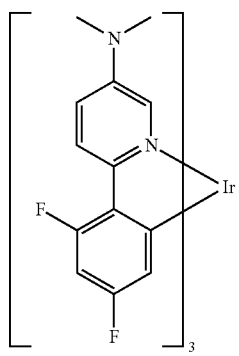
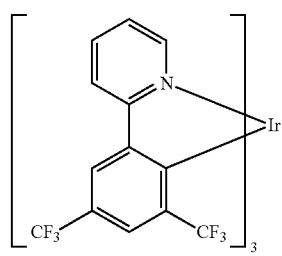
118
-continued
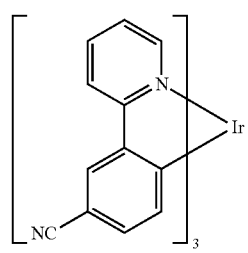
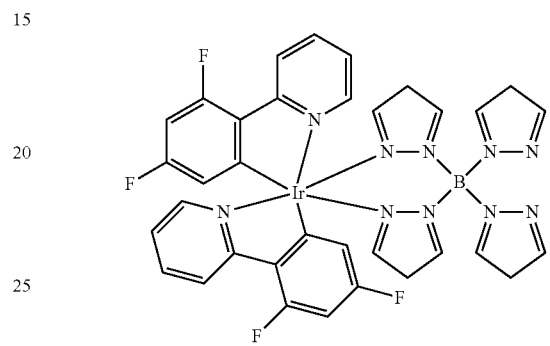
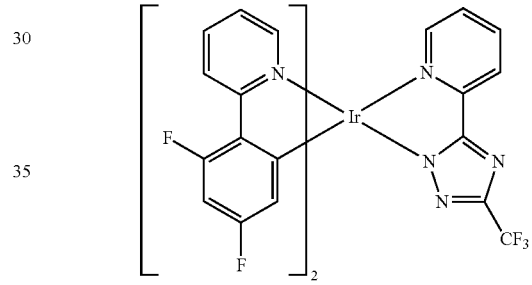
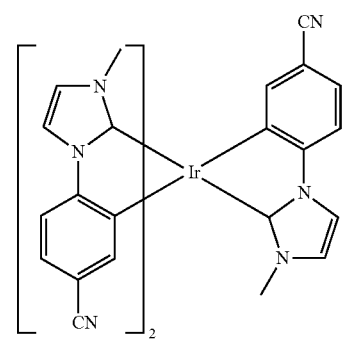
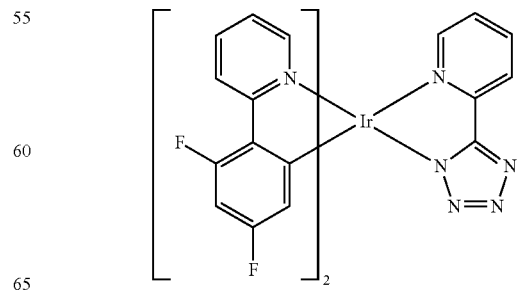

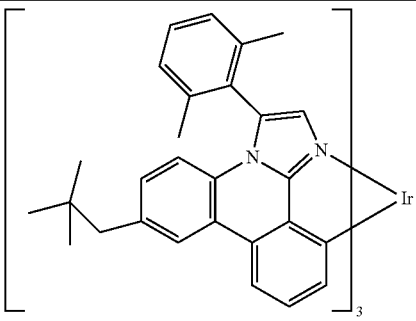

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred fluorescent dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of fluorescent dopants from the class of the styrylamines are substituted or unsubstituted tristilbenamines or the fluorescent dopants described in WO 2006/000388, WO 2006/058737, WO 2006/000389, WO 2007/065549 and WO 2007/115610. Preference is furthermore given to the condensed hydrocarbons disclosed in WO 2010/012328. Suitable fluorescent dopants are furthermore the derivatives disclosed in JP 2006/001973, WO 2004/047499, WO 2006/098080, WO 2007/065678, US 2005/0260442 and WO 2004/092111.

Suitable matrix materials, preferably for fluorescent dopants, are materials from various classes of substance. Preferred matrix materials are selected from the classes of the oligoarylenes (for example 2, 2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes containing naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes conaining anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with the applications WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAIQ.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for exampie, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) or (II) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds according to the invention can be employed in displays, as light sources in lighting applications and as light sources in medical and/or cosmetic applications (for example light therapy).

The compounds according to the invention and the organic electroluminescent devices according to the invention are distinguished by the following surprising advantages over the prior art:

1. The compounds according to the invention are very highly suitable for use in an electron-transport layer of an organic electroluminescent device.
2. The compounds according to the invention, employed as matrix material for fluorescent or phosphorescent emitters, result in very high efficiencies and in long lifetimes. This applies, in particular, if the compounds are employed as matrix material for a phosphorescent emitter.
3. The compounds according to the invention are suitable not only as matrix for red- and green-phosphorescent compounds, but also for blue-phosphorescent compounds.
4. The compounds according to the invention, employed in organic electroluminescent devices, result in high efficiencies and in steep current/voltage curves with low use and operating voltages.
5. The compounds according to the invention have high temperature stability and high oxidation stability in solution and are thus readily processable.

The invention is explained in greater detail by the following use examples, where the invention is not restricted to the scope of the examples.

WORKING EXAMPLES

1. Synthesis of Intermediates A to D

Synthesis of Intermediate A:

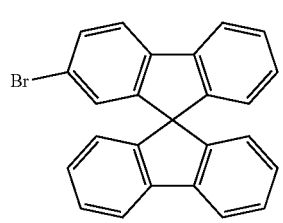

A 10.3 mmol of 9,9'-spirobifluorene are dissolved in 30 ml of CH$_2$Cl$_2$ and protected against the incidence of light. 10.3 mmol of NBS are added in portions over the course of 30 min with stirring. After 24 h, water is added to the mixture. The organic phase is dried over Na$_2$SO$_4$ and evaporated in a rotary evaporator. The residue is recrystallised with MeOH.

The following compounds are obtained analogously:

| Ex. | Starting material 1 | Product | Yield |
|---|---|---|---|
| B | ![structure] | ![structure with Br] | 44% |

-continued
| Ex. | Starting material 1 | Product | Yield |
|---|---|---|---|
| C | 1174660-93-5 | | 38% |
| D | 1092539-80-4 | | 42% |
2. Synthesis of Compounds 1 to 8 According to the Invention
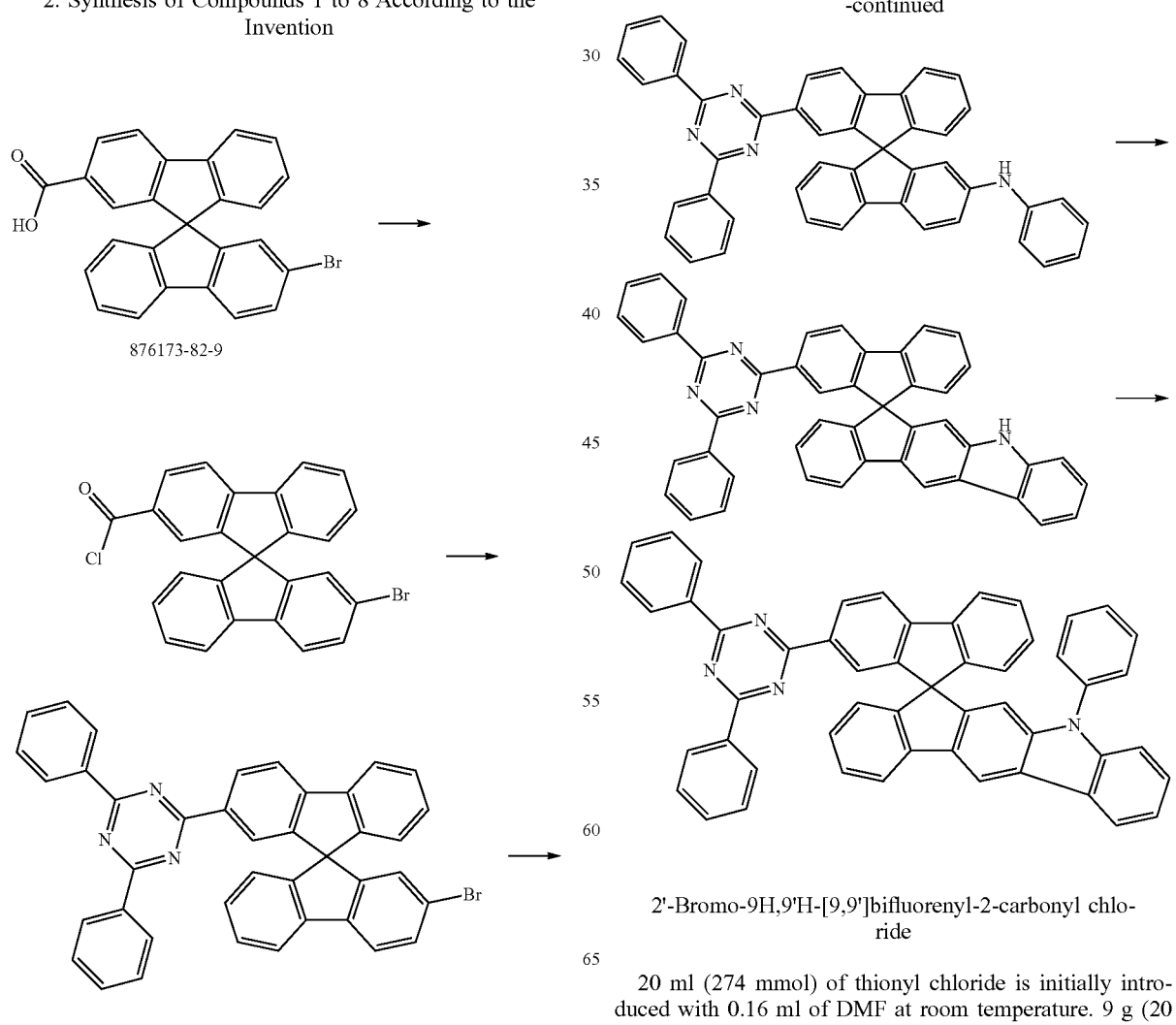
2'-Bromo-9H,9'H-[9,9']bifluorenyl-2-carbonyl chloride
20 ml (274 mmol) of thionyl chloride is initially introduced with 0.16 ml of DMF at room temperature. 9 g (20 mmol) of 2'-bromo-9H,9'H-[9,9']bifluorenyl-2-carboxylic acid are then added. The reaction mixture is stirred at 60° C. for 1 h. The remaining thionyl chloride is then distilled off and recrystallised from toluene.

Yield: 9.1 g (19 mmol), 98% of theory, purity according to $^1$H-NMR about 97%.

2-(2'-Bromo-9H,9'H-[9,9']bifluorenyl-2-yl)-4,6-diphenyl-1,3,5-triazine 42 g (89 mmol) of 2'-bromo-9H,9'H-[9,9']bifluorenylcarbonyl chloride, 11.90 g (89 mmol) of aluminium trichloride and 1.9 ml (27 mmol) of thionyl chloride are suspended in 260 ml of dichlorobenzene. 19.3 ml (187 mmol) of benzonitrile are then added slowly. The reaction mixture is stirred at 100° C. for 1 h. 9.55 g (179 mmol) of ammonium chloride are added, and the batch is stirred at 100° C. for 16 h. After cooling to room temperature, the reaction solution is added to 3.5 l of methanol and stirred for 45 min. The precipitated solid is filtered off and recrystallised from toluene.

Yield: 51 g (80 mmol), 90% of theory, purity according to $^1$H-NMR about 97%.

[2'-(4,6-Diphenyl-1,3,5-triazin-2-yl)-9H,9'H-[9,9']bifluorenyl-2-yl]phenylamine 117 g (183 mmol) of 2-(2'-bromo-9H,9'H-[9,9']bifluorenyl-2-yl)-4,6-diphenyl-1,3,5-triazine, 20 ml of aniline (220 mmol), 1.5 g of DPPF (2.7 mmol), 0.5 g of palladium(II) acetate and 45 g of sodium tert-butoxide (486 mmol) are heated at the boil in 1.5 l of toluene for 18 h under protective atmosphere. The mixture is subsequently partitioned between toluene and water, the organic phase is washed three times with water and dried over Na$_2$SO$_4$ and evaporated in a rotary evaporator. The residue remaining is recrystallised from heptane/ethyl acetate.

Yield: 106 g (162 mmol), 89% of theory, purity according to $^1$H-NMR about 97%.

12-[2-(4,6-Diphenyl-1,3,5-triazin-2-yl)-9H-fluoren-9-yl]-10,12-dihydro-10-azaindeno[2,1-b]fluorene 35 ml of pivalic acid are added to 22.8 g (35 mmol) of [2'-(4,6-diphenyl-1,3,5-triazin-2-yl)-9H,9'H-[9,9']bifluorenyl-2-yl]phenylamine, 0.4 g of palladium(II) acetate (1.78 mmol) and 0.5 g of potassium carbonate (3.62 mmol), and the mixture is stirred at 120° C. for 9 h. After this time, 0.4 g of palladium(II) acetate (1.78 mmol) is added, and the mixture is stirred at 120° C. for a further 9 h. 200 ml of dichloromethane and 0. µM Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane.

Yield: 18.2 g (28 mmol), 80% of theory, purity according to $^1$H-NMR about 97%.

12-[2-(4,6-Diphenyl-1,3,5-triazin-2-yl)-9H-fluoren-9-yl]-10-phenyl-10,12-dihydro-10-azaindeno[2,1-b]fluorene (Example 1)

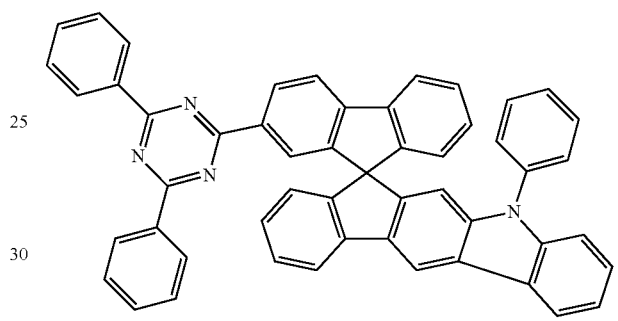

69 g (106 mmol) of 12-[2-(4,6-diphenyl-1,3,5-triazin-2-yl)-9H-fluoren-9-yl]-10,12-dihydro-10-azaindeno[2,1-b]fluorene, 17.8 g (114 mmol) of bromobenzene and 30.5 g of NaOtBu are suspended in 1.5 l of p-xylene. 0.5 g (2.11 mmol) of Pd(OAc)$_2$ and 1.6 ml of a 1M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, purity is 99.9%.

Yield: 74 g (102 mmol), 97% of theory

The following compounds are obtained analogously:

| Ex. | Starting material 1 | Starting material 2 | Product | Yield |
|---|---|---|---|---|
| 2 | 1233200-68-4 | Br-phenyl | (structure) | 59% |

-continued

| Ex. | Starting material 1 | Starting material 2 | Product | Yield |
|---|---|---|---|---|
| 3 | 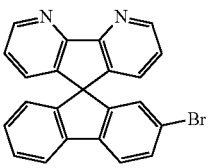 [SMILES: Brc1ccc2c(c1)C1(c3ccccc3-2)c2cccnc2-c2ncccc21]<br>905853-26-1 | 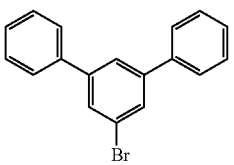 [SMILES: Brc1cc(-c2ccccc2)cc(-c2ccccc2)c1]<br>103068-20-8<br>Only the last three steps in the scheme are carried out | 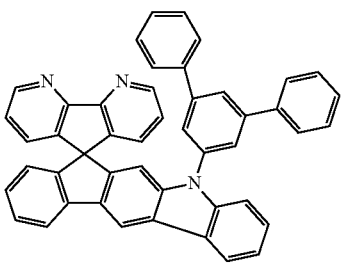 [SMILES: c1ccc(-c2cc(-c3ccccc3)cc(-n3c4ccccc4c4cc5c(cc43)C3(c4ccccc4-5)c4cccnc4-c4ncccc43)c2)cc1] | 66% |
| 4 | 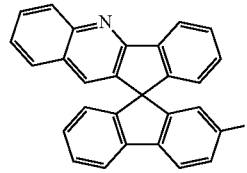<br>1262330-86-8 | 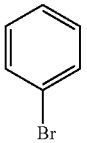<br>Only the last three steps in the scheme are carried out | 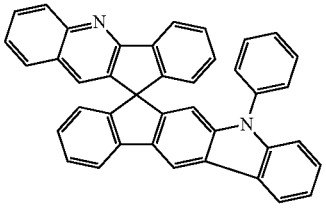 [SMILES: c1ccc(-n2c3ccccc3c3cc4c(cc32)C2(c3ccccc3-4)c3ccccc3-c3nc4ccccc4cc32)cc1] | 69% |
| 5 | 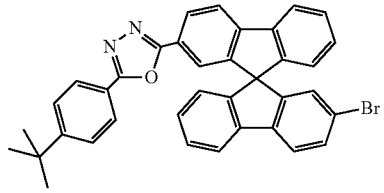 [SMILES: CC(C)(C)c1ccc(-c2nnc(-c3ccc4c(c3)C3(c5ccccc5-c5ccc(Br)cc53)c3ccccc3-4)o2)cc1]<br>876173-84-1 | 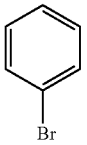<br>Only the last three steps in the scheme are carried out | 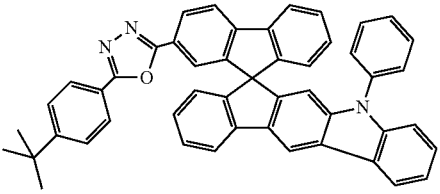 [SMILES: CC(C)(C)c1ccc(-c2nnc(-c3ccc4c(c3)C3(c5ccccc5-4)c4ccccc4-c4cc5c6ccccc6n(-c6ccccc6)c5cc43)o2)cc1] | 54% |
| 6 | 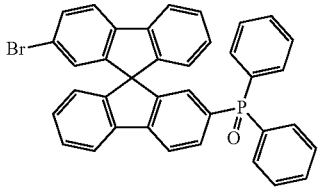 [SMILES: O=P(c1ccccc1)(c1ccccc1)c1ccc2c(c1)C1(c3ccccc3-c3ccc(Br)cc31)c1ccccc1-2]<br>B | 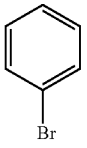<br>Only the last three steps in the scheme are carried out | 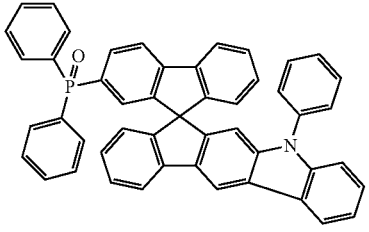 [SMILES: O=P(c1ccccc1)(c1ccccc1)c1ccc2c(c1)C1(c3ccccc3-2)c2ccccc2-c2cc3c4ccccc4n(-c4ccccc4)c3cc21] | 45% |
| 7 | 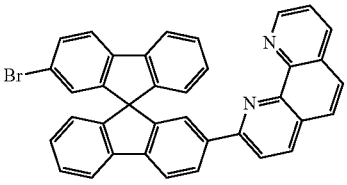 [SMILES: Brc1ccc2c(c1)C1(c3ccccc3-2)c2ccccc2-c2ccc(-c3ccc4ccc5cccnc5c4n3)cc21]<br>C | 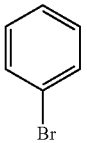<br>Only the last three steps in the scheme are carried out | 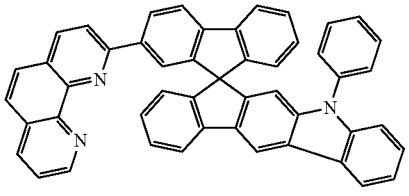 [SMILES: c1ccc(-n2c3ccccc3c3cc4c(cc32)C2(c3ccccc3-c3ccc(-c5ccc6ccc7cccnc7c6n5)cc32)c2ccccc2-4)cc1] | 56% |

| Ex. | Starting material 1 | Starting material 2 | Product | Yield |
|---|---|---|---|---|
| 8 |  D | 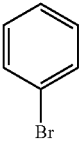 Only the last three steps in the scheme are carried out | 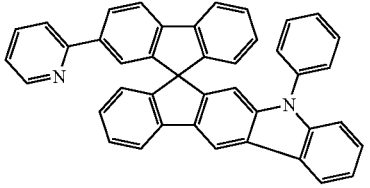 [SMILES: c1ccc(-n2c3ccccc3c3cc4c(cc32)C2(c3ccccc3-c3ccc(-c5ccccn5)cc32)c2ccccc2-4)cc1] | 49% |

3. Synthesis of Compounds 9-13 According to the Invention

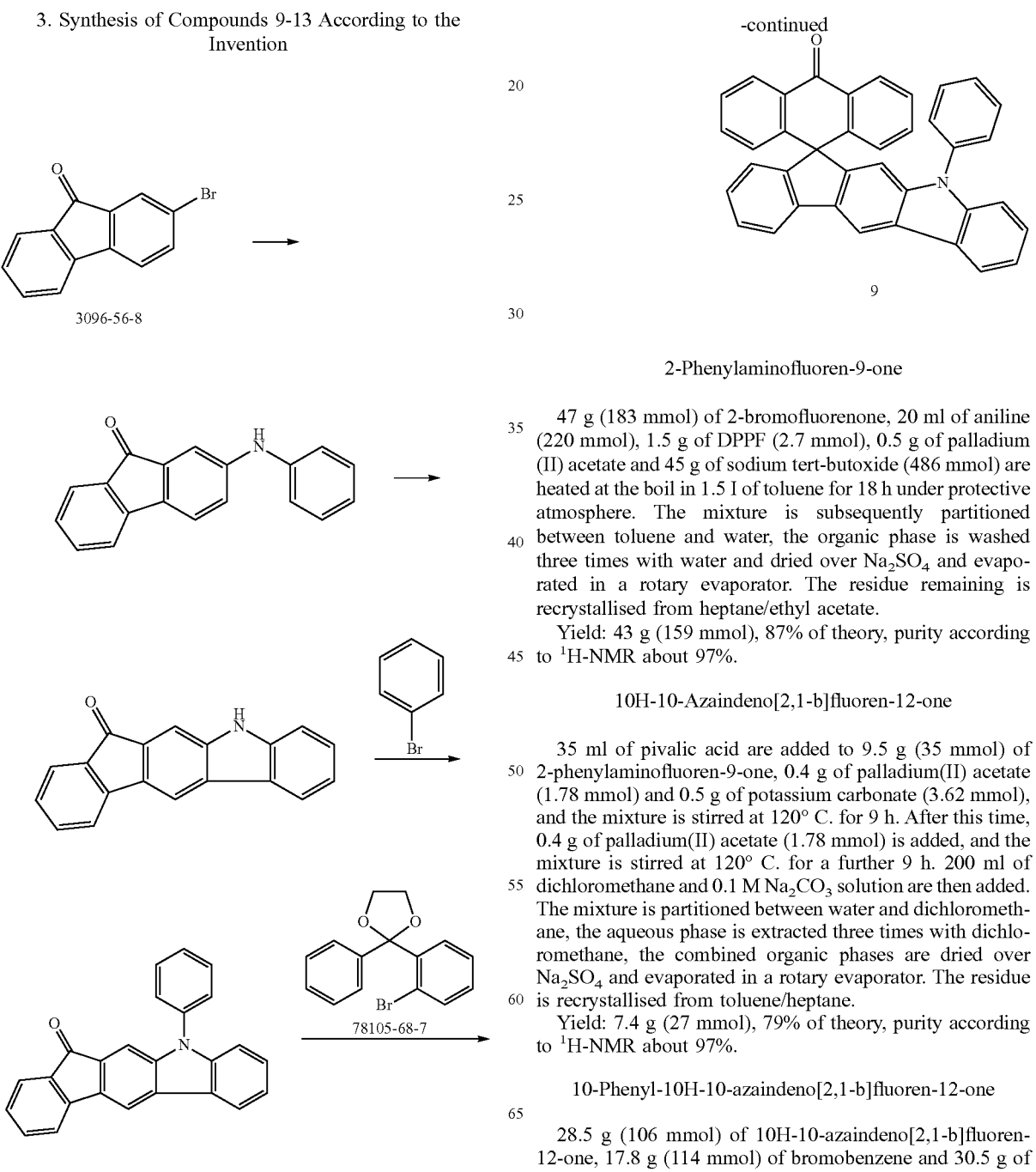

2-Phenylaminofluoren-9-one 47 g (183 mmol) of 2-bromofluorenone, 20 ml of aniline (220 mmol), 1.5 g of DPPF (2.7 mmol), 0.5 g of palladium (II) acetate and 45 g of sodium tert-butoxide (486 mmol) are heated at the boil in 1.5 l of toluene for 18 h under protective atmosphere. The mixture is subsequently partitioned between toluene and water, the organic phase is washed three times with water and dried over $Na_2SO_4$ and evaporated in a rotary evaporator. The residue remaining is recrystallised from heptane/ethyl acetate.

Yield: 43 g (159 mmol), 87% of theory, purity according to $^1$H-NMR about 97%.

10H-10-Azaindeno[2,1-b]fluoren-12-one 35 ml of pivalic acid are added to 9.5 g (35 mmol) of 2-phenylaminofluoren-9-one, 0.4 g of palladium(II) acetate (1.78 mmol) and 0.5 g of potassium carbonate (3.62 mmol), and the mixture is stirred at 120° C. for 9 h. After this time, 0.4 g of palladium(II) acetate (1.78 mmol) is added, and the mixture is stirred at 120° C. for a further 9 h. 200 ml of dichloromethane and 0.1 M $Na_2CO_3$ solution are then added. The mixture is partitioned between water and dichloromethane, the aqueous phase is extracted three times with dichloromethane, the combined organic phases are dried over $Na_2SO_4$ and evaporated in a rotary evaporator. The residue is recrystallised from toluene/heptane.

Yield: 7.4 g (27 mmol), 79% of theory, purity according to $^1$H-NMR about 97%.

10-Phenyl-10H-10-azaindeno[2,1-b]fluoren-12-one 28.5 g (106 mmol) of 10H-10-azaindeno[2,1-b]fluoren-12-one, 17.8 g (114 mmol) of bromobenzene and 30.5 g of NaOtBu are suspended in 1.5 l of p-xylene. 0.5 g (2.11 mmol) of Pd(OAc)₂ and 1.6 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, purity is 99.9%.

Yield: 32 g (95 mmol), 90% of theory, purity according to ¹H-NMR about 97%.

Synthesis of the Spiro Compound (Example 9)

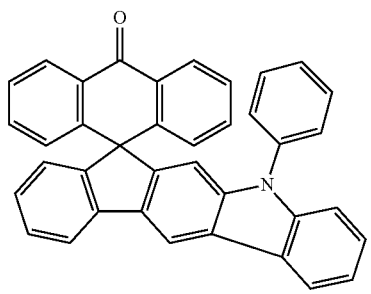 [SMILES: O=C1c2ccccc2C2(c3ccccc31)c1ccccc1-c1cc3c4ccccc4n(-c4ccccc4)c3cc12]

65 ml (160 mmol) of n-butyllithium (2.5 M in hexane) are added over the course of 30 minutes at −78° C. to a solution of 43.6 g (143 mmol) of 2-(−2-bromophenyl)-2-phenyl-1,3-dioxolane, dissolved in 200 ml of anhydrous THF, and the mixture is then brought to 0° C. The lithiated compound is transferred into a dropping funnel using a syringe and slowly added dropwise at 0° C. to a suspension of 48 g (140 mmol) of 10-phenyl-10H-10-azaindeno[2,1-b]fluoren-12-one in 30 ml of anhydrous THF. The solution is brought to room temperature and kept at this temperature for 4 h, then saturated ammonium chloride solution is added. The aqueous phase is extracted with CH₂Cl₂ (3×15 ml), and the organic phases are dried over anhydrous sodium sulfate. After removal of the solvent, a reddish liquid is obtained which is a mixture of several isomers. The liquid is dissolved in 100 ml of glacial acetic acid and heated under reflux, a few drops of concentrated HCl are then added, and the mixture is heated under reflux for a further minute. Water is added until cloudiness forms, the mixture is then cooled to room temperature and filtered. The acidic aqueous phase is extracted with CH₂Cl₂ and dried over anhydrous sodium sulfate. The solvent is subsequently removed in a rotary evaporator.

Yield: 34 g (68 mmol), 50% of theory, purity according to ¹H-NMR about 93%.

The following compounds are obtained analogously:

| Ex. | Starting material 1 | Starting material 2 | Product | Yield |
|---|---|---|---|---|
| 10 | ![structure] 3096-56-8 | ![structure] | ![structure] | 72% |
| 11 | ![structure] 354816-92-5 | Only the final reaction step in the scheme is carried out | ![structure] | 68% |

| Ex. | Starting material 1 | Starting material 2 | Product | Yield |
|---|---|---|---|---|
| 12 | 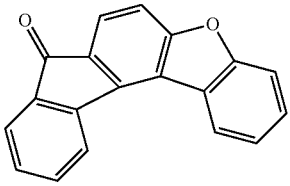 [SMILES: O=C1c2ccccc2-c2c1ccc1oc3ccccc3c21]<br>354816-91-4 | Only the final reaction step in the scheme is carried out | 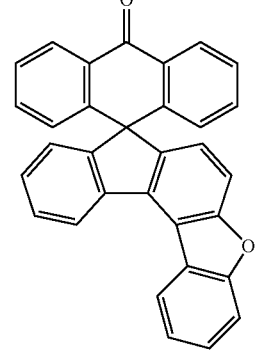 | 72% |
| 13 | 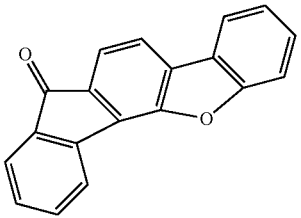 [SMILES: O=C1c2ccccc2-c2c1ccc1c2oc2ccccc21]<br>121073-95-8 | Only the final reaction step in the scheme is carried out | 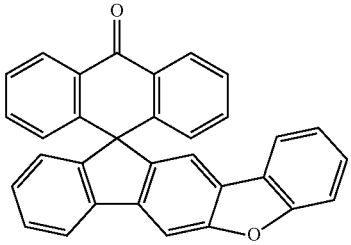 [SMILES: O=C1c2ccccc2C2(c3ccccc31)c1ccccc1-c1cc3oc4ccccc4c3cc12] | 70% |

4. Synthesis of Compounds 14-17 According to the Invention

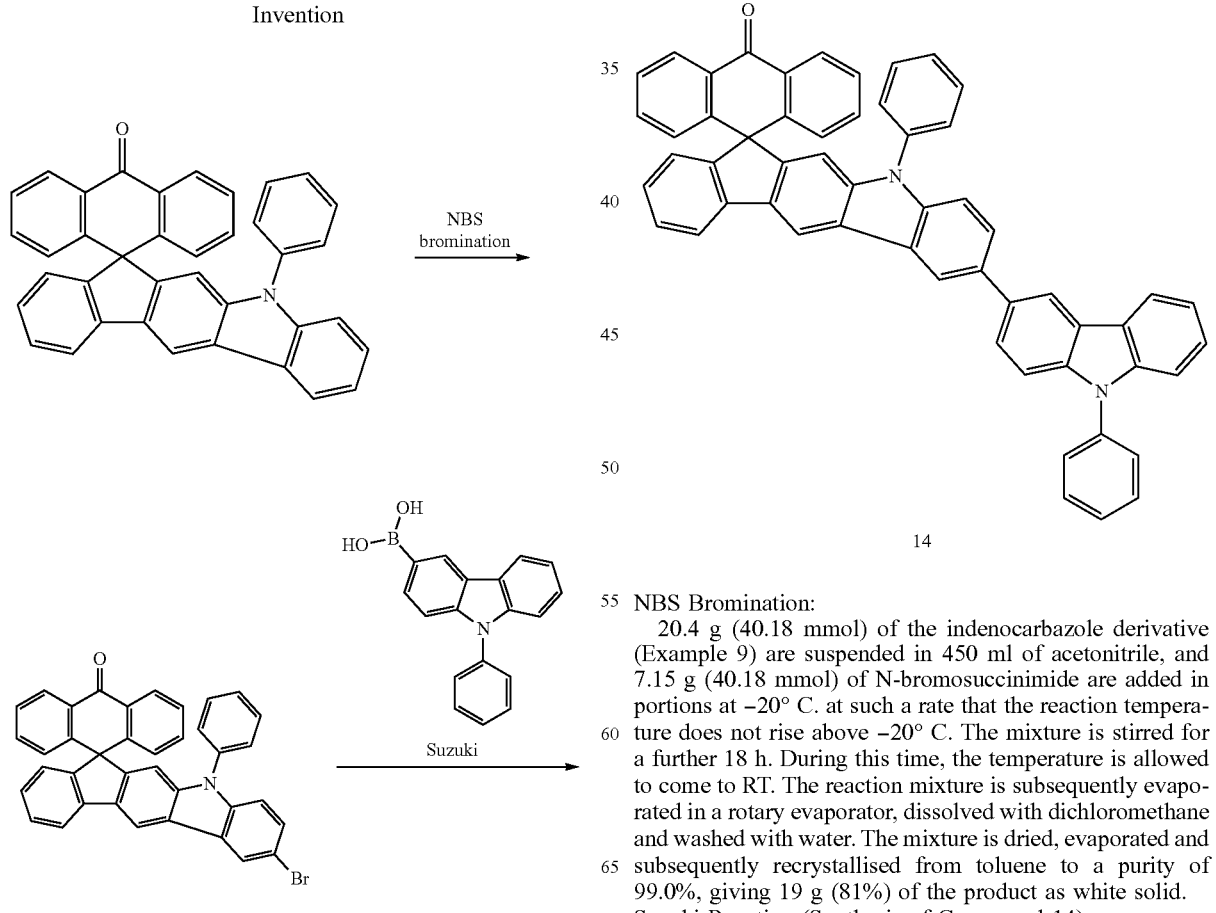

NBS Bromination:

20.4 g (40.18 mmol) of the indenocarbazole derivative (Example 9) are suspended in 450 ml of acetonitrile, and 7.15 g (40.18 mmol) of N-bromosuccinimide are added in portions at −20° C. at such a rate that the reaction temperature does not rise above −20° C. The mixture is stirred for a further 18 h. During this time, the temperature is allowed to come to RT. The reaction mixture is subsequently evaporated in a rotary evaporator, dissolved with dichloromethane and washed with water. The mixture is dried, evaporated and subsequently recrystallised from toluene to a purity of 99.0%, giving 19 g (81%) of the product as white solid.

Suzuki Reaction (Synthesis of Compound 14):

12 g (42 mmol) of (9-phenylcarbazol-3yl)boronic acid and 30 g (52.4 mmol) of the indenocarbazole derivative which is brominated in the 2-position (CAS 854952-58-2) are dissolved in a degassed mixture of 135 ml of water, 315 ml of dioxane and 315 ml of toluene, and 5.33 g (50.31 mmol) of $Na_2CO_3$ are added. The reaction mixture is degassed, and 0.96 g (0.84 mmol) of Pd tetrakistriphenylphosphine catalyst is added. The mixture is heated under reflux for 18 h. After cooling, dichloromethane is added (heterogeneous mixture), the water phase is separated off, and the organic phase is evaporated azeotropically with toluene. The reaction product is crystallised from DMSO, giving 29 g (67%) of the product having a purity of 99.98% as white solid.

The following compounds are obtained analogously:

5. Device Examples: Production of OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in Examples V1-E19 below (see Tables 1 and 2). Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP A14083 from Heraeus Clevios Deutschland, applied by spin coating from aqueous solution, dried at 180° in air for 10 min after the spin coating) for improved processing. These coated glass plates form the substrates to

| Ex. | Starting material 1 | Starting material 2 | Product | Yield |
|---|---|---|---|---|
| 15 | [structure] | [structure] 128388-54-5 | [structure] | 79% |
| 16 | [structure] | [structure] | [structure] | 81% |
| 17 | [structure] | [structure] 100124-06-9 | [structure] | 77% | which the OLEDs are applied. The OLEDs have in principle the following layer structure: substrate/optional hole-injection layer (HIL)/holetransport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as ST1:2:TEG1 (65%:25%:10%) here means that material ST1 is present in the layer in a proportion by volume of 65%, material 2 is present in the layer in a proportion of 25% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$. The lifetime LT is defined as the time after which the luminous density has dropped to a certain proportion L1 from the initial luminous density L0 on operation at constant current. An expression of L0=4000 cd/m$^2$ and L1=80% in Table 2 means that the lifetime indicated in column LT corresponds to the time after which the initial luminous density has dropped from 4000 cd/m$^2$ to 3200 cd/m$^2$.

The data for the various OLEDs are summarised in Table 2. Examples V1-V5 are comparative examples in accordance with the prior art, Examples E1-E19 show data of OLEDs comprising materials according to the invention.

Some of the examples are explained in greater detail below in order to illustrate the advantages of the compounds according to the invention. However, it should be pointed out that this only represents a selection of the data shown in Table 2.

Use of Compounds According to the Invention as Matrix Materials for Phosphorescent Dopants On use of materials in accordance with the prior art which contain an anthracene between the spiro unit and the electron-withdrawing unit, an external quantum efficiency of 8.1% is achieved in the case of green emission and an external quantum efficiency of 6.7% is achieved in the case of red emission. The lifetime at an initial luminous density of 10000 cd/m$^2$ (green, drop to 70%) or 4000 cd/m$^2$ (red, drop to 80%) is significantly less than 100 h (Examples V1, V2). These values are very low for phosphorescent dopants, which is shown, for example, by Example E2 comprising materials according to the invention: external quantum efficiencies of greater than 17% and lifetimes of greater than 250 h can be achieved with the compounds according to the invention.

Similar situations arise if material S1 is used in combination with a second material in a mixed-matrix system (cf. Examples V3, V4, E3, E5, E13, E14, E19).

Good performance data are already obtained with materials in accordance with the prior art in which the electron-deficient group (for example a triazine) is bonded to the carbazole unit of the compound. An external quantum efficiency of almost 15%, a power efficiency of 44 lm/W and a lifetime of 220 h are achieved with a compound IC$_4$ of this type, for example. However, if the electron-deficient group is, as in the case of the materials according to the invention, bonded to the spirobifluorene unit, a significant improvement in the power efficiency by 25% is obtained, the external quantum efficiency increases by about 10%, the lifetime by about 30% and the operating voltage improves by 0.4 V (Examples V5, E1).

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| V1 | — | SpA1 70 nm | HATCN 5 nm | SpMA1 90 nm | S1:TEG1 (90%:10%) 30 nm | — | ST2:LiQ (50%:50%) 40 nm | — |
| V2 | — | SpA1 90 nm | HATCN 5 nm | SpMA1 130 nm | S1:TER1 (92%:8%) 40 nm | IC1 10 nm | ST2:LiQ (50%:50%) 30 nm | — |
| V3 | — | SpA1 70 nm | HATCN 5 nm | SpMA1 90 nm | ST1:S1:TEG1 (60%:30%:10%) 30 nm | IC1 10 nm | ST2:LiQ (50%:50%) 30 nm | — |
| V4 | — | SpA1 70 nm | HATCN 5 nm | SpMA1 90 nm | S1:IC3:TEG1 (30%:60%:10%) 30 nm | IC1 10 nm | ST2:LiQ (50%:50%) 30 nm | — |
| V5 | — | SpA1 70 nm | HATCN 5 nm | SpMA1 90 nm | IC4:TEG1 (90%:10%) 30 nm | — | ST2:LiQ (50%:50%) 40 nm | — |
| E1 | — | SpA1 70 nm | HATCN 5 nm | SpMA1 90 nm | 1:TEG1 (90%:10%) 30 nm | — | ST2:LiQ (50%:50%) 40 nm | — |
| E2 | — | SpA1 70 nm | HATCN 5 nm | SpMA1 90 nm | IC1:TEG1 (90%:10%) 30 nm | — | 1 40 nm | LiQ 3 nm |
| E3 | HATCN 5 nm | SpA1 140 nm | HATCN 5 nm | SpMA1 20 nm | ST1:2:TEG1 (65%:25%:10%) 40 nm | ST1 5 nm | ST2:LiQ (50%:50%) 25 nm | — |
| E4 | — | SpA1 70 nm | HATCN 5 nm | SpMA1 90 nm | 3:TEG1 (90%:10%) 30 nm | IC1 10 nm | ST2:LiQ (50%:50%) 30 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E5 | — | SpA1 70 nm | HATCN 5 nm | SpMA1 90 nm | IC1:3:TEG1 (25%:65%:10%) 30 nm | IC1 10 nm | ST2:LiQ (50%:50%) 30 nm | — |
| E6 | — | SpA1 90 nm | HATCN 5 nm | SpMA1 130 nm | 4:TER1 (92%:8%) 40 nm | IC1 10 nm | ST2:LiQ (50%:50%) 30 nm | — |
| E7 | — | SpA1 90 nm | HATCN 5 nm | SpMA1 130 nm | 6:TER1 (92%:8%) 40 nm | IC1 10 nm | ST2:LiQ (50%:50%) 30 nm | — |
| E8 | — | SpA1 70 nm | HATCN 5 nm | SpMA1 90 nm | IC1:TEG1 (90%:10%) 30 nm | — | 7 40 nm | LiF 1 nm |
| E9 | — | SpA1 90 nm | HATCN 5 nm | SpMA1 130 nm | 7:TER1 (92%:8%) 40 nm | IC1 10 nm | ST2:LiQ (50%:50%) 30 nm | — |
| E10 | — | SpA1 70 nm | HATCN 5 nm | SpMA1 90 nm | 9:TEG1 (90%:10%) 30 nm | — | ST2:LiQ (50%:50%) 40 nm | — |
| E11 | — | SpA1 70 nm | HATCN 5 nm | SpMA1 90 nm | 9:TEG1 (90%:10%) 30 nm | IC1 10 nm | ST2:LiQ (50%:50%) 30 nm | — |
| E12 | — | SpA1 70 nm | HATCN 5 nm | SpMA1 90 nm | 10:TEG1 (90%:10%) 30 nm | IC1 10 nm | ST2:LiQ (50%:50%) 30 nm | — |
| E13 | — | SpA1 70 nm | HATCN 5 nm | SpMA1 90 nm | 11:IC3:TEG1 (65%:25%:10%) 30 nm | IC1 10 nm | ST1:LiQ (50%:50%) 30 nm | — |
| E14 | — | SpA1 70 nm | HATCN 5 nm | SpMA1 90 nm | 12:IC3:TEG1 (60%:30%:10%) 30 nm | IC1 10 nm | ST1:LiQ (50%:50%) 30 nm | — |
| E15 | — | SpA1 90 nm | HATCN 5 nm | SpMA1 130 nm | 13:TER1 (90%:10%) 40 nm | IC1 10 nm | ST2:LiQ (50%:50%) 30 nm | — |
| E16 | — | SpA1 70 nm | HATCN 5 nm | SpMA1 90 nm | 16:TEG1 (90%:10%) 30 nm | IC1 10 nm | ST2:LiQ (50%:50%) 30 nm | — |
| E17 | — | SpA1 70 nm | HATCN 5 nm | SpMA1 90 nm | 17:TEG1 (90%:10%) 30 nm | IC1 10 nm | ST2:LiQ (50%:50%) 30 nm | — |
| E18 | — | SpA1 70 nm | HATCN 5 nm | SpMA1 90 nm | 14:TEG1 (90%:10%) 30 nm | IC1 10 nm | ST2:LiQ (50%:50%) 30 nm | — |
| E19 | — | SpA1 70 nm | HATCN 5 nm | SpMA1 90 nm | IC2:14:TEG1 (40%:50%:10%) 30 nm | IC1 10 nm | ST2:LiQ (50%:50%) 30 nm | — |

TABLE 2

Data for the OLEDs

| Ex. | U1000 (V) | CE1000 (cd/A) | PE1000 (lm/W) | EQE 1000 | CIE x/y at 1000 cd/m$^2$ | L0 | L1 % | LT (h) |
|---|---|---|---|---|---|---|---|---|
| V1 | 3.8 | 29 | 24 | 8.1% | 0.32/0.61 | 10000 | 70 | 70 |
| V2 | 4.8 | 6.2 | 4.1 | 6.7% | 0.66/0.33 | 4000 | 80 | 75 |
| V3 | 3.6 | 30 | 26 | 8.3% | 0.32/0.62 | 10000 | 70 | 95 |
| V4 | 3.7 | 27 | 23 | 7.4% | 0.32/0.61 | 10000 | 80 | 80 |
| V5 | 3.8 | 53 | 44 | 14.8% | 0.33/0.62 | 10000 | 70 | 220 |
| E1 | 3.4 | 59 | 55 | 16.5% | 0.33/0.62 | 10000 | 70 | 285 |
| E2 | 3.3 | 63 | 59 | 17.4% | 0.33/0.62 | 10000 | 70 | 255 |
| E3 | 3.1 | 64 | 65 | 17.7% | 0.33/0.63 | 8000 | 80 | 430 |
| E4 | 3.7 | 55 | 47 | 15.2% | 0.33/0.62 | 10000 | 80 | 210 |
| E5 | 3.6 | 56 | 49 | 15.5% | 0.33/0.63 | 10000 | 70 | 300 |
| E6 | 4.6 | 9.6 | 6.6 | 10.4% | 0.67/0.33 | 4000 | 80 | 330 |
| E7 | 4.8 | 12.1 | 8.0 | 13.1% | 0.67/0.33 | 4000 | 80 | 345 |
| E8 | 3.6 | 57 | 49 | 15.9% | 0.33/0.62 | 10000 | 70 | 230 |
| E9 | 4.7 | 11.0 | 7.4 | 11.9% | 0.67/0.33 | 4000 | 80 | 360 |
| E10 | 3.5 | 51 | 46 | 14.3% | 0.33/0.62 | 10000 | 80 | 195 |
| E11 | 3.5 | 58 | 51 | 16.0% | 0.33/0.62 | 10000 | 80 | 220 |
| E12 | 3.7 | 56 | 48 | 15.7% | 0.33/0.62 | 10000 | 80 | 235 |
| E13 | 3.6 | 55 | 48 | 15.3% | 0.34/0.62 | 10000 | 70 | 310 |
| E14 | 3.6 | 58 | 51 | 16.1% | 0.33/0.62 | 10000 | 70 | 335 |
| E15 | 4.6 | 11.1 | 7.6 | 12.1% | 0.67/0.33 | 4000 | 80 | 360 |
| E16 | 3.6 | 52 | 46 | 14.5% | 0.33/0.62 | 10000 | 70 | 230 |
| E17 | 3.8 | 55 | 45 | 15.2% | 0.33/0.62 | 10000 | 70 | 205 |
| E18 | 3.4 | 49 | 46 | 13.8% | 0.32/0.62 | 10000 | 70 | 240 |
| E19 | 3.3 | 59 | 55 | 16.2% | 0.33/0.62 | 10000 | 70 | 340 |

TABLE 3

Structural formulae of the materials for the OLEDs

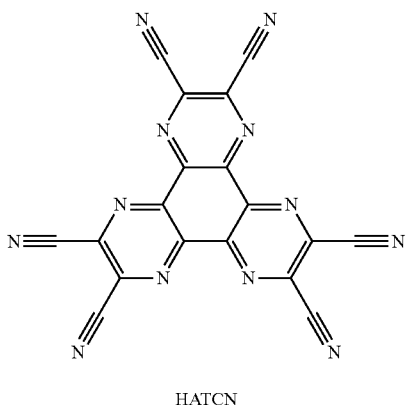

HATCN

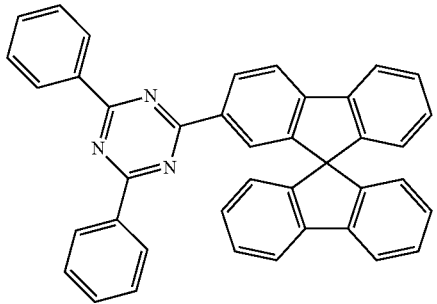 [SMILES: c1ccc(-c2nc(-c3ccccc3)nc(-c3ccc4c(c3)C3(c5ccccc5-c5ccccc53)c3ccccc3-4)n2)cc1]

ST1

TABLE 3-continued
Structural formulae of the materials for the OLEDs
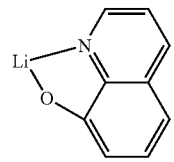
LiQ
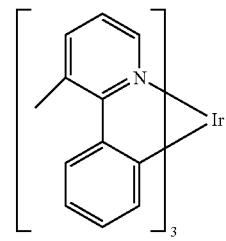
TEG1
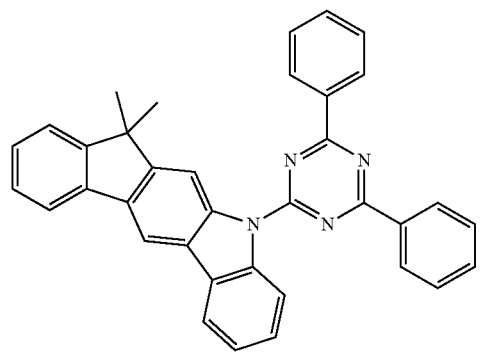 [SMILES: CC1(C)c2ccccc2-c2cc3c4ccccc4n(-c4nc(-c5ccccc5)nc(-c5ccccc5)n4)c3cc21]
IC1
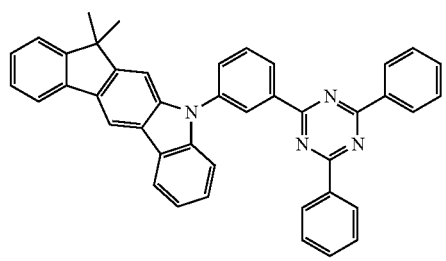
IC2
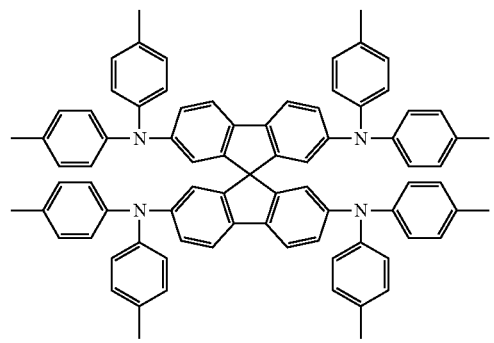
SpA1 (prior art)
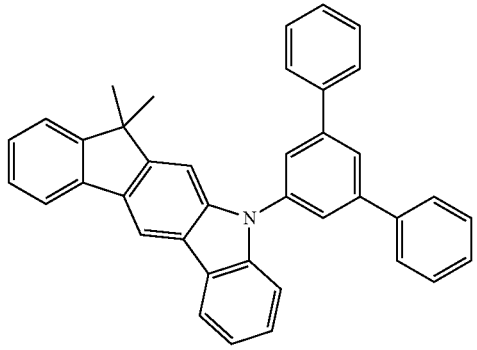
IC3
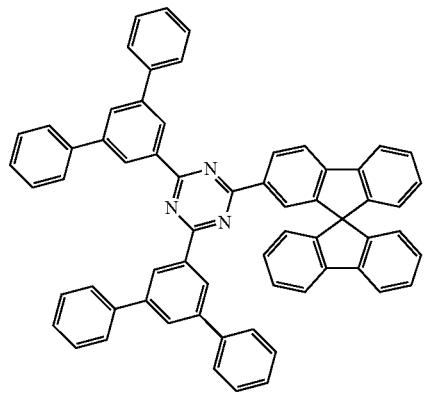 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
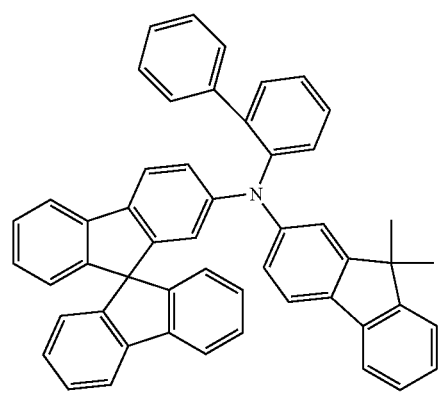 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1

TABLE 3-continued
Structural formulae of the materials for the OLEDs
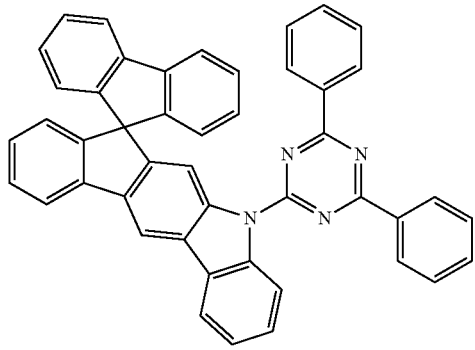 [SMILES: c1ccc(-c2nc(-c3ccccc3)nc(-n3c4ccccc4c4cc5c(cc43)C3(c4ccccc4-c4ccccc43)c3ccccc3-5)n2)cc1]
IC4 (prior art)
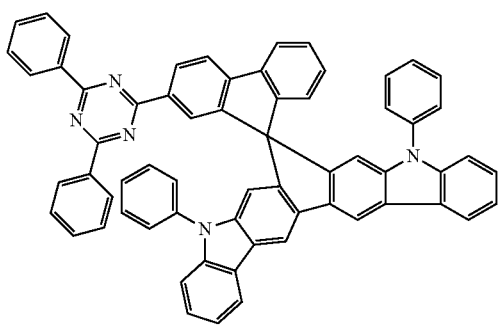 [SMILES: c1ccc(-c2nc(-c3ccccc3)nc(-c3ccc4c(c3)C3(c5ccccc5-4)c4cc5c(cc4-c4cc6c7ccccc7n(-c7ccccc7)c6cc43)c3ccccc3n5-c3ccccc3)n2)cc1]
2
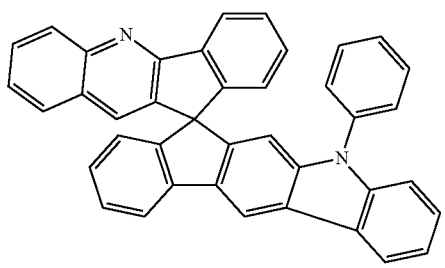 [SMILES: c1ccc(-n2c3ccccc3c3cc4c(cc32)C2(c3ccccc3-4)c3ccccc3-c3nc4ccccc4cc32)cc1]
4
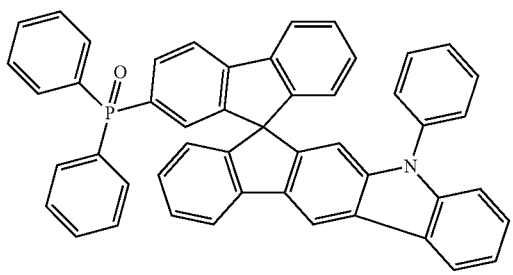 [SMILES: O=P(c1ccccc1)(c1ccccc1)c1ccc2c(c1)C1(c3ccccc3-2)c2ccccc2-c2cc3c4ccccc4n(-c4ccccc4)c3cc21]
6
TABLE 3-continued
Structural formulae of the materials for the OLEDs
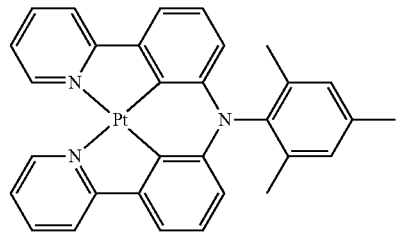
TER1
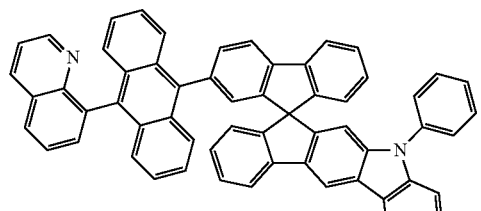
S1 (prior art)
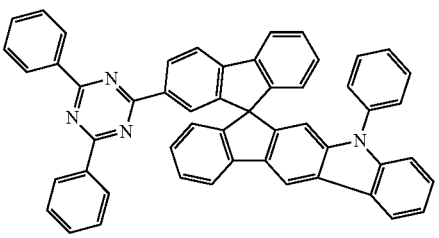 [SMILES: c1ccc(-c2nc(-c3ccccc3)nc(-c3ccc4c(c3)C3(c5ccccc5-4)c4ccccc4-c4cc5c6ccccc6n(-c6ccccc6)c5cc43)n2)cc1]
1
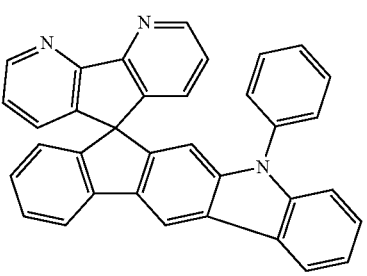 [SMILES: c1ccc(-n2c3ccccc3c3cc4c(cc32)C2(c3ccccc3-4)c3cccnc3-c3ncccc32)cc1]
3
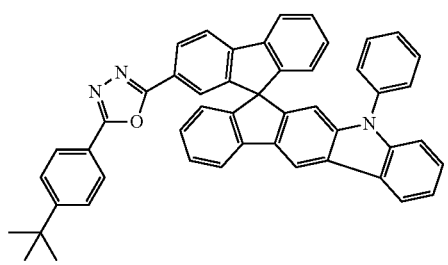 [SMILES: CC(C)(C)c1ccc(-c2nnc(-c3ccc4c(c3)C3(c5ccccc5-4)c4ccccc4-c4cc5c6ccccc6n(-c6ccccc6)c5cc43)o2)cc1]
5

TABLE 3-continued
Structural formulae of the materials for the OLEDs
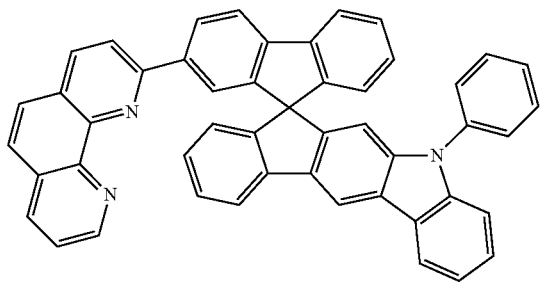 [SMILES: c1ccc(-n2c3ccccc3c3cc4c(cc32)C2(c3ccccc3-c3ccc(-c5ccc6ccc7cccnc7c6n5)cc32)c2ccccc2-4)cc1]
7
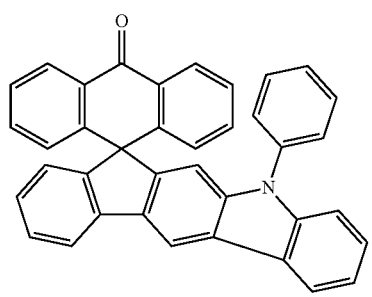 [SMILES: O=C1c2ccccc2C2(c3ccccc31)c1ccccc1-c1cc3c4ccccc4n(-c4ccccc4)c3cc12]
9
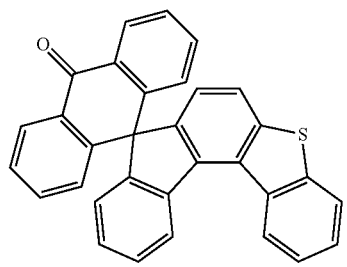 [SMILES: O=C1c2ccccc2C2(c3ccccc31)c1ccccc1-c1c2ccc2sc3ccccc3c12]
11
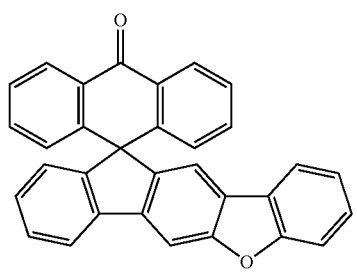 [SMILES: O=C1c2ccccc2C2(c3ccccc31)c1ccccc1-c1cc3oc4ccccc4c3cc12]
13
TABLE 3-continued
Structural formulae of the materials for the OLEDs
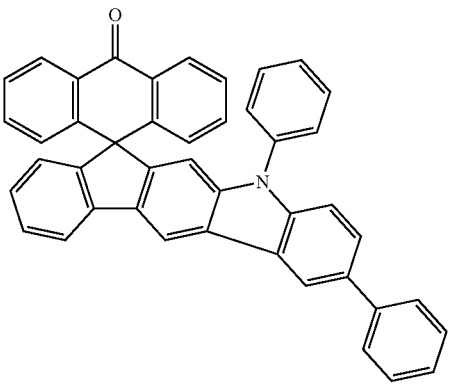 [SMILES: O=C1c2ccccc2C2(c3ccccc31)c1ccccc1-c1cc3c4cc(-c5ccccc5)ccc4n(-c4ccccc4)c3cc12]
16
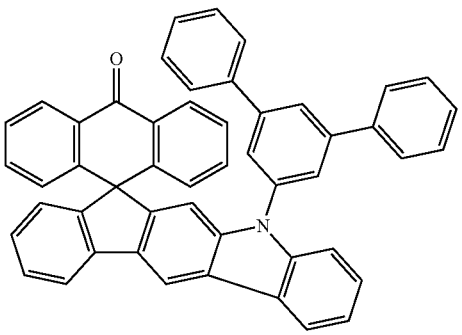 [SMILES: O=C1c2ccccc2C2(c3ccccc31)c1ccccc1-c1cc3c4ccccc4n(-c4cc(-c5ccccc5)cc(-c5ccccc5)c4)c3cc12]
10
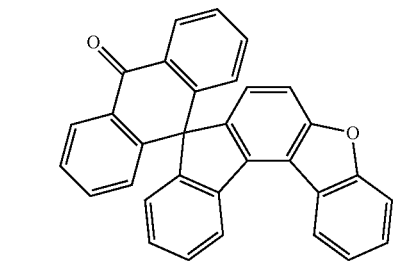 [SMILES: O=C1c2ccccc2C2(c3ccccc31)c1ccccc1-c1c2ccc2oc3ccccc3c12]
12
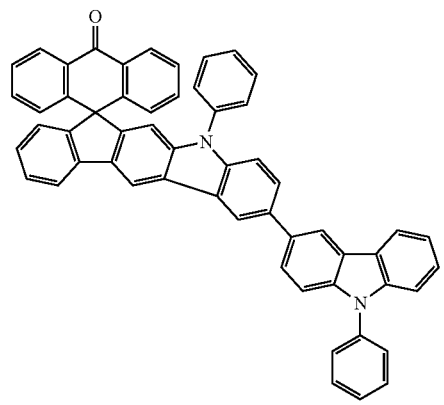 [SMILES: O=C1c2ccccc2C2(c3ccccc31)c1ccccc1-c1cc3c4cc(-c5ccc6c(c5)c5ccccc5n6-c5ccccc5)ccc4n(-c4ccccc4)c3cc12]
14

TABLE 3-continued

Structural formulae of the materials for the OLEDs

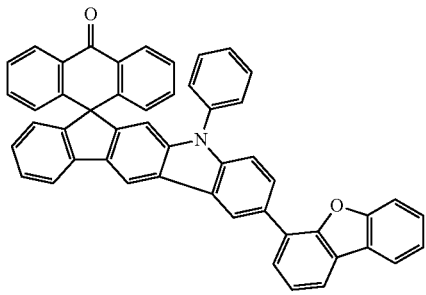 [SMILES: O=C1c2ccccc2C2(c3ccccc31)c1ccccc1-c1cc3c4cc(-c5cccc6c5oc5ccccc56)ccc4n(-c4ccccc4)c3cc12]

17

The invention claimed is:

1. A compound of formula (or formula (II)

formula (I)

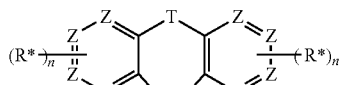

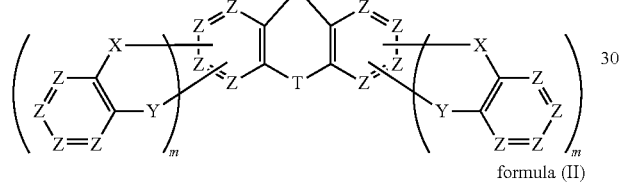

formula (II)

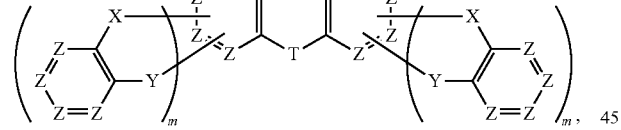

wherein

R* is, identically or differently on each occurrence, —CN, or a group selected from a keto group the formula (K)

formula (K)

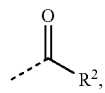

a Phosphorus oxide group of the formula (P)

formula (P)

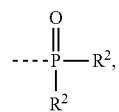

a sulfur oxide group of the formula (S)

formula (S)

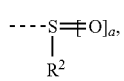

wherein a is 1 or 2, or
a group of the formulae (H-1) to (H-10)

formula (H-1)

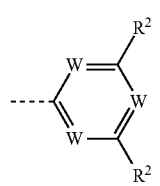

formula (H-2)

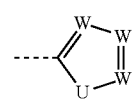

formula (H-3)

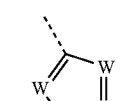

formula (H-4)

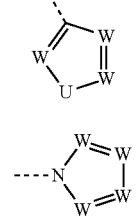

formula (H-5)

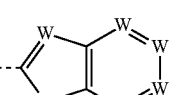

formula (H-6)

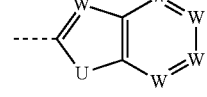

formula (H-7)

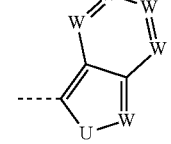

formula (H-8)

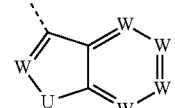

formula (H-9)

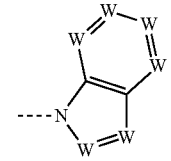

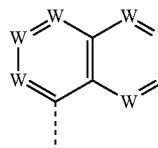

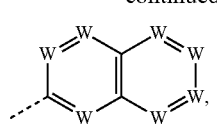

formula (H-10)

wherein the dashed bond marks the bonding, position, and

W is, identically or differently on each occurrence, $CR^2$ or N, with the proviso that at least one group W per formula is N, and U is $NR^2$, O, or S;

X, Y are, identically or differently on each occurrence, a single bond, $C(R^1)_2$, $NR^1$, O, or S, wherein at least one of the two groups X and Y of a ring is $NR^1$, O, or S;

V is a single bond, CO, CS, $P(O)R^1$, SO, or $SO_2$, with the proviso that V may only be a single bond if at least one of the groups Z in the rings bonded to V is N;

T is, identically or differently on each occurrence, a single bond, $C(R^1)_2$, CO, CS, $Si(R^1)_2$, $NR^1$, $P(O)R^1$, O, S, SO, or $SO_2$;

Z is, identically or differently on each occurrence, $CR^1$ or N if no group is bonded to Z, and C if a group is bonded to Z;

$R^1$ is, identically or differently on each occurrence, H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkyl group having 1 to 20 C atoms, a branched or cyclic alkyl, alkoxy or thioalkyl group having 3 to 20 C atoms, or an alkenyl or alkynyl group having 2 to 20 C atoms, wherein each is optionally substituted by one or more radicals $R^2$, and wherein one or more $CH_2$ groups are optionally replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO, or $SO_2$, and wherein one or more H atoms are optionally replaced by D, F, Cl, Br, I, CN, $NO_2$, an aromatic or heteroaromatic ring system having 5 to 30 aromatic ring atoms, optionally substituted by one or more radicals $R^2$, or an aryloxy or heteroaryloxy group having 5 to 30 aromatic ring atoms, optionally substituted by one or more radicals $R^2$, wherein two or more radicals $R^1$ optionally define a ring system;

$R^2$ is, identically or differently on each occurrence, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms, a branched or cyclic alkyl, alkoxy or thioalkyl group having 3 to 20 C atoms, or an alkenyl or alkynyl group having 2 to 20 C atoms, wherein each is optionally substituted by one or more radicals $R^3$, and wherein one or more $CH_2$ groups are optionally replaced by $-R^3C=CR^3-$, $-C\equiv C-$, $Si(R^3)_2$, $C=O$, $C=S$, $C=NR^3$, $-C(=O)O-$, $-C(=O)NR^3-$, $NR^3$, $P(=O)(R^3)$, $-O-$, $-S-$, SO, or $SO_2$, and wherein one or more H atoms are optionally replaced by D, F, Cl, Br, I, CN, $NO_2$, an aromatic or heteroaromatic ring system having 5 to 30 aromatic ring atoms, optionally substituted by one or more radicals $R^3$, or an aryloxy or heteroaryloxy group having 5 to 30 aromatic ring atoms, optionally substituted by one or more radicals $R^3$, wherein two or more radicals $R^2$ optionally define a ring system;

$R^3$ is, identically or differently on each occurrence, H, D, F, or an aliphatic, aromatic or heteroaromatic organic radical having 1 to 20 C atoms, wherein one or more H atoms are optionally replaced by D car F, and wherein two or more substituents $R^3$ optionally define a ring system;

m is, identically or differently on each occurrence, 0 or 1, where at least one m in formula (I) or formula (II) is 1;

n is, identically or differently on each occurrence, 0 or 1, where at least one n in formula (I) is 1, and wherein the groups X and Y are each bonded in adjacent positions to the six-membered ring of the spirobifluorene derivative.

2. The compound of claim 1, wherein said compound contains no condensed aryl groups having more than 16 aromatic ring atoms.

3. The compound of claim 1, wherein X or Y is independently, $C(R^1)_2$ or $NR^1$, and $R^1$ is on each occurrence, identical or different, selected from H, D, F, CN, $Si(R^2)_3$, or a straight-chain alkyl or alkoxyl group having 1 to 20 C or a branched or cyclic alkyl or alkoxy group having 3 to 20 C atoms.

4. The compound of claim 1, wherein the group R* is bonded to the modified spirobifluorene skeleton in position 2' or in position 7'.

5. The compound of claim 1, wherein one of the two groups X and Y is a single bond and the other of the two groups X and Y is a group $NR^1$.

6. The compound of claim 1, wherein the group T is, identically or differently on each occurrence, a single bond, $C(R^1)_2$, O, or S.

7. The compound of claim 1, wherein one of the two indices m in formula (I) or formula (II) is 1 and the other is zero.

8. The compound of claim 1, wherein one of the two indices n in formula (I) is 1 and the other is zero.

9. An oligomer, polymer, or dendrimer, comprising one or more compounds of claim 1, wherein the bond(s) to the polymer, oligomer, or dendrimer, may be localised at any desired positions in formula (I) or (II) that are substituted by $R^1$, or $R^2$.

10. A formulation comprising at least one compound of claim 1 and at least one solvent.

11. A formulation comprising at least one oligomer, polymer, or dendrimer of claim 9 and at least one solvent.

12. A process for the preparation of the compound of claim 1, wherein
a heteroaryl group is condensed onto a spirobifluorene group which is substituted by an electron-deficient group, or wherein
a cyclisation reaction is carried out via which a modified spirobifluorene group is obtained.

13. An electronic device comprising at least one compound of claim 1.

14. The electronic device of claim 13, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices.

15. The electronic device of claim 13, wherein the electronic device is an organic electroluminescent device, and wherein the compound is matrix material in an emitting layer, electron-transport material in an electron-transport or electron-injection layer, or hole-blocking material in a hole-blocking layer.

16. An electronic device comprising at least one oligomer, polymer, or dendrimer, of claim 9.

17. The electronic device of claim 16, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices.

18. The electronic device of claim 16, wherein the electronic device is an organic electroluminescent device, and wherein the oligomer, polymer, or dendrimer, is matrix material in an emitting layer, electron-transport material in an electron-transport or electron-injection layer, or hole-blocking material in a hole-blocking layer.

19. The compound of claim 1, wherein $R^2$ in the formulae (K), (P), and (S), and formulae (H-1) to (H-10) is selected from an aryl or heteroaryl group having 5 to 10 aromatic ring atoms, which may be substituted by one or more radicals $R^3$.

20. The compound of claim 1, wherein a compound of formula (I) is selected from the group consisting of

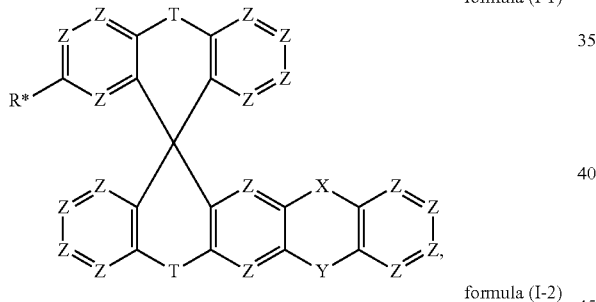

formula (I-1)

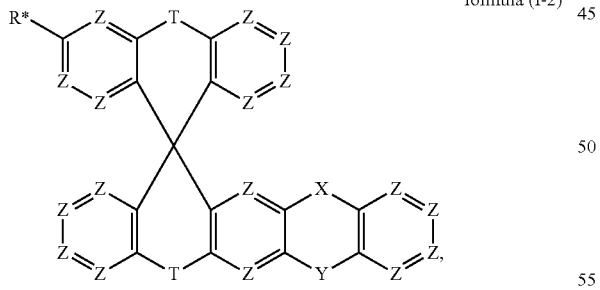

formula (I-2)

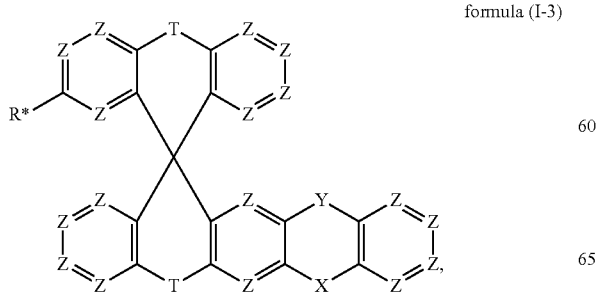

formula (I-3)

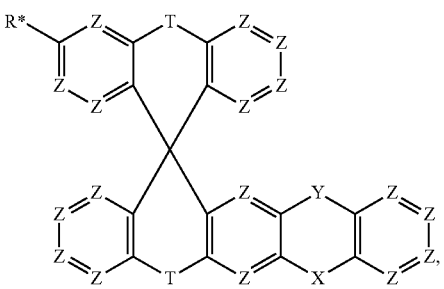

formula (I-4)

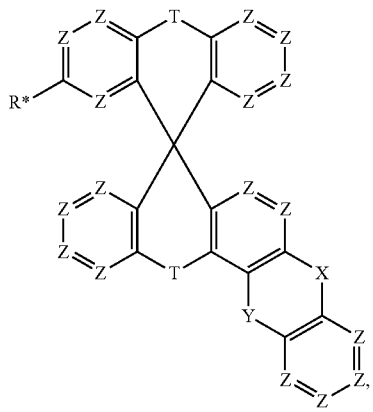

formula (I-5)

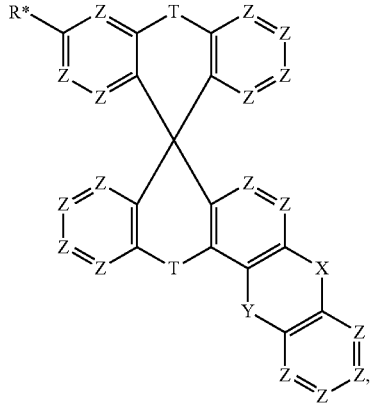

formula (I-6)

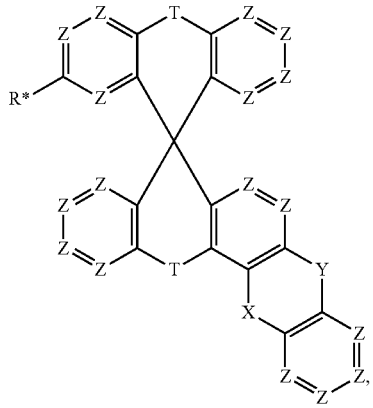

formula (I-7)

formula (I-8)
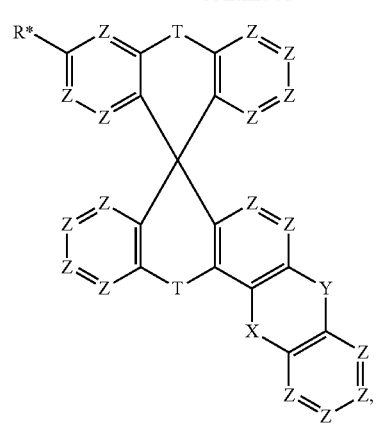
formula (I-9)
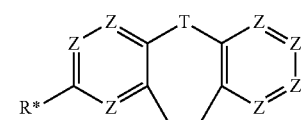
formula (I-10)
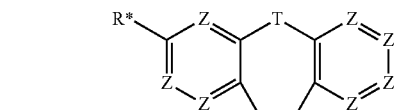
formula (I-11)
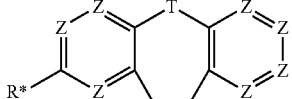
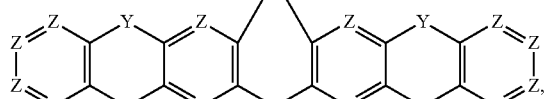
and
formula (I-12)
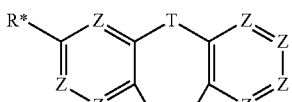
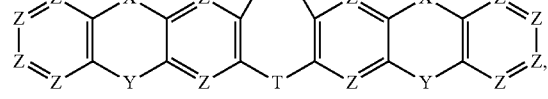
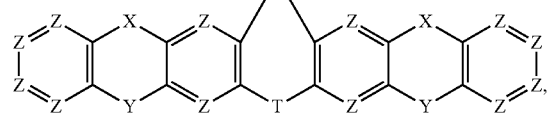
and for each of the formulae (I-1) to (I-12) not more than one group Z per aromatic ring is N and the other groups Z are $CR^1$.
* * * * *